(12) United States Patent
Baasov et al.

(10) Patent No.: US 12,364,706 B2
(45) Date of Patent: Jul. 22, 2025

(54) MODIFIED AMINOGLYCOSIDE COMPOUNDS AND USES THEREOF IN DISABLING BACTERIAL RIBOSOME

(71) Applicant: Technion Research & Development Foundation Limited, Haifa (IL)

(72) Inventors: Timor Baasov, Haifa (IL); Boris Smolkin, Ness Ziona (IL); Alina Khononov, Haifa (IL); Michal Shavit Kishkober, Matan (IL); Valery Belakhov, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1043 days.

(21) Appl. No.: 17/325,361

(22) Filed: May 20, 2021

(65) Prior Publication Data
US 2021/0275557 A1 Sep. 9, 2021

Related U.S. Application Data

(63) Continuation of application No. PCT/IL2019/051277, filed on Nov. 22, 2019.

(60) Provisional application No. 62/770,761, filed on Nov. 22, 2018.

(51) Int. Cl.
*A61K 31/7036* (2006.01)
*A61P 31/04* (2006.01)

(52) U.S. Cl.
CPC .......... *A61K 31/7036* (2013.01); *A61P 31/04* (2018.01)

(58) Field of Classification Search
CPC ............... C07H 15/224; C07H 15/232; A61K 31/7036; A61P 31/04
See application file for complete search history.

(56) References Cited

U.S. PATENT DOCUMENTS 8,653,042 B2 * 2/2014 Dozzo .................... A61P 31/04
514/35
2011/0178037 A1 7/2011 Bera et al.

FOREIGN PATENT DOCUMENTS

| WO | WO 00/39139 | 7/2000 |
|---|---|---|
| WO | WO 2017/118967 | 7/2017 |
| WO | WO 2020/105054 | 5/2020 |
| WO | WO2020/105054 A9 | 11/2020 |

OTHER PUBLICATIONS

Hanessian, Stephen et al., Tetrahedron, "Tobramycin analogues with C-5 aminoalkyl ether chains intended to mimic rings III and IV of paromomycin", 2003, vol. 59, pp. 983-993 (Year: 2003).*
Yan, Ri-Bai et al., Bioorganic & Medicinal Chemistry, "Rational design and synthesis of potent aminoglycoside antibiotics against resistant bacterial strains", 2011, vol. 19, pp. 30-40 (Year: 2011).*
International Search Report and the Written Opinion Dated Feb. 20, 2020 From the International Searching Authority Re. Application No. PCT/IL2019/051277. (11 Pages).
International Preliminary Report on Patentability Dated Jun. 3, 2021 From the International Bureau of WIPO Re. Application No. PCT/IL2019/051277. (7 Pages).
Supplementary Partial European Search Report and the European Search Opinion Dated Dec. 7, 2022 From the European Patent Office Re. Application No. 19886456.3. (14 Pages).
Le Gall et al. "Synthesis and Transfection Properties of A Series of Lipidic Neamine Derivatives", Bioconjugate Chemistry, XP055020341, 20(11): 2032-2046, Published on Web Oct. 22, 2009.
Smolkin et al. "Towards Catalytic Antibiotics: Redesign of Aminoglycosides to Catalytically Disable Bacterial Ribosomes", ChemBioChem, XP093002698, 20(2): 247-259, Published Online Nov. 25, 2018.

* cited by examiner

*Primary Examiner* — Bahar Craigo

(57) ABSTRACT

Modified aminoglycoside compounds represented by Formula I as defined and described in the specification are provided. The modified aminoglycosides feature a diamine-containing functional moiety at one or more of positions 3', 4' and 6'. Uses of the modified aminoglycosides as antimicrobial (e.g., antibacterial) agents, and in treating medical conditions associated with microorganisms, are also provided.

11 Claims, 14 Drawing Sheets
(8 of 14 Drawing Sheet(s) Filed in Color)
Specification includes a Sequence Listing.

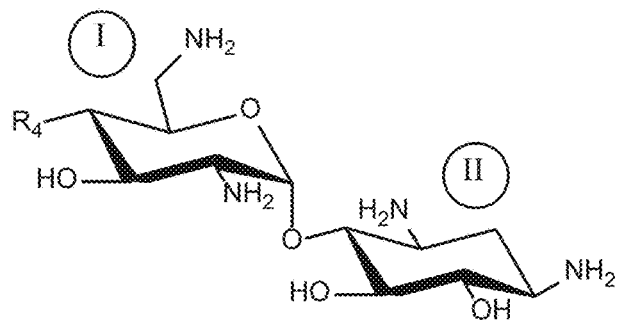
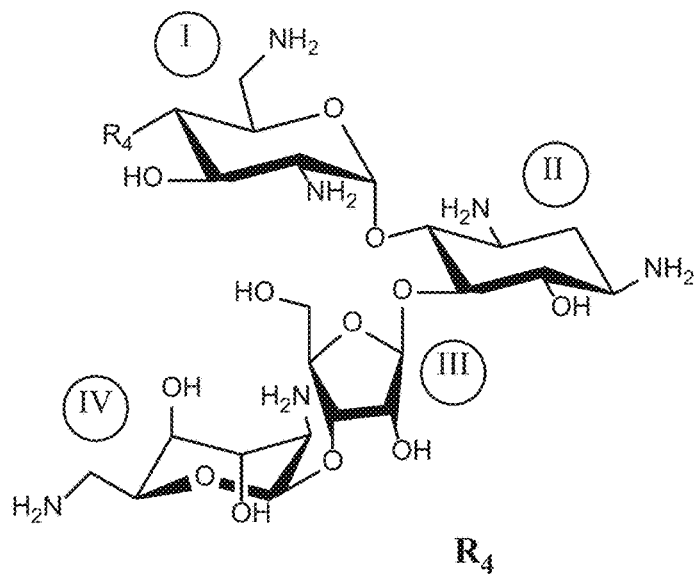
FIG. 1

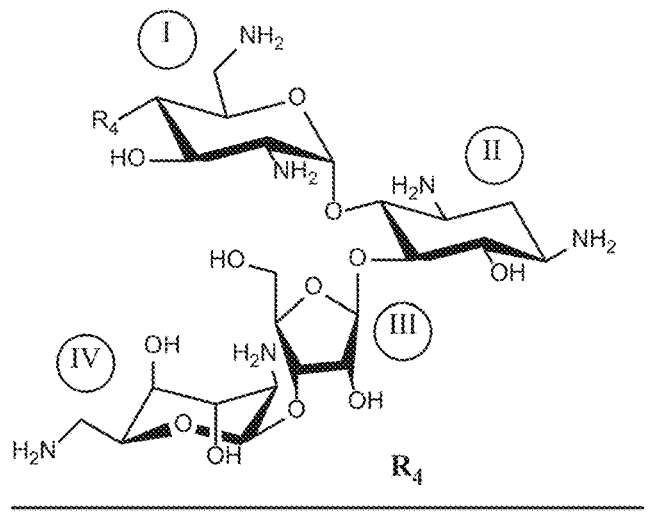
Compound 6: 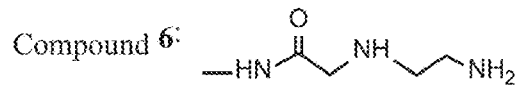
Compound 7: 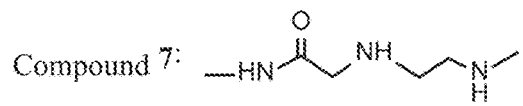
Compound 8: 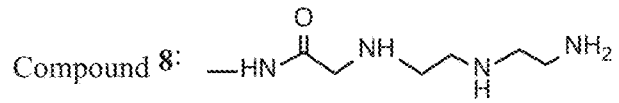
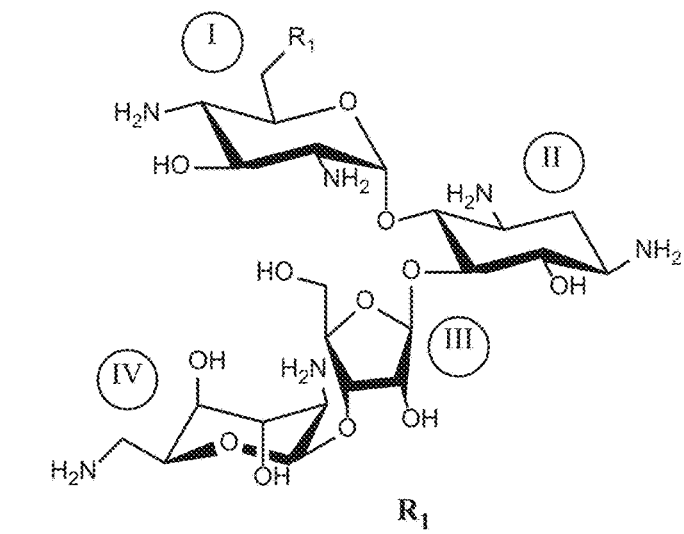
Compound 9: 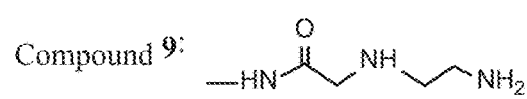
Compound 10: 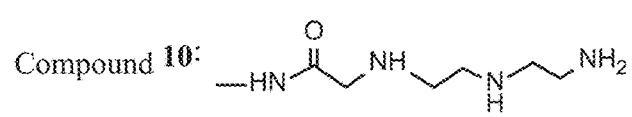
FIG. 1 (Cont.)

FIG. 5

Table 1. Comparative antibacterial activity (MIC values) and inhibition of protein translation (IC90 values) in the prokaryotic system of NeoB and synthetic compounds 1-10.[a]

| Compd. | Gram-negative | | Gram-positive | | MIC [µg mL⁻¹] P. aeruginosa | | | MRSA | | Geobacillus | | IC$_{50}$ [µM] |
|---|---|---|---|---|---|---|---|---|---|---|---|---|
| | a | b | c | d | e | f | g | h | i | j | k | |
| NeoB | 12 | >384 | 6 | 0.75-1.5 | >192 | 48-96 | 192 | >192 | 48 | 0.2 | 12 | 0.01 ± 0.002 |
| 1 | 384 | >384 | 192 | 48 | 48-96 | 48-96 | 48-96 | 192 | 48 | 6 | 12 | 2.03 ± 0.3 |
| 2 | 48 | 48 | 6 | 6 | 24-48 | 6-12 | 24 | 6-12 | 0.75 | 0.2 | 0.8 | 0.02 ± 0.001 |
| 3 | 96 | 96 | 6 | 6-12 | 48 | 12 | 24 | 24 | 3 | 0.2 | 0.8 | 0.03 ± 0.005 |
| 4 | 48 | 48-96 | 6 | 3-6 | 96 | 48 | 48 | 24 | 6 | 0.2 | 0.8 | 0.03 ± 0.007 |
| 5 | 192 | 192 | 24 | 12 | - | - | - | - | - | - | - | 0.08 ± 0.005 |
| 6 | 24 | 48 | 6 | 2 | 6 | 6 | 48 | 24-48 | 1.5 | 0.2 | 0.4 | 0.005 ± 0.0005 |
| 7 | 24 | 24 | 3 | 3-6 | 24 | 24 | 48 | 24 | 1.5 | 0.2 | 0.4 | 0.07 ± 0.004 |
| 8 | 48 | 48 | 6 | 6 | 24 | 24-48 | 48 | 12-24 | 0.75 | 0.4 | 1.5 | 0.07 ± 0.007 |
| 9 | 48 | 48 | 6 | 3-6 | 48 | 48-96 | 24 | 12 | 1.5 | 0.2 | 0.8 | 0.006 ± 0.0009 |
| 10 | 24 | 48 | 6 | 3 | 24 | - | 48-96 | 12-24 | 1.5 | 0.2 | 0.4 | 0.006 ± 0.0009 |

[a] The rows in bold highlight the most potent compounds. a: E. coli R477-100; b: E. coli 25922; c: S. epidermidis; d: B. subtilis; e: P. aeruginoa 1275; f: P. aeruginosa 27853; g: P. aeruginosa O1; h: MRSA 252; i: MRSA 15877; j: Geobacillus stearothermophilus T=160°C; k: Geobacillus stearothermophilus KanR 60°C

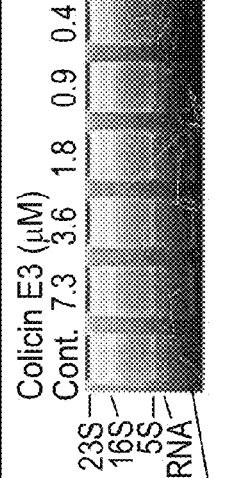

FIG. 6A

FIG. 7A
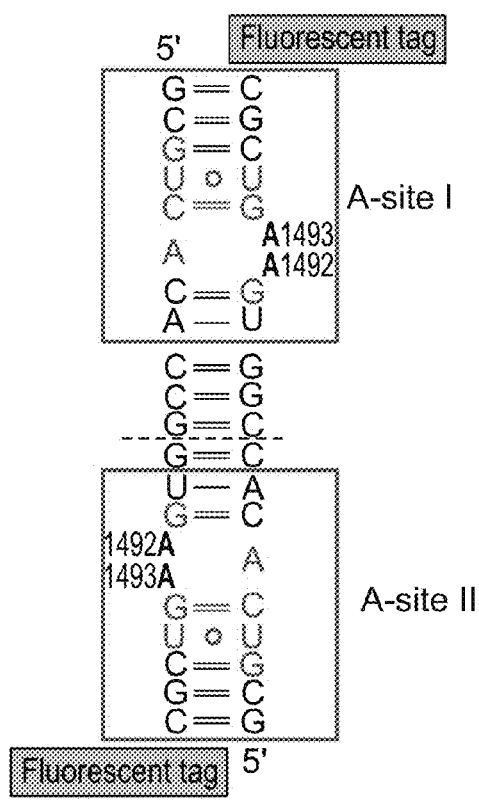
SEQ ID NO:2
FIG. 7B
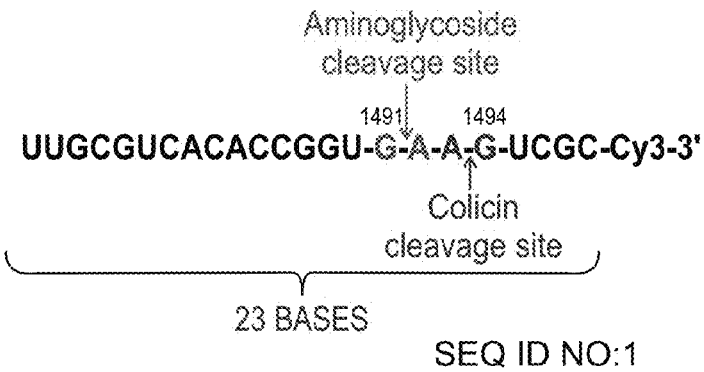
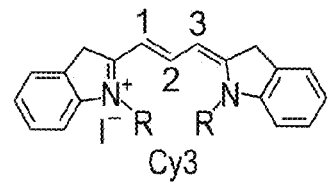
FIG. 8A  Ethylenediamine (μM)
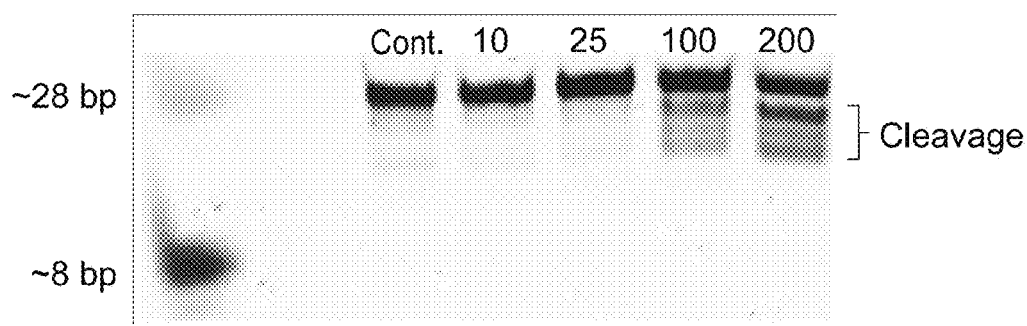
FIG. 8B  Compound 6 (μM)
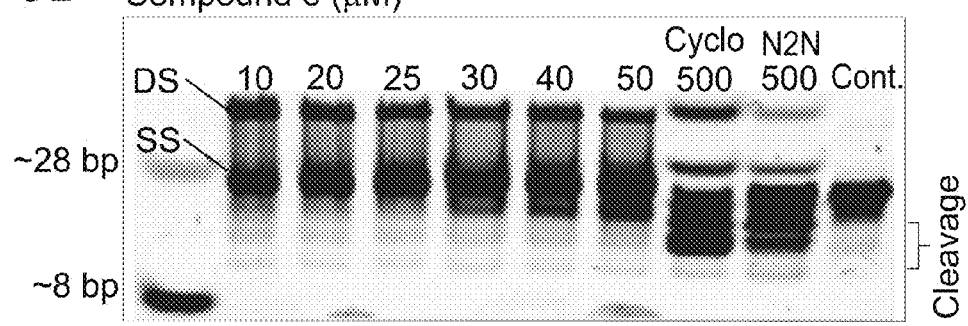

SEQUENCE LISTING

<160> NUMBER OF SEQ ID NOS: 3

<210> SEQ ID NO 1
<211> LENGTH: 23
<212> TYPE: RNA
<213> ORGANISM: Artificial Sequence
<220> FEATURE:
<223> OTHER INFORMATION: short RNA oligomer
<220> FEATURE:
<221> NAME/KEY: misc_feature
<222> LOCATION: (23)..(23)
<223> OTHER INFORMATION: Cy3 conjugated

```
<400> SEQUENCE: 1
uugcgucaca ccggugaagu cgc                                          23

<210> SEQ ID NO 2
<211> LENGTH: 21
<212> TYPE: RNA
<213> ORGANISM: Artificial Sequence
<220> FEATURE:
<223> OTHER INFORMATION: short RNA oligomer
<220> FEATURE:
<221> NAME/KEY: misc_feature
<222> LOCATION: (21)..(21)
<223> OTHER INFORMATION: may be 3' fluorescent tag conjugated

<400> SEQUENCE: 2
gcgucacacc ggugaagucg c                                            21

<210> SEQ ID NO 3
<211> LENGTH: 22
<212> TYPE: RNA
<213> ORGANISM: Artificial Sequence
<220> FEATURE:
<223> OTHER INFORMATION: 2ET4:A (PDBID) short RNA oligomer sequence

<400> SEQUENCE: 3
cgcgucacac cggugaaguc gc                                           22
```

MODIFIED AMINOGLYCOSIDE COMPOUNDS AND USES THEREOF IN DISABLING BACTERIAL RIBOSOME

RELATED APPLICATIONS

This application is a Continuation of PCT Patent Application No. PCT/IL2019/051277 having International filing date of Nov. 22, 2019, which claims the benefit of priority under 35 USC § 119(e) of U.S. Provisional Patent Application No. 62/770,761, filed on Nov. 22, 2018. The contents of the above applications are all incorporated by reference as if fully set forth herein in their entirety.

SEQUENCE LISTING STATEMENT

The ASCII file, entitled 86972SequenceListing.txt, created on May 20, 2021, comprising 1,207 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to aminoglycosides and, more particularly, but not exclusively, to newly designed aminoglycoside compounds which are aimed at disabling bacterial ribosome and are usable in treating medical conditions associated with pathogenic microorganisms such as pathogenic bacteria, including drug-resistant bacterial strains.

The ongoing emergence of multidrug-resistant pathogenic microorganism (pathogens) requires continuous intensive search for novel antimicrobial agents (e.g., antibiotics). Unfortunately, only two new classes of antibiotics, oxazolidinones and lipoproteins have been introduced into clinical practice during the last decades. Furthermore, it is well documented that once a new antibiotic is introduced into the clinic, whether it is a novel chemical entity acting at a distinct bacterial target or a semisynthetic derivative that counters the resistance to its parent drug, within only a short matter of time new resistance will emerge and create a serious public health problem. Some bacterial strains have developed multidrug resistance that covers the majority of currently available antibiotics. The significance of this health problem has re-energized the search for new antibacterial agents and novel approaches.

One innovative approach is the development of catalytic antibiotics: the pharmacophore of an existing antibiotic is modified to include a "catalytic warhead" that disables the target in a catalytic manner. Unlike conventional antibiotics that act on their targets in either a reversible (non-covalent interaction) or an irreversible manner (covalent interaction), the antibiotics acting in a catalytic manner promote multiple turnovers of a catalytic cycle. The possible benefits include 1) activity at lower dosages and consequently reduced side effects, 2) activity against drug-resistant bacteria, and 3) reduced potential for generating new resistance.

Catalytic drugs have been reported previously [Z. Yu, J. A. Cowan, Chem. Eur. J. 2017, 23, 14113-14127], and include, for example, numerous peptide-cleaving agents based on small-molecule metal complexes as artificial proteases [J. Suh, W. S. Chei, Curr. Opin. Chem. Biol. 2008, 12, 207-213], site-specific RNA-cleaving agents that combine a reactive moiety (phosphodiester cleavage directed, nonmetallic warhead) with a recognition element (sequence-specific hybridization to target RNA) [T. Niittym-ki, H. Lonnberg, Org. Biomol. Chem. 2006, 4, 15-25], and nonmetallic small-organic molecules as artificial ribonucleases [T. Lçnnberg, K. M. Kero, Org. Biomol. Chem. 2012, 10, 569-574; R. Salvio, R. Cacciapaglia, L. Mandolini, F. Sansone, A. Casnati, RSC Adv. 2014, 4, 34412-34416].

Aminoglycosides are highly potent, broad-spectrum antibiotics with many desirable properties for the treatment of life-threatening infections.

It is accepted that the mechanism of action of aminoglycoside antibiotics, such as paromomycin, involves interaction with the prokaryotic ribosome, and, more specifically, involves binding to the decoding A-site of the 16S ribosomal RNA, which leads to protein translation inhibition and interference with the translational fidelity.

Several achievements in bacterial ribosome structure determination, along with crystal and NMR structures of bacterial A-site oligonucleotide models, have provided useful information for understanding the decoding mechanism in prokaryote cells and understanding how aminoglycosides exert their deleterious misreading of the genetic code. It has been shown that aminoglycosides exert their therapeutic (bactericidal) effect by selectively binding to the aminoacyl tRNA binding site (A-site) of the bacterial 16S rRNA, thereby interfering with translational fidelity during protein synthesis [S. Magnet, J. S. Blanchard, Chem. Rev. 2005, 105, 477-498].

Previous reports on the ability of copper-aminoglycoside complexes to promote hydrolytic and oxidative cleavage of RNA have prompted the potential use of these complexes as metallodrugs with potent antibacterial activity. See, for example, A. Sreedhara, A. Patwardhan, J. A. Cowan, Chem. Commun. 1999, 2, 1147-1148; A. Patwardhan, J. A. Cowan, Dalton Trans. 2011, 40, 1795-1801; W. Szczepanik, A. Krezel, M. Brzezowska, E. Dworniczek, M. Jezowska-Bojczuk, Inorg. Chim. Acta 2008, 361, 2659-2666; and W. Szczepanik, J. Ciesiolka, J. Wrzesin'ski, J. Skala, M. Jezowska-Bojczuk, Dalton Trans. 2003, 1488-1494. However, antibacterial tests showed no significant enhancement in the activity of the copper-aminoglycoside complex relative to that of the parent aminoglycoside [W. Szczepanik, E. Dworniczek, J. Ciesiolka, J. Wrzesin'ski, J. Skala, M. Jezowska-Bojczuk, J. Inorg. Biochem. 2003, 94, 355-364].

Some studies have shown that several simple oligoamines [Komiyama et al., J. Org. Chem. 1997, 62, 2155-2160; Yoshinari et al., Chem. Lett. 1990, 519-522], as well as basic polypeptides [Oivanen et al., Chem. Rev. 1998, 98, 961-990] have shown catalytic cleavage of RNA. It has also been shown that Neomycin B (NeoB), which has three times as many amines as 1,3-propanediamine, catalyzes hydrolysis of adenylyl(3'-5')-adenosine (ApA) 3-fold faster than 1,3-propanediamine [Kirk et al., Chem. Commun. 1998, 147-148]. NeoB consists of the meso-1,3-diaminocyclitol (2-deoxystreptamine, 2-DOS) ring for which the $pK_a$ values of 5.74 and 8.04 were reported.

Yan et al. [Bioorg. Med. Chem. 2011, 19, 30-40] reported a series of new derivatives of kanamycin B modified at the 4'-OH position that showed antibacterial activity against both wild-type and resistant bacteria. Therein, it is described that the side-chain-free amine is best tolerated by the ribosome; and that the A-site of the ribosome can accommodate bulky substituents linked at the 4'-position.

Several studies have showed that a successful cleavage of an RNA phosphodiester bond requires substantial motion in the HO—C2'-C3'-O—P bonds of the ribose-3'-phosphate region to reach the necessary low energy transition state wherein the C2'-OH group is orientated for in-line nucleophilic attack on the scissile bond [T. Lønnberg, K. M. Kero, Org. Biomol. Chem. 2012, 10, 569-574]. Such flexibility is usually achieved by the enzyme-induced flipping of the base attached to the RNA scissile bond, as supported, for example, by S. M. K. Takahashi, Acad. Press. New York 1982, 435-468; X. J. Yang, T. Gerczei, L. Glover, C. C. Correll, Nat. Struct. Biol. 2001, 8, 968-973; and P. B. Rupert, A. R. Ferre-D'Amare, Nature 2001, 410, 780-786.

A mechanism for colicin E3 (ColE3), a natural enzymatic toxin produced in several *E. coli* strains, that selectively cleaves a phosphodiester bond between A1493 and G1494 of 16S rRNA, has been proposed recently [C. L. Ng, K. Lang, N. A. G. Meenan, A. Sharma, A. C. Kelley, C. Kleanthous, V. Ramakrishnan, Nat. Struct. Mol. Biol. 2010, 17, 1241-1246]. This cleavage impairs the protein translation process and consequently leads to cell death. The proposed mechanism of ColE3 also explains why this natural ribonuclease cleaves the specific position in the A site of rRNA, between A1493 and G1494. This region of the A site is very important functionally (for correct proofreading) and is also one of the most flexible and accessible regions in the whole ribosome because it needs to accommodate the incoming aminoacyl-tRNA.

WO 2017/118967 describes modified aminoglycosides featuring a core structure based on Rings I, II and optionally III of paromomycin.

U.S. Pat. No. 7,635,586 discloses aminoglycosides derived from Neomycin B, and their use as highly potent and effective antibiotics, while reducing or even blocking antibiotic resistance.

Additional background art includes Nudelman, I., et al., Bioorg Med Chem Lett, 2006. 16(24): p. 6310-5; Hobbie, S. N., et al., Nucleic Acids Res, 2007. 35(18): p. 6086-93; Kondo, J., et al., Chembiochem, 2007. 8(14): p. 1700-9; Rebibo-Sabbah, A., et al., Hum Genet, 2007. 122(3-4): p. 373-81; Azimov, R., et al., Am J Physiol Renal Physiol, 2008. 295(3): p. F633-41; Hainrichson, M., et al., Org Biomol Chem, 2008. 6(2): p. 227-39; Hobbie, S. N., et al., Proc Natl Acad Sci USA, 2008. 105(52): p. 20888-93; Hobbie, S. N., et al., Proc Natl Acad Sci USA, 2008. 105(9): p. 3244-9; Nudelman, I., et al., Adv. Synth. Catal., 2008. 350: p. 1682-1688; Nudelman, I., et al., J Med Chem, 2009. 52(9): p. 2836-45; Venkataraman, N., et al., PLoS Biol, 2009. 7(4): p. e95; Brendel, C., et al., J Mol Med (Berl), 2010. 89(4): p. 389-98; Goldmann, T., et al., Invest Ophthalmol Vis Sci, 2010. 51(12): p. 6671-80; Malik, V., et al., Ther Adv Neurol Disord, 2010. 3(6): p. 379-89; Nudelman, I., et al., Bioorg Med Chem, 2010. 18(11): p. 3735-46; Warchol, M. E., Curr Opin Otolaryngol Head Neck Surg, 2010. 18(5): p. 454-8; Lopez-Novoa, J. M., et al., Kidney Int, 2011. 79(1): p. 33-45; Rowe, S. M., et al., J Mol Med (Berl), 2011. 89(11): p. 1149-61; Vecsler, M., et al., PLoS One, 2011. 6(6): p. e20733; U.S. Pat. Nos. 3,897,412, 4,024,332, 4,029,882, and 3,996,205; Greenberg et al., *J. Am. Chem. Soc.*, 1999, 121, 6527-6541; Kotra et al., antimicrobial agents and chemotherapy, 2000, p. 3249-3256; Haddad et al., *J. Am. Chem. Soc.*, 2002, 124, 3229-3237; Kandasamy, J. et al., *J. Med. Chem.* 2012, 55, pp. 10630-10643; Duscha, S. et al., *MBio*, 2014, 5(5), p. e01827-14; Huth, M. E. et al., *J Clin Invest.*, 2015, 125(2), pp. 583-92; Shulman, E. et al., *J Biol Chem.*, 2014, 289(4), pp. 2318-30 and FR Patent No. 2,427,341, JP Patent No. 04046189.

Further background art includes T. Lønnberg, K. M. Kero, Org. Biomol. Chem. 2012, 10, 569-574; C. L. Ng, K. Lang, N. A. G. Meenan, A. Sharma, Nat. Struct. Mol. Biol. 2010, 17, 1241-1246; M. Komiyama, K. Yoshinari, J. Org. Chem. 1997, 62, 2155-2160; K. Yoshinari, M. Komiyama, Chem. Lett. 1990, 19, 519-522; R.-B. B. Yan, M. Yuan, Y. F. Wu, X. F. You, X.-S. S. Ye, Bioorg. Med. Chem. 2011, 19, 30-40; K. C. Nicolaou, V. A. Adsool, C. R. H. Hale, Org. Lett. 2010, 12, 1552-1555; N. S. Chindarkar, A. H. Franz, ARKIVOC (Gainesville, FL, U.S.) 2008, 21; R. Pathak, D. Perez-Fernandez, R. Nandurdikar, S. K. Kalapala, E. C. Bottger, A. Vasella, Helv. Chim. Acta 2008, 91, 1533-1552; R. Pathak, E. C. C. Bçttger, A. Vasella, Helv. Chim. Acta 2005, 88, 2967-2985; E. D. Goddard-Borger, R. V. Stick, Org. Lett. 2007, 9, 3797-3800; B. a. Maguire, L. M. Wondrack, L. G. Contillo, Z. Xu, RNA 2008, 14, 188-195; P. Pfister, S. Hobbie, Q. Vicens, E. C. Bçttger, E. Westhof, ChemBioChem 2003, 4, 1078-1088; Q. Vicens, E. Westhof, Chem. Biol. 2002, 9, 747-755; Y. Miao, V. A. Feher, J. A. McCammon, J. Chem. Theory Comput. 2015, 11, 3584-3595; Y. T. Pang, Y. Miao, Y. Wang, J. A. McCammon, J. Chem. Theory Comput. 2017, 13, 9-19; C. C. Correll, X. Yang, T. Gerczei, J. Beneken, M. J. Plantinga, J. Synchrotron Radiat. 2004, 11, 93-96; M. J. Belousoff, B. Graham, L. Spiccia, Y. Tor, Org. Biomol. Chem. 2009, 7, 30-33; R. J. Leatherbarrow, GraFit 5, Erithacus Software Ltd., Horley, U.K., 2001; S. Carr, D. Walker, R. James, C. Kleanthous, A. M. Hemmings, Structure 2000, 8, 949-960; and T. Baasov, B. Smolkin, A. Khononov, M. Shavit, V. Belakhov, ChemBioChem 2019, 20, 247-259. The teachings of all of these documents are incorporated by reference as if fully set forth herein.

SUMMARY OF THE INVENTION

The emergence of multidrug-resistant pathogens that are resistant to the majority of currently available antibiotics is a significant clinical problem. The development of new antibacterial agents and novel approaches is therefore extremely important.

The present inventors have designed and practiced a series of new derivatives of the natural aminoglycoside antibiotics, which were shown to exhibit significant antibacterial activity against wild-type bacteria and were especially potent against resistant and pathogenic strains, and which may be potentially used as a basis for the design of catalytic antibiotics.

According to an aspect of some embodiments of the present invention there is provided a compound (a modified aminoglycoside) represented by Formula I:

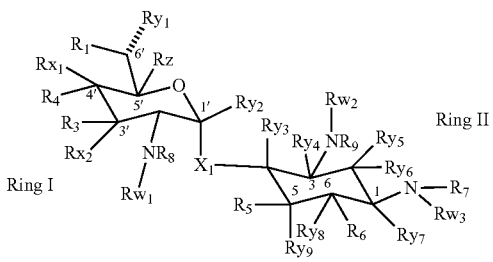

Formula I or a pharmaceutically acceptable salt thereof,
wherein:
the dashed line indicates a stereo-configuration of position 6' being an R configuration or an S configuration;
$X_1$ is O or S;
Rx1, Rx2, Ry1 and Rz are each independently selected from hydrogen, alkyl and cycloalkyl;

Ry2-Ry9 and Rw1-Rw3 are each independently selected from hydrogen, alkyl, and cycloalkyl;

$R_1$, $R_3$ and $R_4$ are each independently $NR_{23}R_{24}$, $OR_{20}$ or a diamine-containing moiety, wherein $R_{20}$ is hydrogen, alkyl, cycloalkyl or the diamine-containing moiety, and each of $R_{23}$ and $R_{24}$ is independently hydrogen, alkyl, cycloalkyl or acyl, provided that at least one of $R_1$, $R_3$ and $R_4$ is or comprises the diamine-containing moiety;

$R_5$ and $R_6$ are each independently selected from hydrogen, alkyl, alkenyl, alkynyl, cycloalkyl, heteroalicyclic, aryl, heteroaryl and $OR_{16}$, wherein $R_{16}$ is independently selected from hydrogen, a monosaccharide moiety and an oligosaccharide moiety; and $R_7$-$R_9$ are each independently selected from the group consisting of hydrogen and acyl, wherein the diamine-containing moiety comprises at least two amine-containing groups and at least one linking group linking the at least two amine-containing groups, and wherein the amine-containing groups and the at least one linking group are arranged such that:
(i) a difference in the pKa of at least two of the amine-containing groups is at least 1; and/or
(ii) when the compound is in a physiological environment, at least one of the amine-containing groups is protonated at physiological pH while at least another of the amine-containing groups is non-protonated; and/or
(iii) when the compound interacts with a prokaryotic ribosomal RNA decoding site (A-site), the RNA undergoes a conformational change such that an O—P—O angle of at least one phosphodiester bond is higher than 100°; and/or
(iv) when the compound interacts with a prokaryotic ribosomal RNA decoding site (A-site), the functional moiety is capable of adopting a configuration in which one of the amine-containing groups is in close proximity and suitable orientation so as to interact with a 2'-OH group of a ribose of a nucleotide in the RNA and another amine-containing moiety is in close proximity and suitable orientation so as to interact with a phosphate group of a nucleotide of an adjacent nucleotide.

According to some of any of the embodiments described herein, the diamine-containing functional moiety is represented by the Formula:

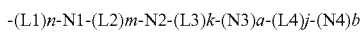
-(L1)*n*-N1-(L2)*m*-N2-(L3)*k*-(N3)*a*-(L4)*j*-(N4)*b* wherein: each of L1, L2, L3 and L4 is independently the linking group; each of N1, N2, N3 and N4 is an amine-containing group; and each of a, b, n, m, k, and j is independently 0 or 1.

According to some of any of the embodiments described herein, each of the amine-containing groups is independently selected from amine, amide, guanyl, guanidyl, amide and hydrazine.

According to some of any of the embodiments described herein, each of the linking groups (in Formula I and any of the respective embodiments and combinations thereof) is independently a hydrocarbon group being of 1 to 6 carbon atoms in length.

According to some of any of the embodiments described herein, each of the linking groups (in Formula I and any of the respective embodiments and combinations thereof) is independently an alkylene chain being of 1 to 6, or of 1 to 4, or of 2 or 3, carbon atoms in length.

According to some of any of the embodiments described herein, the diamine-containing functional group is or comprises at least one of an ethylene diamine moiety, a methyl ethylenediamine moiety, a diethylenetriamine moiety, a N-(2-aminoethyl)pyrrolidone moiety, and a guanidine-ethyleneamine moiety.

According to some of any of the embodiments described herein, $R_4$ is or comprises the diamine-containing moiety.

According to some of any of the embodiments described herein, $R_4$ is $OR_{20}$ and $R_{20}$ is the diamine-containing moiety.

According to some of any of the embodiments described herein, $R_{20}$ is

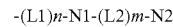
-(L1)*n*-N1-(L2)*m*-N2 wherein: n and m are each 1; L1 and L2 are each independently an alkylene of 2 or 3 carbon atoms in length; and N1 and N2 are each independently selected from amine and guanidyl.

According to some of any of the embodiments described herein, $R_4$ is the diamine-containing moiety.

According to some of any of the embodiments described herein, $R_4$ is:

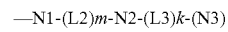
—N1-(L2)*m*-N2-(L3)*k*-(N3)

wherein: m and k are 1; L2 and L3 are each independently an alkylene of 1, 2 or 3 carbon atoms in length; N1 is amide; and each of N2 and N3 is independently an amine.

According to some of any of the embodiments described herein, $R_1$ is or comprises the diamine-containing moiety.

According to some of any of the embodiments described herein, $R_1$ is:

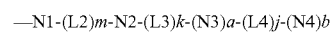
—N1-(L2)*m*-N2-(L3)*k*-(N3)*a*-(L4)*j*-(N4)*b* wherein: m and k are each 1; j is 0 or 1; a is 1; b is 0 or 1; L2, L3 and L4, if present, are each independently an alkylene of 1, 2 or 3 carbon atoms in length; N1 is amide; and each of N2, N3 and N4, if present, is independently an amine.

According to some of any of the embodiments described herein, $R_4$ is $NR_{23}R_{24}$.

According to some of any of the embodiments described herein, at least one of $R_5$ and $R_6$ is $OR_{16}$, and $R_{16}$ is a monosaccharide or an oligosaccharide.

According to some of any of the embodiments described herein, $R_5$ is $OR_{16}$ and $R_{16}$ is an oligosaccharide (e.g., a di-saccharide).

According to some of any of the embodiments described herein, $R_6$ is $OR_{16}$ and $R_{16}$ is hydrogen.

According to some of any of the embodiments described herein, the compound features a Neomycin B skeleton (e.g., as shown in Formula Ic, III or IV).

According to some of any of the embodiments described herein, each of Rx1, Rx2, Ry1 and Rz is hydrogen.

According to some of any of the embodiments described herein, each of Ry2-Ry9 and Rw1-Rw3 is hydrogen.

According to some of any of the embodiments described herein, each of $R_7$ and $R_9$ is hydrogen.

According to some of any of the embodiments described herein, the compound is one or more of Compounds 1-10, as described herein.

According to some of any of the embodiments described herein, the compound is Compound 8, as described herein.

According to an aspect of some embodiments of the present invention there is provided a pharmaceutical composition comprising a compound (a modified aminoglycoside) as described herein in any of the respective embodiments and any combination thereof.

According to an aspect of some embodiments of the present invention there is provided a compound (a modified aminoglycoside) as described herein in any of the respective embodiments and any combination thereof or the pharmaceutical composition as described herein, for use in the treatment a medical condition associated with a pathogenic microorganism.

According to an aspect of some embodiments of the present invention there is provided a method of treating a medical condition associated with a pathogenic microorganism, the method comprising administering to a subject in need thereof (e.g., a subjected afflicted with medical condition as described herein), a compound (a modified aminoglycoside) as described herein in any of the respective embodiments and any combination thereof or the pharmaceutical composition as described herein, thereby treating the medical condition in the subject.

According to some of any of the embodiments described herein, the pathogenic microorganism is a bacterium.

According to some of any of the embodiments described herein, the pathogenic microorganism is an aminoglycoside-resistant microorganism.

According to an aspect of some embodiments of the present invention there are provided processes of preparing the compounds as described herein, which are essentially as described herein.

According to an aspect of some embodiments of the present invention there are provided compounds presented herein as intermediates in the above-mentioned processes, for example, the intermediate compounds presented in FIGS. 2A, 2B and 3.

Unless otherwise defined, all technical and/or scientific terms used herein have the same meaning as commonly understood by one of ordinary skill in the art to which the invention pertains.

Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents the chemical structures of exemplary compounds according to some embodiments of the present invention.

Figure 2A:
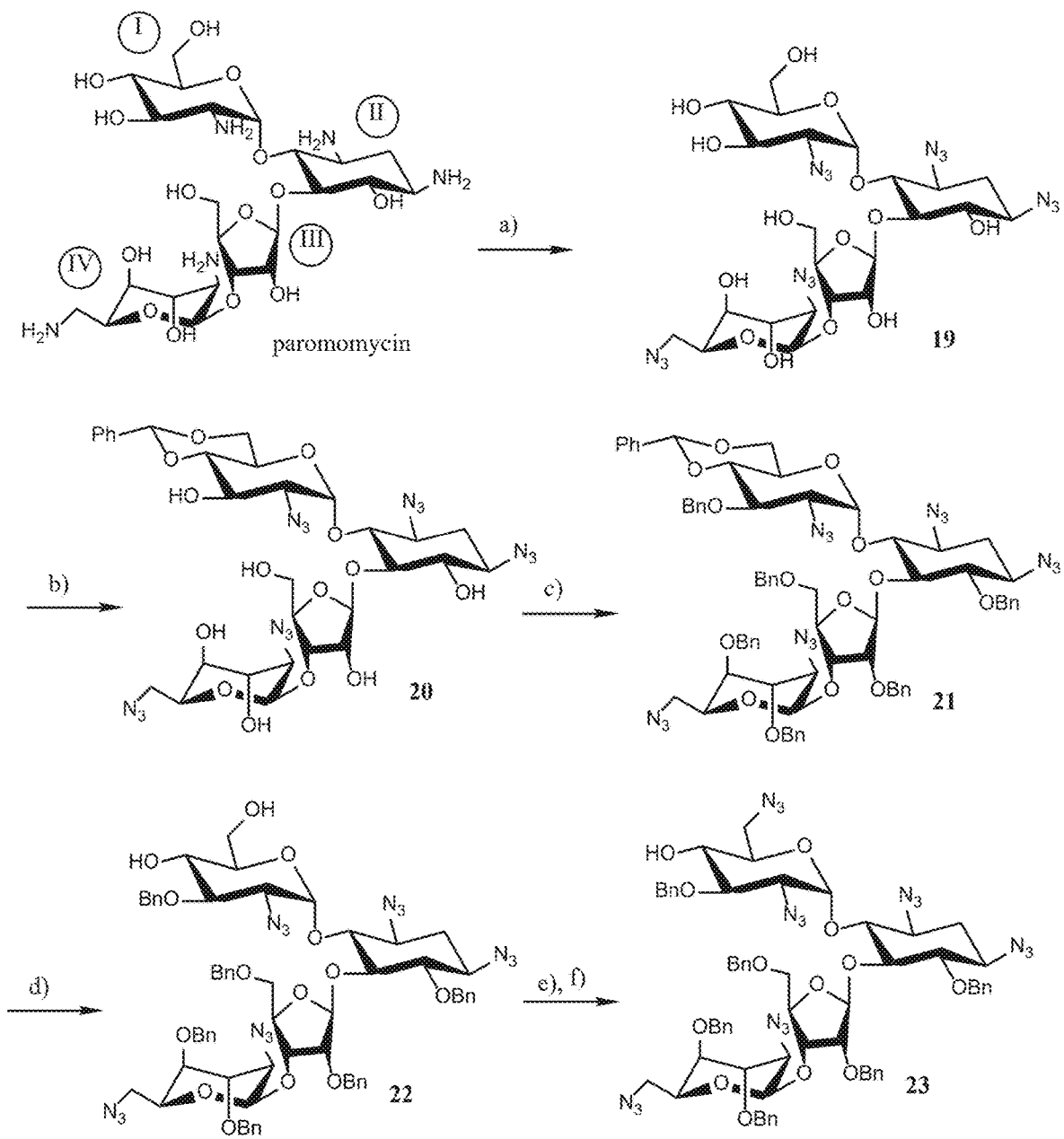

FIG. 2A is a scheme showing an exemplary synthetic pathway for preparing Compound 1. a) AcCl, MeOH; b) TfN$_3$, CuSO$_4$ (90%); c) PhCH(OMe)$_2$, CSA, DMF (83%); d) BnBr, NaH, DMF (88%); e) AcOH/H$_2$O (90%); f) TsCl, py; g) NaN$_3$, DMF (68%); h) allyl bromide, NaH, DMF (97%); i) K2OsO$_4$, NMO, acetone/H$_2$O (80%); j) PhI(OAc)$_2$, CH$_2$Cl$_2$; k) 2-azidoethanamine; l) NaBH(OAc)$_3$ (66%); m) PMe$_3$, NaOH; n) Na/NH3, THF (65%).

Figure 2B:
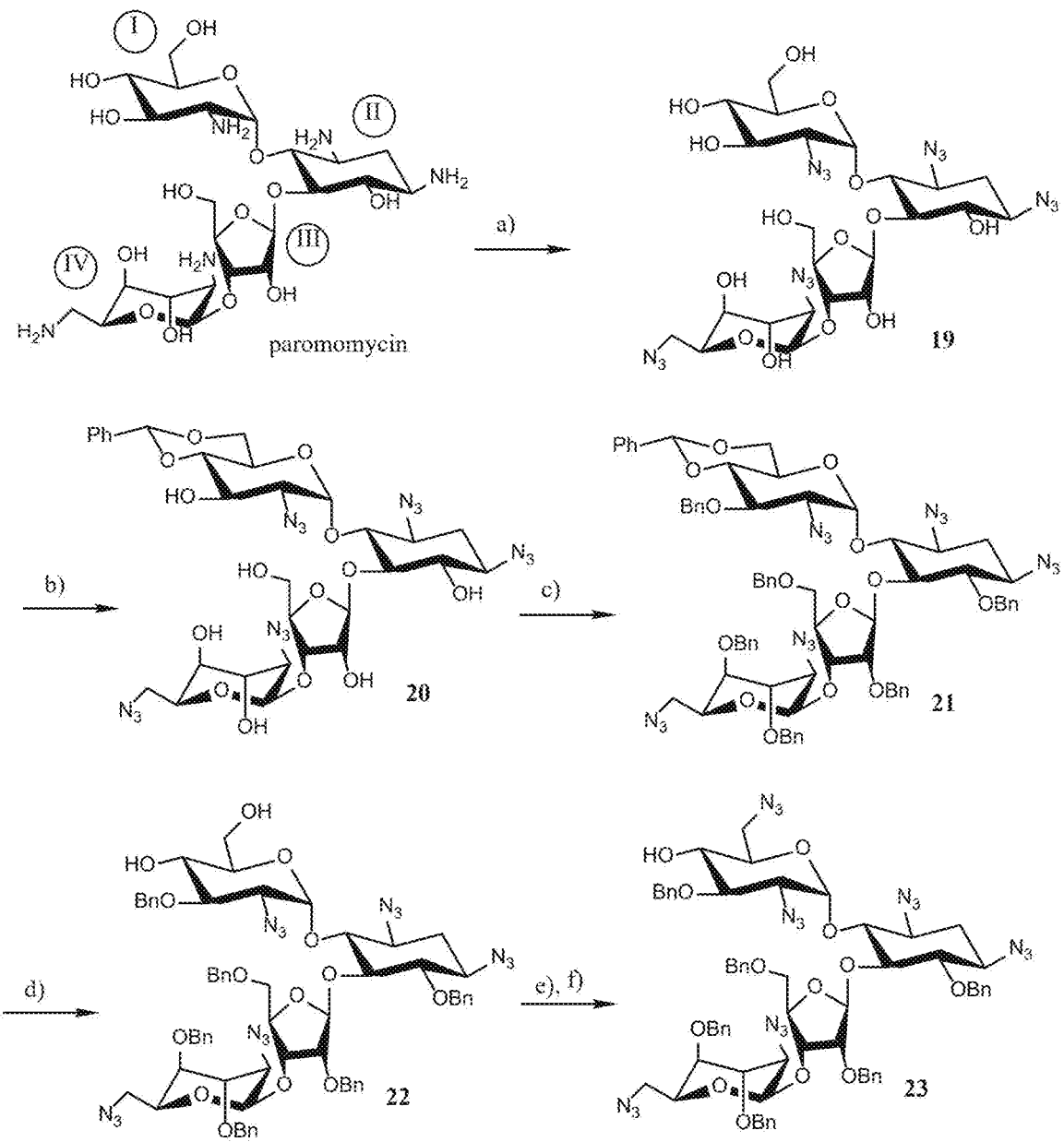

FIG. 2B is a scheme showing an exemplary synthetic pathway for preparing Compounds 2-5. a) ImSO$_2$N$_3$·HCl, CuSO$_4$ (70%); b) PhCH(OMe)$_2$, CSA, DMF (88%); c) BnBr, NaH, DMF (60%); d) AcOH/H$_2$O (61%); e) Trisyl chloride, py; f) NaN$_3$, DMF (60%); g) allyl bromide, NaH, DMF (92%); h) K2OsO$_4$, NMO, acetone/H$_2$O (89%); i) PhI(OAc)$_2$, CH$_2$Cl$_2$; j) amines A, B, 1-(2-aminoethyl)pyrrolidine, C; k) NaBH(OAc)$_3$; l) trifluoroacetic acid, CH$_2$Cl$_2$; m) PMe$_3$, NaOH; n) Na/NH3, THF.

Figure 3:
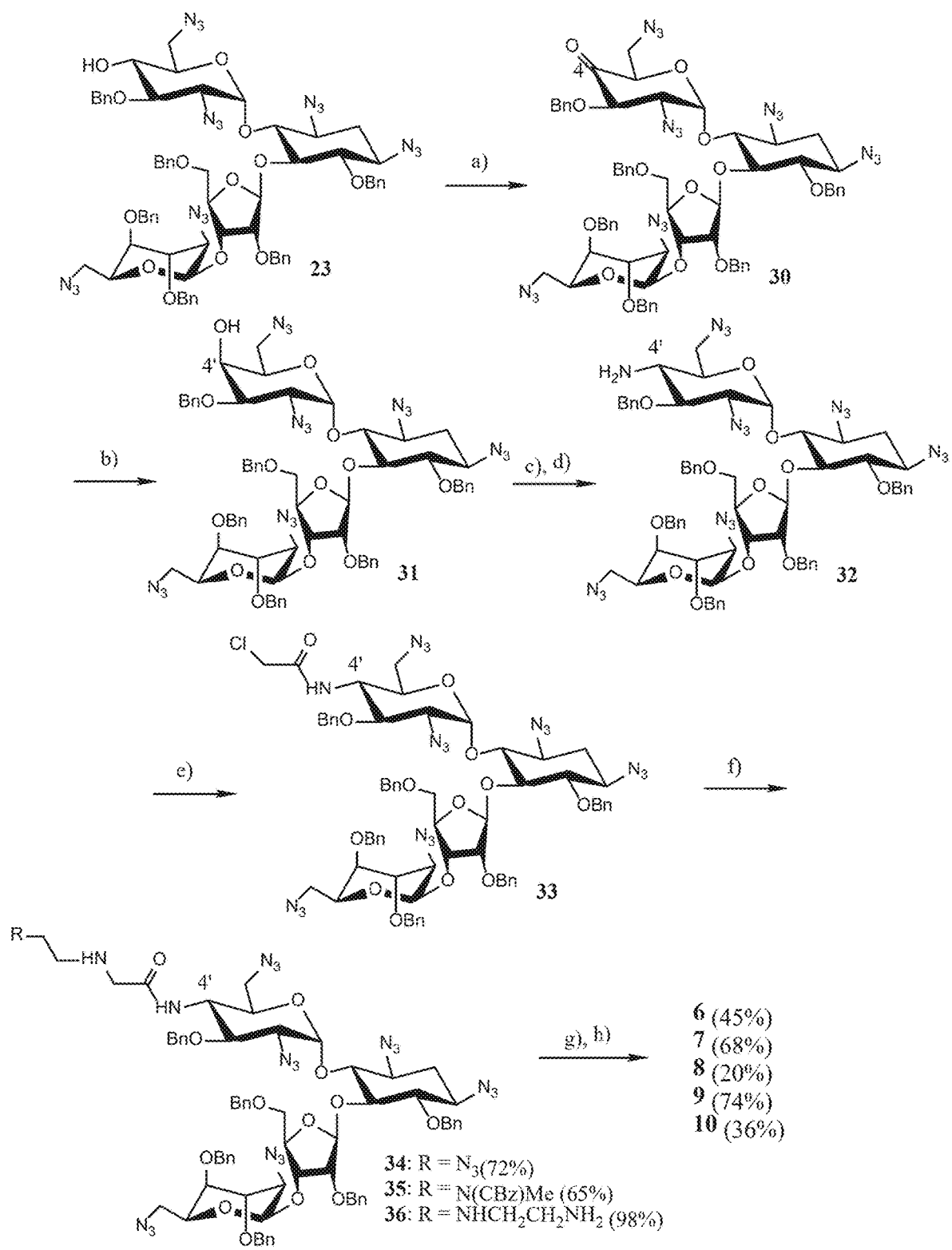

FIG. 3 is a scheme showing an exemplary synthetic pathway for preparing Compounds 6-10. a) DMP, CH$_2$Cl$_2$ (86%); b) NaBH$_4$, MeOH (82%); c) Tf$_2$O, py/CH$_2$Cl$_2$; d) acetone/NH$_3$ (41%); e) chloroacetyl chloride, NaHCO$_3$, THF (98%); f) amines A, B, diethylenetriamine; g) PMe$_3$, NaOH; h) Na/NH$_3$, THF; CBz=benzyloxycarbonyl.

Figure 4A:
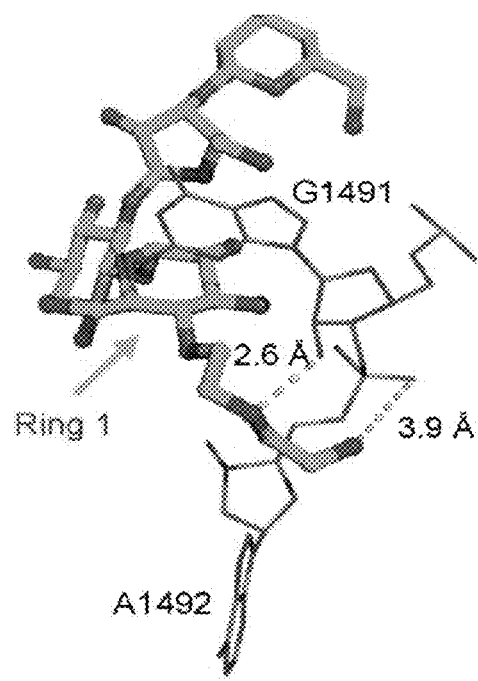
Figure 4B:
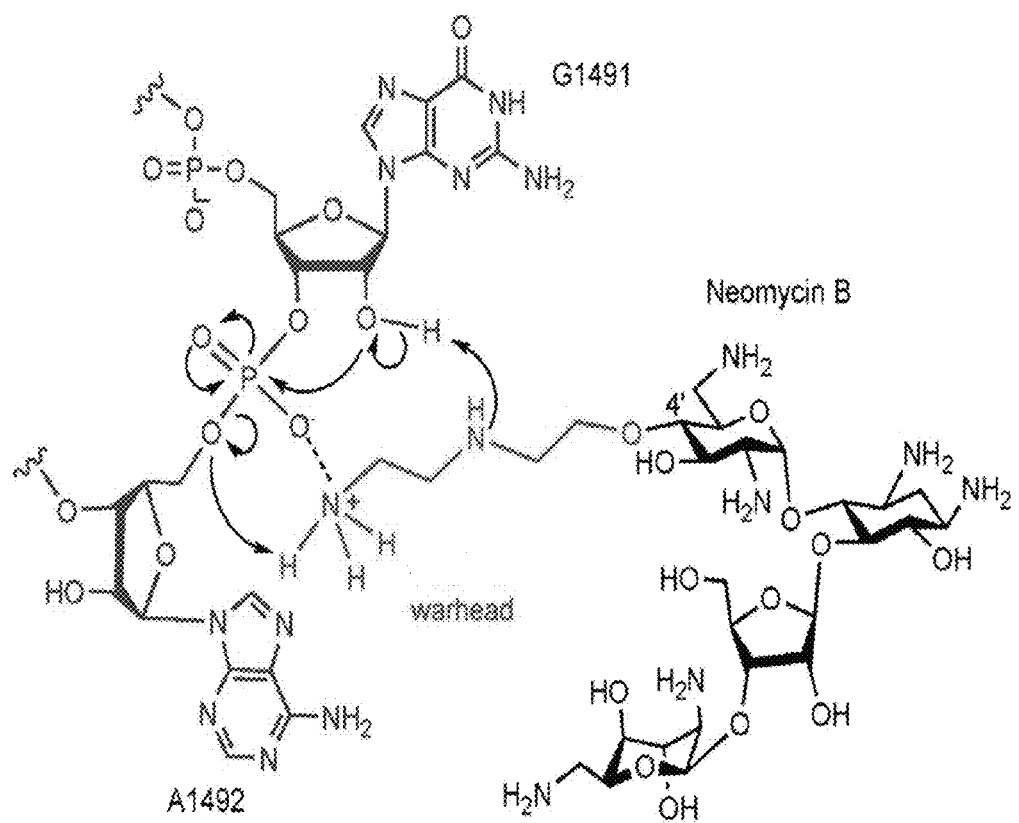

FIGS. 4A-B present a ball-and-stick representation of Compound 2-induced cleavage site in the bacterial rRNA A-site. Modeling was performed by superimposition of Compound 2 with the NeoB structure in the crystal structure of NeoB bound to the rRNA oligonucleotide model (PDB ID: 2ET4), having SEQ ID NO: 3, by using PyMOL (FIG. 4A) and a schematic illustration of a proposed action of compound 2 on the hydrolysis of the phosphodiester bond between G1491 and A1492 (FIG. 4B).

FIG. 5 presents Table 1 showing comparative antibacterial activity (MIC values) and inhibition of protein translation (IC50 values) in the prokaryotic system of NeoB and exemplary Compounds 1-10.

FIGS. 6A, 6B, 6C and 6D presents the data obtained in cleavage experiments of E. coli ribosomes in the presence of ethylenediamine, colicin E3, NeoB, and Compound 3. FIG. 6A, Lane 1: E. coli ribosomes (control); lanes 2-5: ribosomes treated with increasing concentrations of ethylenediamine. FIG. 6B, Lane 1: control; lanes 2-6: ribosomes treated with decreased concentrations of colicin E3. FIG. 6C, Lane 1: control; lane 2: ribosomes treated with 7.3 mm colicin E3 (ColE3); lanes 3-6: ribosomes treated with increasing concentrations of NeoB. FIG. 6D, Lane 1: control; lanes 2-4: ribosomes treated with increasing concentrations of Compound 3. rRNA fragments were analyzed on 6% acrylamide TBE/urea gel, stained with SYBR Gold and were analyzed by fluorescence.

FIGS. 7A-B present a two dimensional representation of the double-A site oligonucleotide model containing two identical binding sites of aminoglycosides, site I and site II, each having SEQ NO. 2 (FIG. 7A), showing the attachment sites of the fluorescent tag at the 3'-end; and the sequence of RNA containing 23 bases with the covalently attached fluorescent tag, Cy3 (as purchased from Dharmacon Ltd.), having SEQ ID NO:3 (FIG. 7B). The structure of Cy3 and the cleavage sites of colicin E3 toxin (between A1493 and G1494) along with the proposed cleavage site of the designer aminoglycosides (between G1491 and A1492) are shown.

FIGS. 8A-B presents the data obtained in cleavage experiments of the A-site oligonucleotide model rRNA (SEQ ID NO: 1), incubated for 24 hours, pH 8, 37° C. in the presence of ethylenediamine and Compound 6. FIG. 8A, Lane 1: RNA markers; lane 2: blank lane; lane 3: not treated (control); lanes 4-7: rRNA oligonucleotide treated with increased concentrations of ethylenediamine. FIG. 8B, Lane 1: RNA markers; lanes 2-7: rRNA oligonucleotide treated with increased concentrations of compound 6; lanes 8 and 9: rRNA oligonucleotide treated with 500 mm 1,2-cyclohexanediamine (Cyclo) and ethylenediamine (N2N), respectively; lane 10: not treated (control). rRNA fragments were analyzed on 20% TBE/urea gel and were visualized by fluorescence. DS: double-stranded rRNA; SS: single-stranded rRNA.

Figure 9:
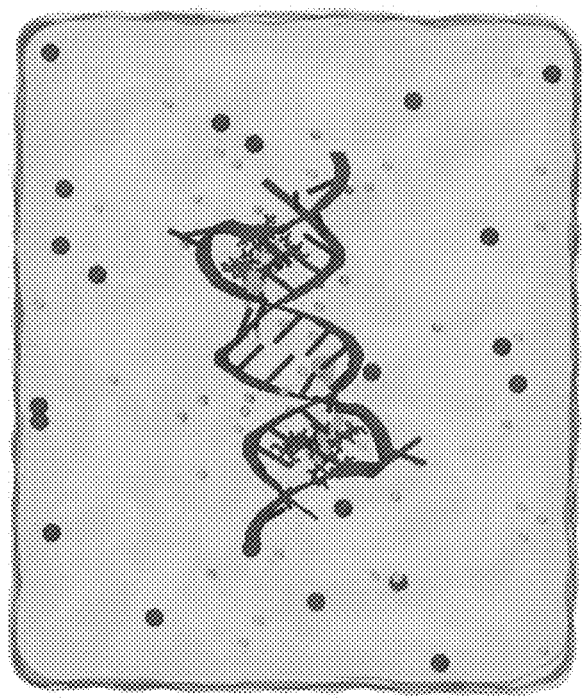

FIG. 9 presents a simulated system used in the MD simulations described I Example 5, which is composed of RNA (shown in red), aminoglycoside (green), water (blue surface), sodium (yellow), and chloride ions (purple).

Figure 10:
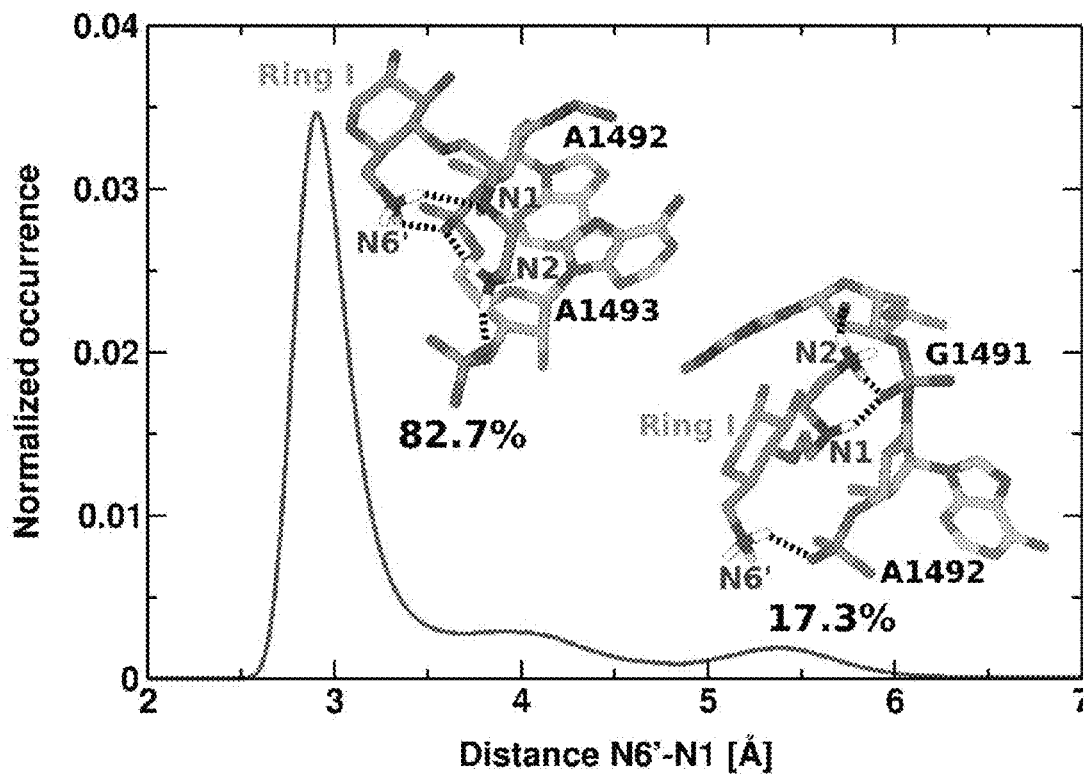

FIG. 10 presents the normalized occurrence of the two conformational states of Compound 2 warhead as a function of the intramolecular distance between the N6' ammonium of ring I and the N1 amine of the warhead. The representative structures are presented. For clarity, only ring I of the aminoglycoside (green) and hydrogen atoms crucial for the interactions of the warhead are shown. Black dashed lines denote donor-acceptor short-range interactions.

Figure 11:
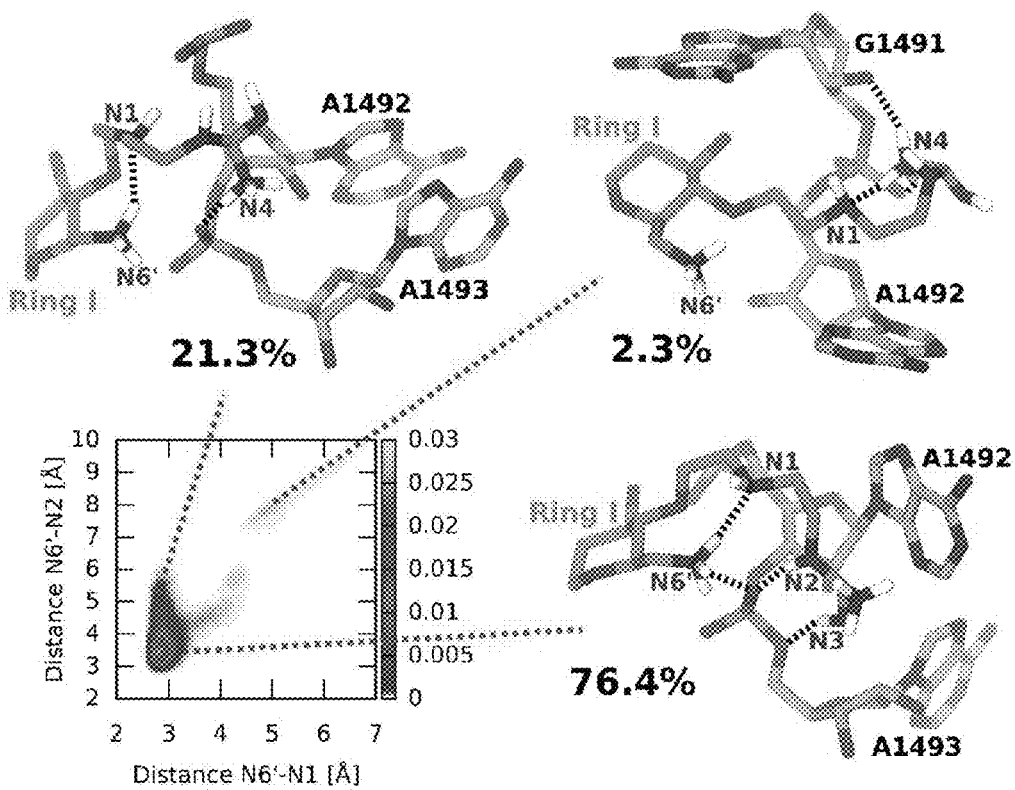
Figure 12A:
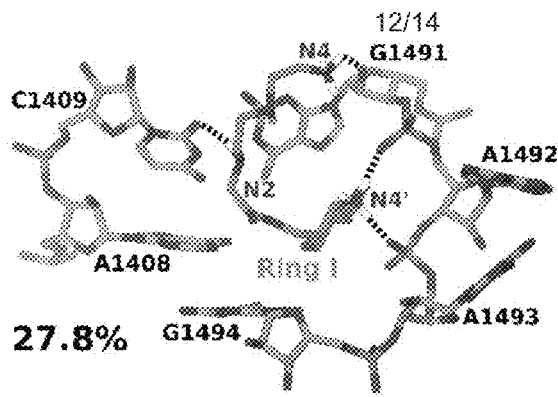
Figure 12B:
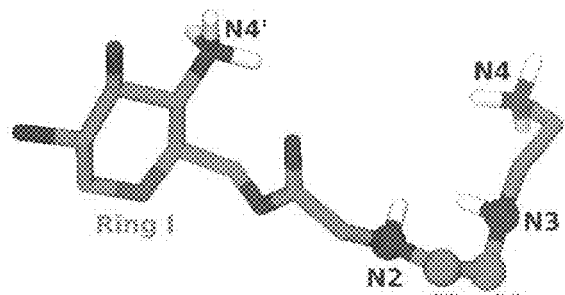
Figure 12C:
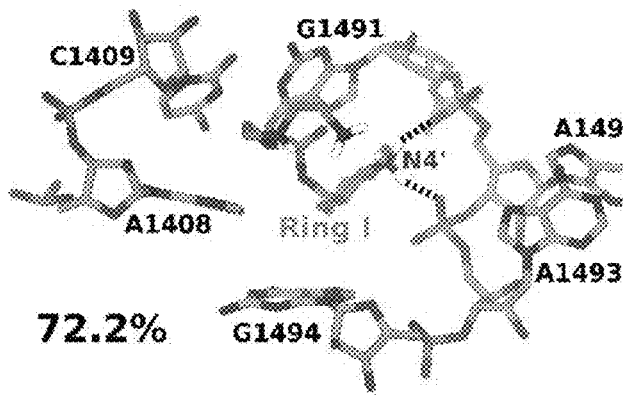
Figure 12D:
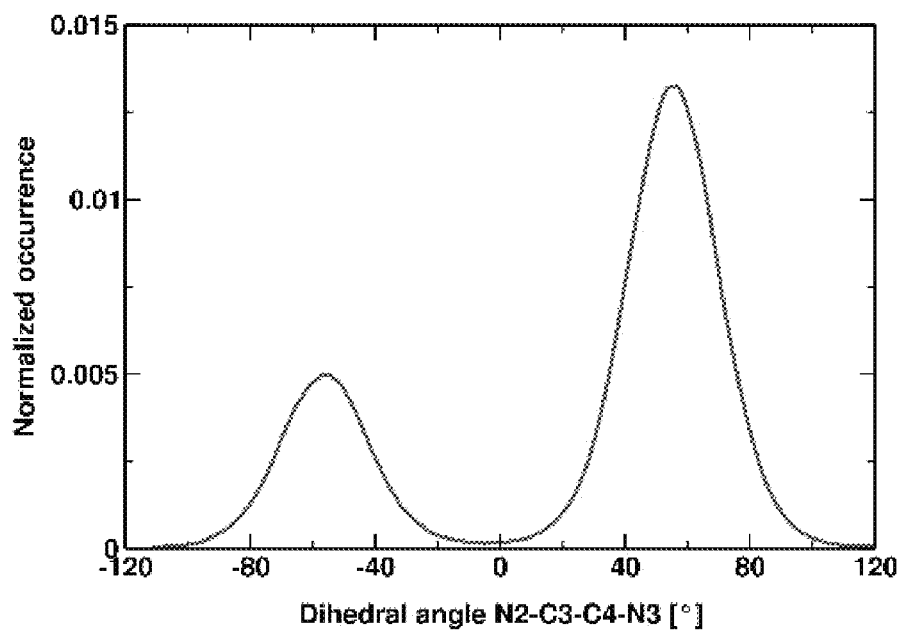

FIG. 11 presents the normalized occurrence of the three conformational states of Compound 5 warhead as a function of two intramolecular distances N6'—N1 and N6'—N2. The representative structures are presented. For clarity, only ring I of the aminoglycoside (green) and hydrogen atoms crucial for the interactions of the warhead are shown. Black dashed lines denote donor-acceptor short-range interactions FIGS. 12A, 12B, 12C and 12D present the normalized occurrence of the two conformational states of Compound 10 warhead as a function of the dihedral angle N2-C3-C4—N3 (FIG. 12D). The representative structures are presented (FIG. 12A and FIG. 12c). For clarity, only ring I of the aminoglycoside (green) and hydrogen atoms crucial for the interactions of the warhead are shown (FIG. 12B). Black dashed lines denote donor-acceptor short-range interactions.

Figure 13:
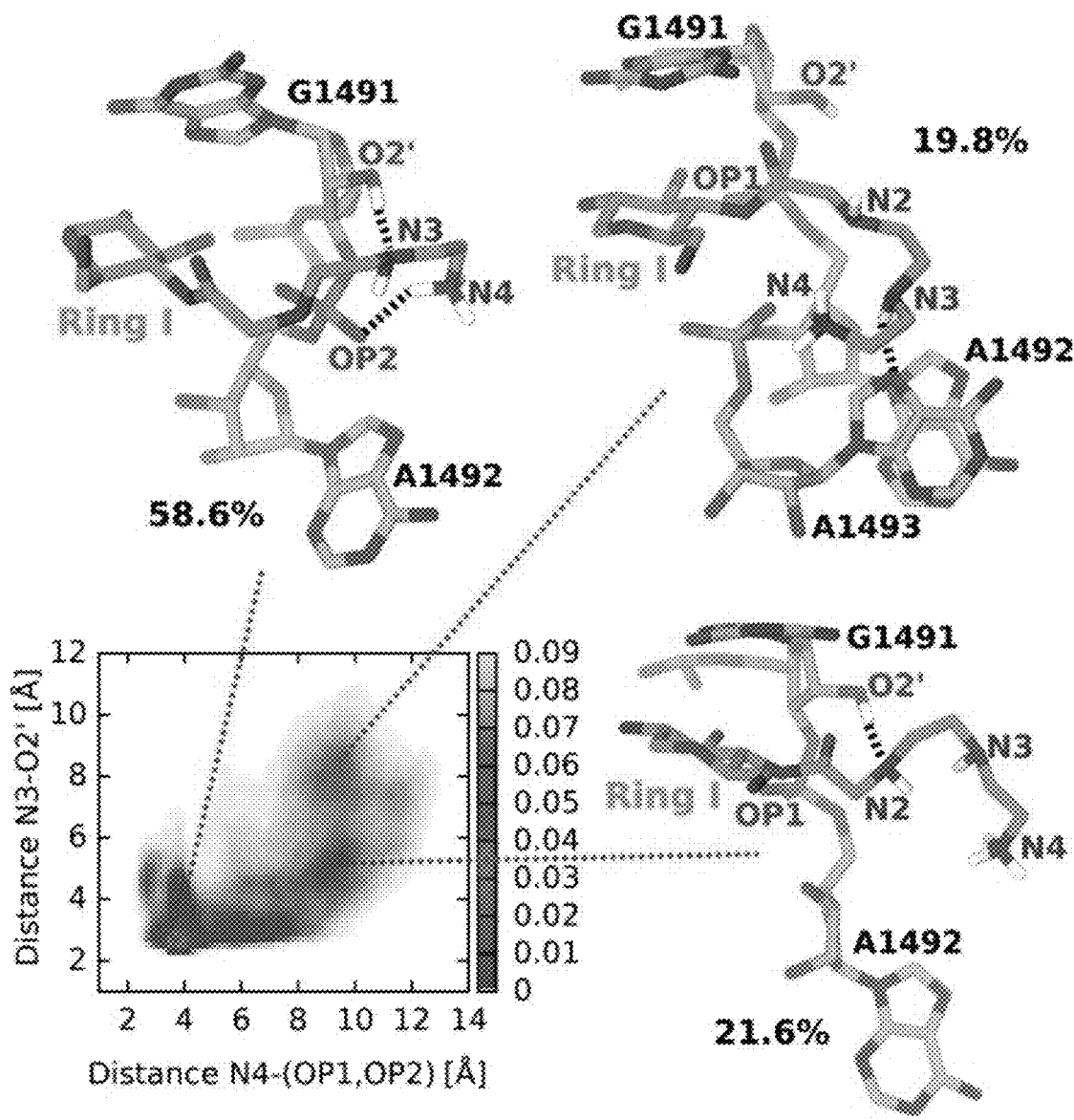

FIG. 13 presents the normalized occurrence of the three binding modes of Compound 8 warhead to A-site as a function of the two intermolecular distances N3-O2' and N4-(OP1, OP2). The representative structures are presented. For clarity, only ring I of the aminoglycoside (in green) and hydrogen atoms crucial for interactions of the warhead are shown. Black dashed lines denote donor-acceptor short-range interactions.

Figure 14:
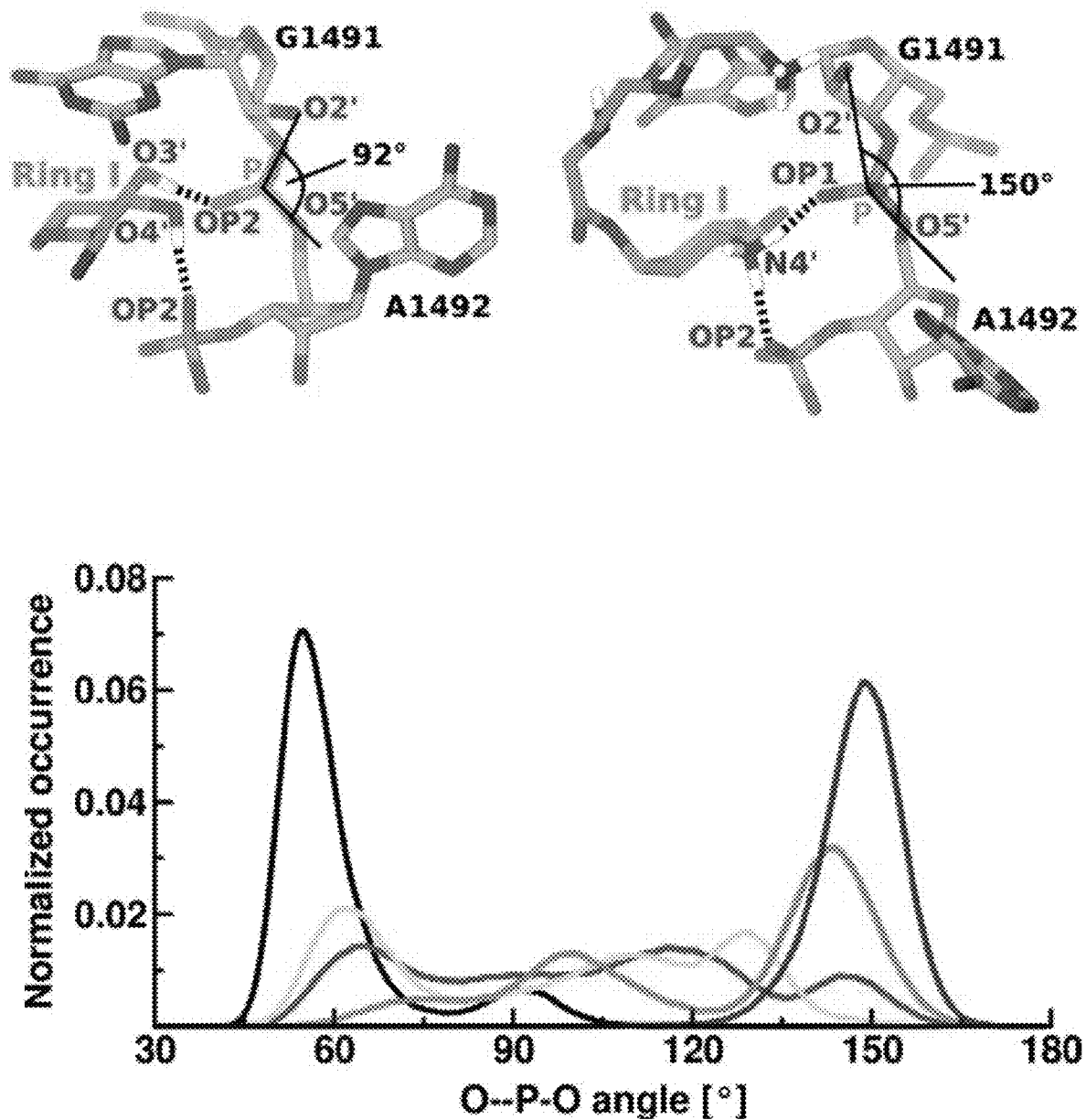

FIG. 14 presents the distributions of the O—P—O angle for NeoB (black) and Compounds 2 (red), 5 (yellow), 8 (green), and 10 (blue) in GaMD simulations. Above is shown the O—P—O angle in the representative structures of NeoB (left) and compound 10 (right). The donor-acceptor short-range interactions important for stabilization of the O—P—O angle are marked by black dashed lines. For clarity, only ring I of the aminoglycosides (in green) and selected hydrogen atoms are shown.

DESCRIPTION OF SPECIFIC EMBODIMENTS OF THE INVENTION

The present invention, in some embodiments thereof, relates to aminoglycosides and, more particularly, but not exclusively, to newly designed aminoglycoside compounds which are aimed at disabling bacterial ribosome and are usable in treating diseases and disorders associated with a pathogenic microorganism such as pathogenic bacteria, including drug-resistant bacterial strains.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have designed and successfully synthesized and practiced a series of new derivatives of the natural aminoglycoside antibiotics.

The newly designed aminoglycoside derivatives (which are also referred to herein as "modified aminoglycosides") were designed while considering structural and mechanistic data on the bacteriocin ColE3 and on aminoglycoside antibiotics.

The modified aminoglycosides were designed while aiming at mimicking the interactions of ColE3 with the prokaryotic rRNA (ribosomal RNA) decoding site.

The design principles included a choice of the "target" phosphodiester bond in the prokaryotic rRNA decoding site, the chemical structure of the functional moiety that is aimed at interacting with the target position in the prokaryotic rRNA, which is also referred to herein as the "warhead", and the attachment site of this functional moiety on the aminoglycoside scaffold. As the target bond, the phosphodiester bond between the rRNA bases G1491 and A1492 was selected as the potential cleavage site and the 4', 3' and/or 6' positions (ring I) of the natural aminoglycoside were selected as attachment site(s) for the functional moieties (warheads). As the functional moiety, a series of different moieties that feature two or more amines or amine-containing groups (also referred to herein as "diamine-containing functional moiety") was used.

In one subset of newly designed compounds, modifications were made to the natural aminoglycoside NeoB or the disaccharide core neamine, while attaching different diamine-containing moieties to the 4'-OH position (see, Compounds 1-5, FIG. 1). In another subset modifications were made to the natural aminoglycoside NeoB while attaching different diamine-containing moieties directly to the 4' position (see, Compounds 6-8, FIG. 1). In another subset modifications were made to the natural aminoglycoside NeoB, while attaching different diamine-containing moieties to the 6' position (see, Compounds 9 and 10, FIG. 1).

All these compounds were successfully synthesized, using the synthetic pathways shown in FIGS. 2A, 2B and 3.

The suggested interaction of such an exemplary compound, Compound 2, with the A-site of a prokaryotic rRNA (e.g., having SEQ ID NO:3) is presented in FIGS. 4A-B, and provides insights on the required configuration of a modified aminoglycoside for providing an interaction that would disable the ribosome.

The new derivatives showed significant antibacterial activity against wild-type strains of both Gram-negative and Gram-positive bacteria and display significantly improved activity (compared to NeoB) against highly aminoglycoside-resistant strains and pathogenic strains, and exhibited inhibition of protein synthesis, as shown in Table 1, presented in FIG. 5.

The observed anti-bacterial activity indicates that the modifications on NeoB did not hinder bacterial cell permeability or the binding affinity of the aminoglycoside scaffold to the target site.

Some compounds displayed hydrolytic RNase activity, as shown in FIGS. 6B, 6C, 6D, 7A, 7B, 8A, 8B.

FIGS. 9, 10, 11, 12A, 12B, 12C, 12D, 13, 14 present full-atom GaMD simulations on the crystal structure of NeoB bound to the oligonucleotide model of the A-site rRNA (according to PDB ID: 2ET4; see, SEQ ID NO:3). These data provide additional information on the conformational states of the diamine-containing functional moieties when interacted with the selected prokaryotic rRNA decoding site, and on the resulting change in the O—P—O angle of the phosphodiester bond linking A1492 and G1491 of the selected model, which can lead to its activation towards cleavage and/or to disabling of the ribosome activity.

Embodiments of the present invention relate to newly designed aminoglycosides that are aimed at interacting with a prokaryotic rRNA decoding site (A-site) to thereby disable the bacterial ribosome, to processes of preparing such compounds and to uses thereof in the treatment of medical conditions associated with pathogenic microorganisms.

Herein, the phrase "prokaryotic rRNA decoding site" refers to a typically conserved site of a prokaryotic ribosomal RNA which is also known in the art as the A-site of the rRNA. In some embodiments, this phrase refers to the 16S unit of the ribosomal RNA that comprises SEQ ID NO:2 or 3. In some embodiments, an interaction of the aminoglycoside compounds of the present embodiments, and of aminoglycoside compounds in general (e.g., anti-bacterial aminoglycosides), relates to the sequence of the 5 nucleotides between G1491 and G1494, which is referred to herein as the aminoglycosides binding site in prokaryotic ribosomal RNA.

Modified Aminoglycosides:

According to some embodiments of the present invention there are provided newly designed compounds, which are also referred to herein as aminoglycoside derivatives or as modified aminoglycosides.

According to some embodiments of the present invention, the newly designed aminoglycoside compounds feature a di-, tri-, or tetra-pseudosaccharide structure, and one or more di-functional moiety or moieties, e.g., diamine-containing functional moiety/moieties, attached to one or more positions of Ring I of the aminoglycoside. The functional moiety/moieties are such that when interacting with the prokaryotic rRNA A-site, a change in the O—P—O angle of at least one phosphodiester bond in the aminoglycoside binding site of a prokaryotic ribosomal RNA, which is typically from G1491 to G1494, occurs. The one or more phosphodiester bonds in which a change in O—P—O angle occurs can be any such bond that links any adjacent oligonucleotides in the above mentioned rRNA A-site sequence, preferably in the above-mentioned aminoglycoside binding site, and in some embodiments it is the bond between G1491 and A1492. In some embodiments the change in O—P—O angle results in an angle that is higher than 100°, higher than 120°, higher than 140°, or preferably higher than 150°, and even higher (e.g., the closest to 180°).

In some embodiments, the O—P—O angle of this phosphodiester bond is such that facilitates a nucleophilic attack of one of the amine-containing groups (a basic group), that is further activated by another amine-containing group (an acidic group), which may lead to cleavage of the phosphodiester bond.

In some embodiments, the di-functional moiety is such that features at least one acidic amine-containing group, as defined herein, and at least one basic amine-containing group, as defined herein, and at least one linking group that links these groups to one another. In some embodiments, an intramolecular distance and/or the conformational variability between these acidic and basic groups is such that when the compound interacts with a prokaryotic rRNA A-site, the basic amine-containing group is capable of interacting with the 2'-hydroxy group of the ribose of one oligonucleotide in the aminoglycoside binding site, e.g., G1491, and the acidic amine-containing group is capable of interacting with the phosphate group of an adjacent oligonucleotide in the aminoglycoside binding site, e.g., A1492 and may also be capable to donate proton to the 5'-oxygen of the phosphate linkage.

In some embodiments, the functional moiety is such that features at least one acidic amine-containing group, as defined herein, and at least one basic amine-containing group, as defined herein, and a linking group that links these groups to one another, and an intramolecular distance and/or the conformational variability between the basic and acidic groups is such that when the compound interacts with a prokaryotic rRNA A-site, the basic amine-containing group is capable of interacting with the 2'-hydroxy group of the ribose of one nucleotide as described herein (e.g., G1491), and the acidic amine-containing group is capable of interacting with the phosphate group of an adjacent oligonucleotide (e.g., A1492), as described herein, and optionally also of A1493, and these interactions result in an O—P—O angle of the phosphodiester bond between these adjacent oligonucleotides (e.g., G1491 and A1492) which is higher than 100°, higher than 120°, higher than 140°, or higher than 150°, as described herein.

Herein throughout, an "amine-containing group" describes a chemical group that comprises or consists of at least one —NR'— or —NR'R" group, with R' and R" is each independently hydrogen, alkyl, or cycloalkyl, or R' and R" form together a heterocyclic (e.g., alicyclic) group, or as defined hereinafter.

An amine-containing group can be —NR'— or —NR'R" group per se (e.g., —NH— or —NH$_2$), as defined herein, or a protonated (ammonium) form thereof, that is, —N$^+$R'R"— or —N$^+$R'R"R"'—, with R"' being as defined for R' and R" (e.g., —N$^+$H$_2$— or —N$^+$H$_3$). Preferably R"' is hydrogen. Preferably, at least one of R', R" and R"' is hydrogen.

An amine-containing group can alternatively be a chemical group that comprises one or more —NR'— or —NR'R" group(s) as defined herein, or a protonated or ammonium form thereof, as defined herein, as part of a larger group that comprises additional chemical groups. Examples of such groups include, without limitation, amide, thioamide, guanyl, guanidyl, carbamate, thiocarbamate, hydrazine, hydrazide, thiohydrazide, urea, and thiourea. In some embodiments, such groups include amide, guanyl, guanidyl, and hydrazine.

A basic amine-containing group, as used herein, generally describes a nucleophilic amine-containing group, or a group which, at a physiological pH and/or environment, can function as a proton acceptor group, and which can be in a protonated at a physiological pH and/or a physiological environment. In some embodiments, a basic amine-containing group features pKa higher than 8, or higher than 9.

An acidic amine-containing group, as used herein, generally describes an electrophilic amine-containing group, or a group which, at a physiological pH and/or environment, can function as a proton donor. In some embodiments, an acidic amine-containing group features pKa that is lower from that of the basic amine-containing group by at least 1 pKa unit, for example, by 1, 1.2, 1.4, 1.5, 1.6, 1.8, 2, and even more.

In some embodiments, an acidic amine-containing group is or comprises a positively charged ammonium group that can act as a proton donor, e.g., is protonated at physiological pH, for example, a —N$^+$R'R"— or —N$^+$R'R"R"'— group in which at least one of R', R" and R"' (if present) is hydrogen.

In some embodiments, a diamine-containing moiety is such that comprises at least two amine-containing groups as described herein and a linking group that links these groups, and the amine-containing groups and the linking group are such that in a physiological environment (e.g., pH), one of the amine-containing group is protonated (and functions as an acidic group, or a proton donor, or an electrophile) and the other amine-containing group is not protonated (and functions as a basic group or a proton acceptor or a nucleophile).

In some embodiments, a diamine-containing moiety is such that comprises at least two amine-containing groups as described herein and a linking group that links these groups, and the amine-containing groups and the linking group are such that in a physiological environment (e.g., pH), a difference in the pKa of amine-containing groups is at least 1 pKa unit, as described herein.

It is to be noted that when reference is made to a protonated group, it is meant that an abundance of such a protonated form at a physiological pH (pH of about 7) is more than 5%, or more than 10%, or more than 20%, or more than 30%, or more than 40%, or more than 50%.

According to some of any of the embodiments described herein, the modified aminoglycosides can be collectively represented by Formula I:

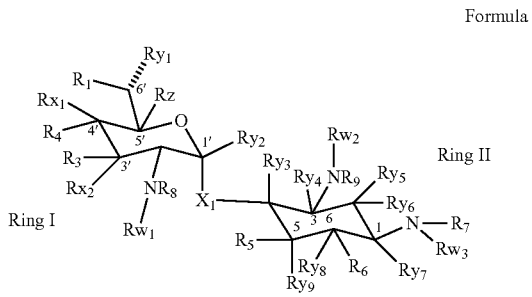

Formula I or a pharmaceutically acceptable salt thereof,
wherein:
the dashed line indicates a stereo-configuration of position 6' being an R configuration or an S configuration;
$X_1$ is O or S;
Rx1, Rx2, Ry1 and Rz are each independently selected from hydrogen, alkyl and cycloalkyl;
Ry2-Ry9 and Rw1-Rw3 are each independently selected from hydrogen, alkyl, and cycloalkyl;
$R_1$, $R_3$ and $R_4$ are each independently $NR_{23}R_{24}$, $OR_{20}$ or a diamine-containing moiety, wherein $R_{20}$ is hydrogen, alkyl, cycloalkyl or the diamine-containing moiety, and each of $R_{23}$ and $R_{24}$ is independently hydrogen, alkyl, cycloalkyl or acyl, provided that at least one of $R_1$, $R_3$ and $R_4$ is or comprises the diamine-containing moiety;
$R_5$ and $R_6$ are each independently selected from hydrogen, alkyl, alkenyl, alkynyl, cycloalkyl, heteroalicyclic, aryl, heteroaryl and $OR_{16}$, wherein $R_{16}$ is independently selected from hydrogen, a monosaccharide moiety and an oligosaccharide moiety; and
$R_7$-$R_9$ are each independently selected from the group consisting of hydrogen and acyl,
wherein the diamine-containing moiety comprises at least two amine-containing groups, as described herein in any of the respective embodiments, and at least one linking group, as described herein in any of the respective embodiments, linking the at least two amine-containing groups.

According to some of any of the embodiments described herein, the at least two amine-containing groups and the at least one linking group are arranged such that:

(i) a difference in the pKa of at least two of the amine-containing groups is at least 1; and/or
(ii) when the compound is in a physiological environment, at least one of the amine-containing groups is protonated at physiological pH while at least another of the amine-containing groups is non-protonated; and/or
(iii) when the compound interacts with a prokaryotic ribosomal RNA decoding site (A-site), the RNA undergoes a conformational change such that an O—P—O angle of at least one phosphodiester bond is higher than 100°; and/or
(iv) when the compound interacts with a prokaryotic ribosomal RNA decoding site (A-site) (e.g., comprising SEQ ID NO:2 or 3), the functional moiety is capable of adopting a configuration in which one of the amine-containing groups is in close proximity and suitable orientation so as to interact with a 2'-OH group of a ribose of a nucleotide in the RNA and another amine-containing moiety is in close proximity and suitable orientation so as to interact with a phosphate group of a nucleotide of an adjacent nucleotide.

According to some of any of the embodiments described herein, the at least two amine-containing groups and the at least one linking group are arranged such that any two, any three or all of (i), (ii), (iii) and (iv) as described herein are fulfilled.

According to some of any of the embodiments described herein, the at least two amine-containing groups and the at least one linking group are arranged such that a difference in the pKa of at least two of the amine-containing groups is at least 1, as described herein in any of the respective embodiments.

It is to be noted that two identical amine-containing groups within the same can feature different pKa values, due to intramolecular electrostatic interactions between one another and/or between each of these groups with other groups in the compound, and/or due to intermolecular electrostatic interactions with a surrounding environment (e.g., physiological environment and/or interaction with the rRNA as described herein).

According to some of any of the embodiments described herein, the at least two amine-containing groups and the at least one linking group are arranged such that when the compound is in a physiological environment, at least one of the amine-containing groups is protonated at physiological pH, as described herein in any of the respective embodiments, while at least another of the amine-containing groups is non-protonated, as described herein in any of the respective embodiments. The physiological environment can be a physiological pH and/or a presence of additional physiological salts and/or interaction with the rRNA as described herein.

According to some of any of the embodiments described herein, the at least two amine-containing groups and the at least one linking group are arranged such that when the compound interacts with a prokaryotic ribosomal RNA decoding site (A-site) as described herein (e.g., comprising SEQ ID NO:2 or 3), the RNA undergoes a conformational change such that an O—P—O angle of at least one phosphodiester bond within said site is higher than 100°, as described herein in any of the respective embodiments. See, for example, FIG. 14.

According to some of these embodiments, when the compound interacts with the prokaryotic rRNA A-site as described herein, the diamine-containing functional moiety adopts a configuration, presumably upon the interactions formed between the amine-containing groups and chemically compatible groups in the RNA A-site, e.g., as described herein, which leads to the above-indicated conformational change of the RNA.

In some of these embodiments, the O—P—O is determined by MD simulations as described herein in the Examples section that follows, using structural conformations with respect to prokaryotic rRNA portion having SEQ ID NO:3 or 2.

According to some of these embodiments, the phosphodiester bond is one or more of the phosphodiester bonds within the nucleotide sequence G1491-G1494 of the rRNA portion as described herein, e.g., the rRNA comprising the oligonucleotide sequence having SEQ ID NO:3 or 2.

According to some of these embodiments, the phosphodiester bond is between G1491 and A1492 of the rRNA as described herein, e.g., the rRNA comprising the oligonucleotide sequence having SEQ ID NO:3 or 2.

According to some of any of the embodiments described herein, the at least two amine-containing groups and the at least one linking group are arranged such that when the compound interacts with a prokaryotic ribosomal RNA decoding site (A-site) as described herein, the functional moiety is capable of adopting a configuration in which one of the amine-containing groups is in close proximity and suitable orientation so as to interact with a 2'—OH group of a ribose of a nucleotide in the RNA and another amine-containing moiety is in close proximity and suitable orientation so as to interact with a phosphate group of a nucleotide of an adjacent nucleotide.

Herein throughout, by "proximity and orientation" it is meant that an indicated group or moiety is sufficiently close and properly oriented so as to strongly interact with a respective group (chemically compatible group) in the indicated binding site (the prokaryotic rRNA A-site, preferably the aminoglycoside binding site therein).

By "interacting" or "interact", in the context of groups or moieties in a compound as described herein and a respective moiety in the rRNA, it is meant a chemical interaction as a result of, for example, non-covalent interactions such as, but not limited to, electrostatic interactions, Van der Waals interactions and/or hydrogen bonding.

In some embodiments, the indicated close proximity and orientation of the functional moiety result from the spatial arrangement of the amine-containing groups, when the compound contacts the respective rRNA binding site, and the partial charge of each of these groups that allows interaction with the respective indicated groups in the rRNA binding site. The spatial arrangement can depend, for example, on the conformational variability of the functional moiety.

In some of any of these embodiments, the proximity and orientation of the amine-containing groups is determined by means of crystallographic models, in silico modeling and/or MD simulations, as described herein in the Examples section that follows. In some of these embodiments, the proximity and orientation is determined using such models for structural conformations of the compound with respect to prokaryotic rRNA oligonucleotide sequence portion having SEQ ID NO:3 or 2.

According to some of these embodiments, the phosphodiester bond is one or more of the phosphodiester bonds within the nucleotide sequence G1491-G1494 of the rRNA, e.g., the rRNA portion comprising the oligonucleotide sequence having SEQ ID NO:3 or 2.

In some of any of these embodiments, in any of the above-indicated models, the distance between the amine-containing group that interacts with the 2'—OH group of the indicated ribose is no more than 4 angstroms, or no more than 3.5 angstroms, or no more than 3 angstroms, and can be, for example, from 1 to 4, or from 2 to 4, or from 2 to 3.5, or from 2.5 to 2.5, angstroms. Such amine-containing group is a "basic" amine group, as described herein, which is non-protonated in physiological environment (e.g., physiological pH) and/or can act as a nucleophile and/or as a proton acceptor.

In some of any of these embodiments, in any of the above-indicated models, the distance between the amine-containing group that interacts with the indicated phosphate group, and the phosphate group is no more than 5 angstroms, or no more than 4.5 angstroms, or no more than 4 angstroms, and can be, for example, from 1 to 5, or from 2 to 5, or from 2 to 4, or from 3 to 4, angstroms. Such amine-containing group is an "acidic" amine group, as described herein, which is protonated in physiological environment (e.g., physiological pH), as defined herein, and/or can act as a proton donor and/or as an electrophile.

The amine-containing group that interacts with the indicated phosphate group typically interacts with one or both of the oxygen atoms of the phosphate group.

According to some of these embodiments, the 2'—OH group of the ribose is of the G1491 nucleotide and the phosphate is of the adjacent A1492 nucleotide of the rRNA, e.g., the rRNA portion comprising the oligonucleotide sequence having SEQ ID NO:3 or 2.

In some of any of the embodiments described herein, the proximity and orientation of the amine-containing groups towards the 2'—OH group of the indicated ribose the indicated phosphate group results in the conformational change of the rRNA as described herein, e.g., in a O—P—O angle of the phosphodiester bond as described herein in any of the respective embodiments.

According to some of any of the embodiments described herein, the diamine-containing functional moiety can be represented by the following Formula:

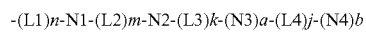

wherein:
each of L1, L2, L3 and L4 is independently a linking group, as described herein in any of the respective embodiments, whereby when two or more linking groups are present, they can be the same or different;
each of N1, N2, N3 and N4 is an amine-containing group, as described herein in any of the respective embodiments; and
each of a, b, n, m, k, and j is independently 0 or 1.

In some of any of the embodiments described herein, at least one of the linking groups, or each of the linking groups, in case there are two or more linking groups, is independently a hydrocarbon group being of 1 to 6 carbon atoms in length.

Preferably, the hydrocarbon is a linear, aliphatic and non-branched hydrocarbon, and further preferably it is unsubstituted.

In some of any of the embodiments described herein, at least one of the linking groups, or each of the linking groups, in case there are two or more linking groups, is independently an alkylene chain being of 1 to 6, or of 1 to 4, or of 2 or 3, carbon atoms in length. Preferably, the alkylene chain is non-branched and unsubstituted.

Exemplary diamine-containing functional groups include, but are not limited to, moieties that consist of or comprise at least one of an ethylene diamine moiety, a methyl ethylene-diamine moiety, a diethylenetriamine moiety, an N-(2-aminoethyl)pyrrolidone moiety, and a guanidine-ethyleneamine moiety.

In some of any of the embodiments described herein, the compound comprises one diamine-containing functional moiety.

In some of any of the embodiments described herein, $R_4$ is or comprises the diamine-containing moiety, such that this moiety is at the 4' position of the aminoglycoside.

In some of these embodiments, $R_4$ is $OR_{20}$ and $R_{20}$ is a diamine-containing moiety as described herein in any of the respective embodiments and any combination thereof.

In exemplary embodiments, $R_{20}$ is

-(L1)n-N1-(L2)m-N2 wherein:

n and m are each 1;

L1 and L2 are each independently an alkylene of 1, 2 or 3, preferably 2 or 3, carbon atoms in length; and N1 and N2 are each independently selected from amine and guanidyl.

Exemplary such compounds include Compounds 1-5 as shown in FIG. 1 and hereinafter.

According to some of any of the embodiments described herein, $R_4$ is a diamine-containing moiety as described herein in any of the respective embodiments and any combination thereof.

In exemplary embodiments, $R_4$ is:

—N1-(L2)m-N2-(L3)k-(N3)

wherein:

m and k are each 1;

L2 and L3 are each independently an alkylene of 1, 2 or 3 carbon atoms in length;

N1 is amide; and each of N2 and N3 is independently an amine.

In some of these embodiments, L2 is an alkylene of 1 carbon atom in length (e.g., methylene). In some of any of these embodiments, L3 is an alkylene of 2 carbon atoms in length (e.g., ethylene).

Exemplary such compounds include Compounds 6 and 7 as shown in FIG. 1 and hereinafter.

In exemplary embodiments, $R_4$ is:

—N1-(L2)m-N2-(L3)k-(N3)a-(L4)j-(N4)b wherein:

m, k and j are each 1;

L2, L3 and L4 are each independently an alkylene of 1, 2 or 3 carbon atoms in length;

N1 is amide; and each of N2, N3 and N4 is independently an amine.

In some of these embodiments, L2 is an alkylene of 1 carbon atom in length (e.g., methylene). In some of any of these embodiments, L3 and L4 are each an alkylene of 2 carbon atoms in length (e.g., ethylene).

An exemplary such compound is Compound 8 as shown in FIG. 1 and hereinafter.

In some of any of the embodiments described herein, $R_1$ is or comprises the diamine-containing moiety.

In exemplary embodiments, $R_1$ is:

—N1-(L2)m-N2-(L3)k-(N3)a-(L4)j-(N4)b wherein:

m and k are each 1;

j is 0 or 1;

a is 1;

b is 0 or 1;

L2, L3 and L4, if present, are each independently an alkylene of 1, 2 or 3 carbon atoms in length;

N1 is amide; and each of N2, N3 and N4, if present, is independently an amine.

In some of these embodiments, L2 is an alkylene of 1 carbon atom in length (e.g., methylene). In some of any of these embodiments, L3 and L4, if present, are each an alkylene of 2 carbon atoms in length (e.g., ethylene).

In some of these embodiments, $R_4$ is $NR_{23}R_{24}$, as described herein, and in some of these embodiments each of $R_{23}$ and $R_{24}$ is hydrogen.

Exemplary such compounds are Compounds 9 and 10 as shown in FIG. 1 and hereinafter.

According to some of any of the embodiments described herein, X is O.

According to some of any of the embodiments described herein, the compound is a disaccharide, such that none of $R_5$ and $R_6$ is a monosaccharide or an oligosaccharide moiety. In some of these embodiments, each of $R_5$ and $R_6$ is $OR_{16}$, and in some embodiments $R_{16}$ is hydrogen.

According to some of any of the embodiments described herein, the compound is a tri-, tetra- or higher oligosaccharide, and at least one of $R_5$ and $R_6$ is $OR_{16}$, wherein $R_{16}$ is a monosaccharide or an oligosaccharide, as described herein.

Such compounds can include 3, 4, or more saccharide units (moieties) linked to one another, and can adopt, for example, a skeleton of any of the aminoglycosides known to exhibit an antimicrobial (e.g., antibacterial) activity.

These include, for example, amikacin, apramycin, arbekacin, butirosin, dibekacin, fortimycin, G-418, gentamycin, hygromycin, habekacin, dibekacin, netlmicin, istamycin, isepamycin, kanamycin B, lividomycin, neomycin B, paromomycin, ribostamycin, sisomycin, spectinomycin, streptomycin and tobramycin.

In some of these embodiments, the aminoglycoside skeleton is such that Ring I of the aminoglycoside interacts with the prokaryotic rRNA aminoglycoside binding site similarly to Neomycin B (NeoB).

Whenever a skeleton of an aminoglycoside is referred to, it is meant that the type (monosaccharide or oligosaccharide) of $R_{16}$ and the position of the respective $OR_{16}$ is in accordance with the skeleton of the aminoglycoside. It is further meant that all the substituents of each position in the aminoglycoside, except the position bearing the diamine-containing functional group as described herein, are substantially the same as in the respective aminoglycoside.

In some of any of the embodiments described herein, $R_5$ is $OR_{16}$ and $R_{16}$ is an oligosaccharide, e.g., a di-saccharide.

In some of these embodiments, $R_6$ is $OR_{16}$ and $R_{16}$ is hydrogen.

In exemplary embodiments, the compound features a Neomycin B skeleton, as described herein.

In some of any of the embodiments described herein, each of Rx1, Rx2, Ry1 and Rz is hydrogen.

In some of any of the embodiments described herein, each of Ry2-Ry9 and Rw1-Rw3 is hydrogen.

In some of any of the embodiments described herein, each of $R_7$ and $R_9$ is hydrogen.

In exemplary embodiments, the compound is selected from Compounds 1-10 as presented in FIG. 1 and hereinbelow.

In exemplary embodiments, the compound is selected from Compounds 2-10 as presented in FIG. 1 and hereinbelow.

In exemplary embodiments, the compound is selected from Compounds 2, 5, 8 and 10 as presented in FIG. 1 and hereinbelow.

In exemplary embodiments, the compound is Compound 8 as presented in FIG. 1 and hereinbelow.

The term "monosaccharide", as used herein and is well known in the art, refers to a simple form of a sugar that consists of a single saccharide molecule which cannot be further decomposed by hydrolysis. Most common examples of monosaccharides include glucose (dextrose), fructose, galactose, and ribose. Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms. Monosaccharides are the building blocks of oligosaccharides like sucrose (common sugar) and other polysaccharides (such as cellulose and starch).

The term "oligosaccharide" as used herein refers to a compound that comprises two or more monosaccharide units, as these are defined herein, linked to one another via a glycosyl bond (—O—) or a thioglycosyl bond (—S—). Preferably, the oligosaccharide comprises 2-6 monosaccharides, more preferably the oligosaccharide comprises 2-4 monosaccharides and most preferably the oligosaccharide is a disaccharide moiety, having two monosaccharide units.

In some of any of the embodiments described herein, the monosaccharide is a pentose moiety, such as, for example, represented by Formula II. Alternatively, the monosaccharide moiety is hexose.

In some of any of the embodiments described herein, the monosaccharide moiety is a ribose, represented by Formula II:

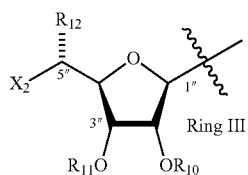

Formula II wherein:
the curved line denotes a position of attachment;
the dashed line indicates a stereo-configuration of position 5" being an R configuration or an S configuration;
$X_2$ is $OR_{13}$ or $NR_{14}R_{15}$;
each of $R_{10}$-$R_{13}$ is independently hydrogen, alkyl, cycloalkyl, acyl, a monosaccharide moiety or an oligosaccharide moiety, as defined herein; and
each of $R_{14}$ and $R_{15}$ is independently selected from the group consisting of hydrogen, alkyl, cycloalkyl, and acyl.

In some embodiments, $X_2$ is $OR_{13}$, and $R_{13}$ is hydrogen.
In some embodiments, $X_2$ is $NR_{14}R_{15}$.
In some of any of these embodiments, the compound is represented by Formula Ib:

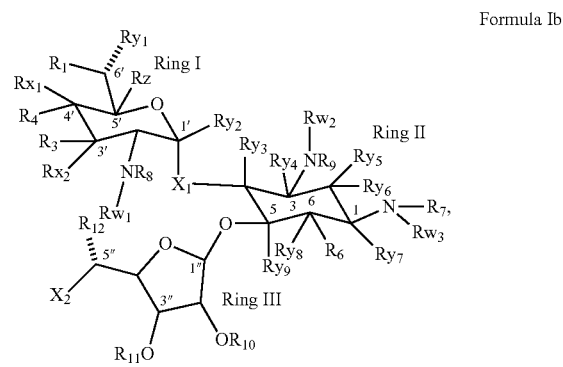

Formula Ib with the variables being as described herein for Formulae I and II, including any combination thereof.

In some of any of the embodiments of Formula Ib, $R_{11}$ is a monosacchride moiety or an oligosaccharide moiety (e.g., a di-saccharide moiety), as described herein in any of the respective embodiments and any combination thereof, such that altogether, $R_{16}$ is an oligosaccharide moiety.

In some of these embodiments, the compound is represented by Formula Ic:

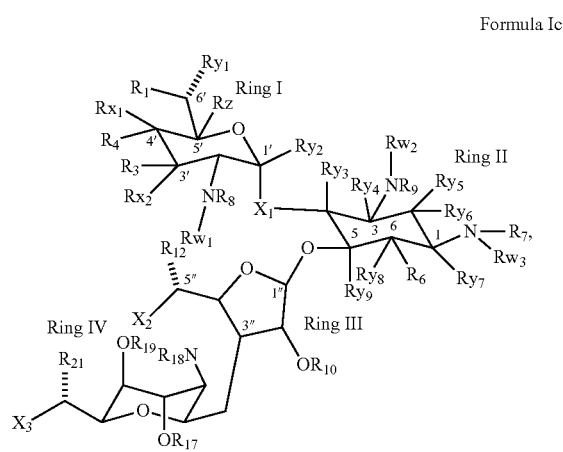

Formula Ic wherein $R_{17}$-$R_{19}$ and $R_{21}$ being as defined herein for $R_{10}$-$R_{13}$, $X_3$ being as defined herein for $X_2$, and all other variables being as described herein for Formulae I and II, including any combination thereof.

According to some of any of the embodiments described herein, the compound is represented by Formula III:

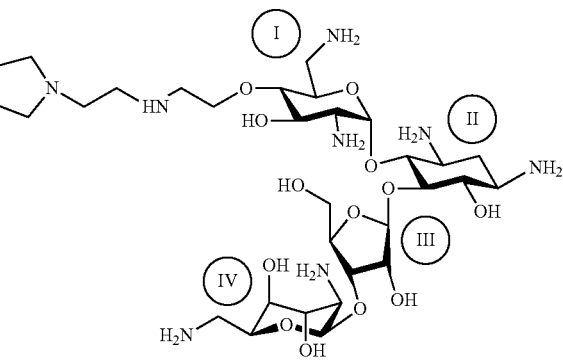

Formula III or a pharmaceutically acceptable salt thereof, wherein $R_4$ is or comprises a diamine-containing moiety, as defined herein in any of the respective embodiments and any combination thereof.

In some of the embodiments of Formula III, $R_4$ is $OR_{20}$, and $R_{20}$ is the diamine-containing functional moiety, as defined herein in any of the respective embodiments and any combination thereof.

Exemplary such compounds include Compounds 2-5, as follows:

Compound 2

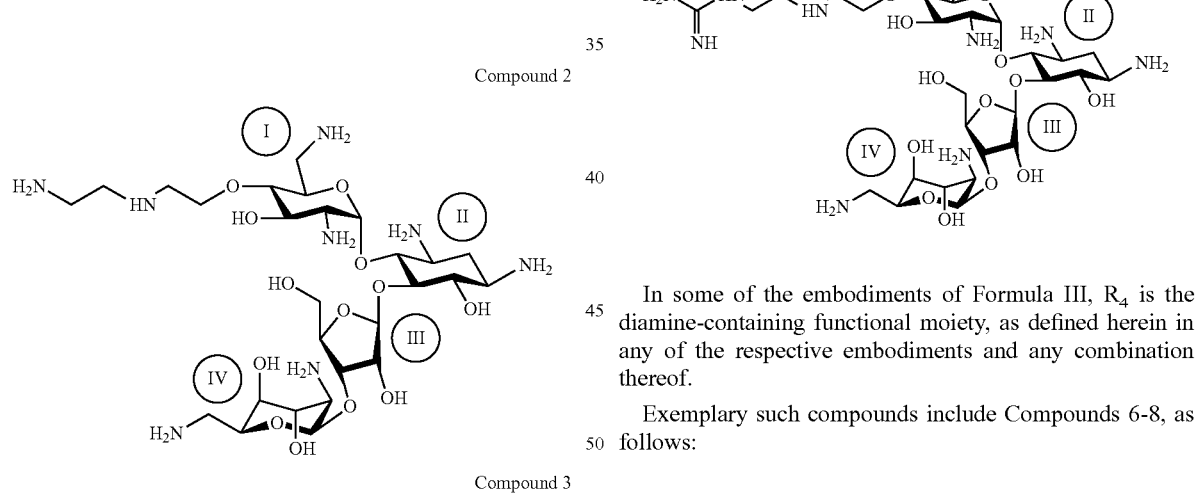

Compound 3

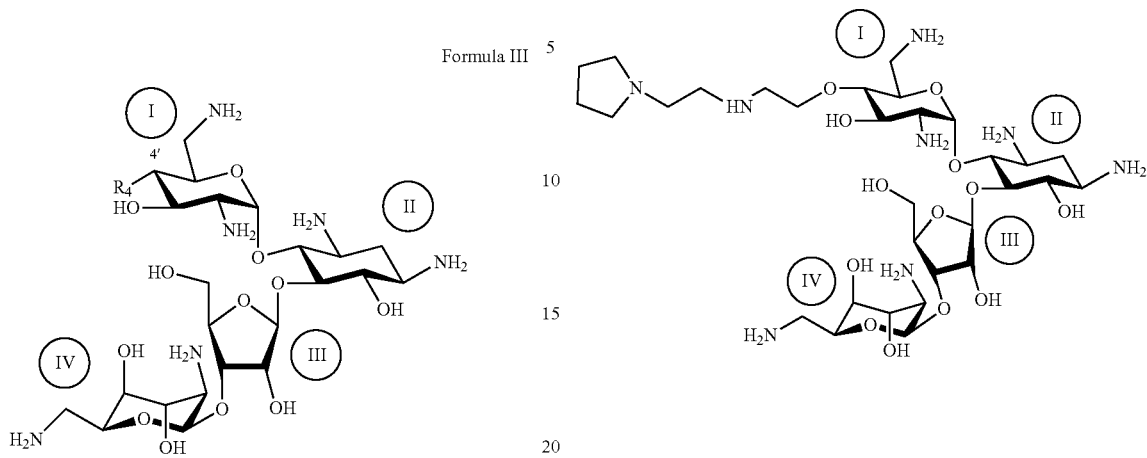

Compound 4

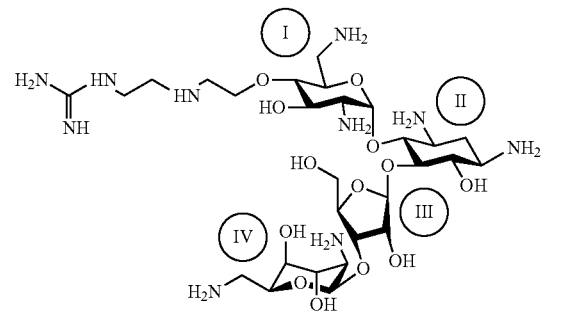

Compound 5

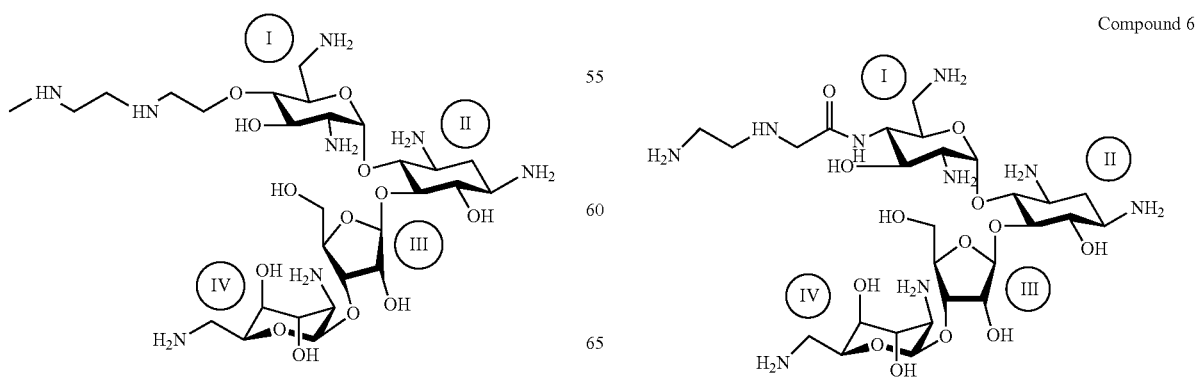

In some of the embodiments of Formula III, $R_4$ is the diamine-containing functional moiety, as defined herein in any of the respective embodiments and any combination thereof.

Exemplary such compounds include Compounds 6-8, as follows:

Compound 6

Compound 7

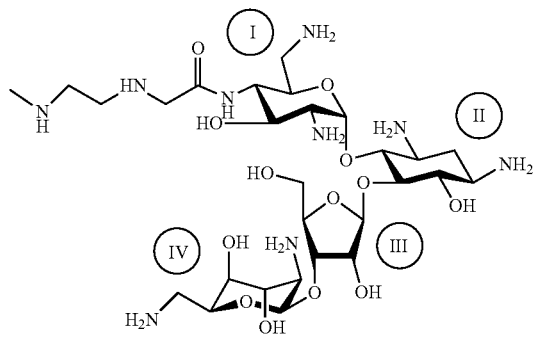

Compound 8

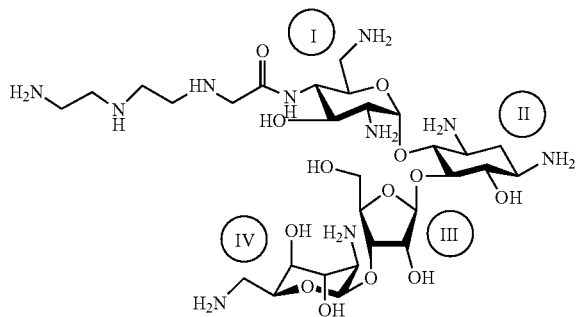

According to some of any of the embodiments described herein, the compound is represented by Formula IV:

Formula IV

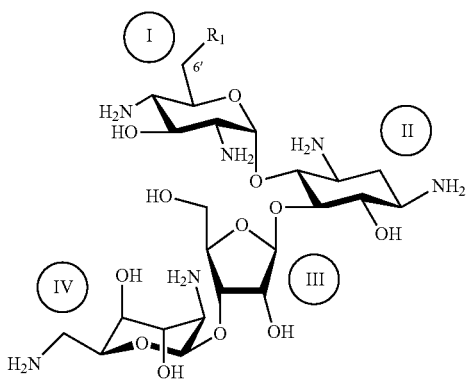

or a pharmaceutically acceptable salt thereof, wherein $R_1$ is a diamine-containing functional moiety as defined herein in any of the respective embodiments and any combination thereof.

Exemplary such compounds include Compounds 9 and 10, as follows:

Compound 9

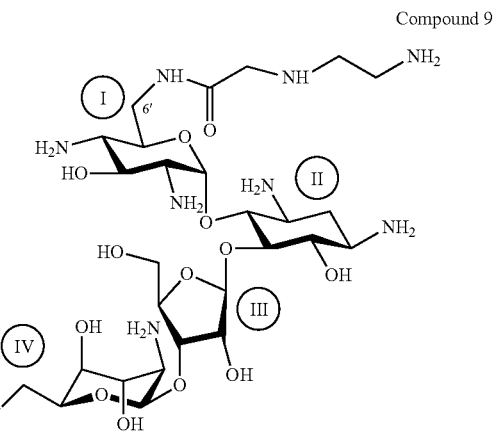

Compound 10

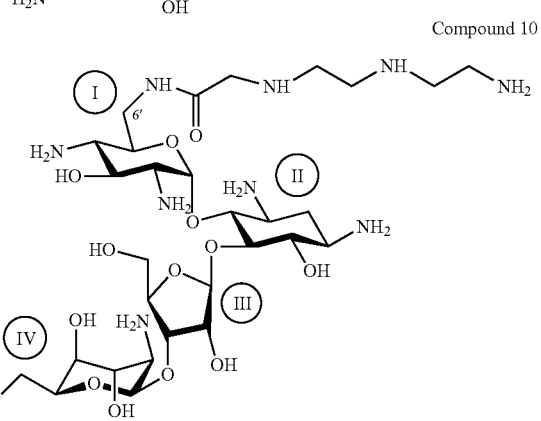

Some embodiments of the present invention relate to processes of preparing the modified aminoglycosides described herein.

Generally, the compounds can be prepared using methodologies known in the art for preparing modified aminoglycosides, which involve selectively protecting and deprotecting the amine groups and hydroxy groups present within the aminoglycoside skeleton as desired, and introducing the required substituted at the desired position.

In some embodiments, preparing a compound as described herein involves selecting or generating a suitable aminoglycoside compound to be modified, which feature 2, 3, or 4 saccharide units, each being substituted by amine and hydroxy substituents, protecting the amine groups, protecting the hydroxyl groups and then selectively deprotecting the protected group at the position to which a diamine-containing functional moiety should be introduced.

The phrase "protected group", as used herein, refers to a group that is substituted or modified so as to block its functionality and protect it from reacting with other groups under the reaction conditions. A protected group is regenerated by removal of the substituent or by being re-modified.

When an "amino-protected group" or "hydroxyl-protected group" are used, it is meant that a protecting group is attached or used to modify the respective group so as to generate the protected group.

The phrase "protecting group", as used herein, refers to a substituent or a modification that is commonly employed to block or protect a particular functionality while reacting other functional groups on the compound. The protecting group is selected so as to release the substituent or to be re-modified, to thereby generate the desired unprotected group.

For example, an "amino-protecting group" or "amine-protecting group" is a substituent attached to an amino group, or a modification of an amino group, that blocks or protects the amino functionality in the compound, and prevents it from participating in chemical reactions. The amino-protecting group is removed by removal of the substituent or by a modification that re-generates an amine group.

Suitable amino-protected groups include azide (azido), N-phthalimido, N-acetyl, N-trifluoroacetyl, N-t-butoxycarbonyl (BOC), N-benzyloxycarbonyl (CBz) and N-9-fluorenylmethylenoxycarbonyl (Fmoc).

A "hydroxy-protecting group" or "hydroxyl-protecting group" refers to a substituent or a modification of a hydroxyl group that blocks or protects the hydroxyl functionality, and prevents it from participating in chemical reactions. The hydroxy-protecting group is removed by removal of the substituent or by a modification that re-generates a hydroxy group.

Suitable hydroxy protected groups include isopropylidene ketal and cyclohexanone dimethyl ketal (forming a 1,3-dioxane with two adjacent hydroxyl groups), 4-methoxy-1-methylbenzene (forming a 1,3-dioxane with two adjacent hydroxyl groups), O-acetyl, O-chloroacetyl, O-benzoyl (OBn) and O-silyl.

For a general description of protecting groups and their use, see T. W. Greene, Protective Groups in Organic Synthesis, John Wiley & Sons, New York, 1991.

It is noted herein that when applicable, a "protected group" refers to a moiety in which one reactive function on a compound is protected or more than one function are protected at the same time, such as in the case of two adjacent functionalities, e.g., two hydroxyl groups that can be protected at once by a isopropylidene ketal.

Exemplary synthetic pathways are described in Example 2 in the Examples section that follows, and are presented in FIGS. 2A, 2B and 3.

Some embodiments of the present invention relate to intermediates formed while preparing compounds as described herein.

Exemplary such intermediates include Compounds 11-18, shown in FIG. 2A, Compounds 19-29 shown in FIG. 2B, and Compounds 30-36 shown in FIG. 3.

According to some of any of the embodiments described herein, any of the compounds prepared or provided according to the present embodiments can be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, and/or to improve its stability, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., an amine-containing group such as amine and/or guanidyl and/or guanyl) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Therapeutic Uses:

The compounds according to some embodiments of the present invention are effective in treating medical conditions associated with a pathogenic microorganism in a subject.

The compounds presented herein can also be effective in treating medical conditions associated with pathogenic microorganisms which have already developed resistance to any antibiotic agent.

The phrases "effective in treating medical conditions associated with pathogenic microorganisms", "effective in treating a subject diagnosed with a medical conditions associated with pathogenic microorganisms" and/or "for use in the treatment of a medical condition associated with a pathogenic microorganism in a subject", as used herein interchangeably, refer to characteristics of a substance, such as the compounds according to some embodiments of the present invention, that can effect death, killing, eradication, elimination, reduction in number, reduction of growth rate, reduction of a load, and/or a change in population distribution of one or more species of pathogenic microorganisms, as well as effecting a reduction or prevention of the emergence of resistance of such microorganisms to the substance.

Herein throughout, the phrase "pathogenic microorganism" is used to describe any microorganism which can cause a disease or disorder in a higher organism, such as mammals in general and a human in particular. The pathogenic microorganism may belong to any family of organisms such as, but not limited to prokaryotic organisms, *eubacterium*, archaebacterium, eukaryotic organisms, yeast, fungi, algae, protozoan, and other parasites.

Non-limiting examples of pathogenic microorganism include *Plasmodium falciparum*; and related malaria-causing protozoan parasites, *Acanthamoeba* and other free-living amoebae, *Aeromonas hydrophila*, *Anisakis* and related worms, and further include, but not limited to *Acinetobacter baumanii*, *Ascaris lumbricoides*, *Bacillus cereus*, *Brevundimonas diminuta*, *Campylobacter jejuni*, *Clostridium botulinum*, *Clostridium perfringens*, *Cryptosporidium parvum*, *Cyclospora cayetanensis*, *Diphyllobothrium*, *Entamoeba histolytica*, certain strains of *Escherichia coli*, *Eustrongylides*, *Giardia lamblia*, *Klebsiella pneumoniae*, *Listeria monocytogenes*, *Nanophyetus*, *Plesiomonas shigelloides*, *Proteus mirabilis*, *Pseudomonas aeruginosa*, *Salmonella*, *Serratia odorifera*, *Shigella*, *Staphylococcus aureus*, *Stenotrophomonas maltophilia*, *Streptococcus*, *Trichuris trichiura*, *Vibrio cholerae*, *Vibrio parahaemolyticus*, *Vibrio vulnificus* and other vibrios, *Yersinia enterocolitica*, *Yersinia pseudotuberculosis* and *Yersinia kristensenii*.

Other pathogens include Strep. *pyogenes* (Group A), Strep. *pneumoniae*, Strep. GpB, Strep. *viridans*, Strep. GpD (*Enterococcus*), Strep. GpC and GpG, Staph. *aureus*, Staph. *epidermidis*, Bacillus subtilis, Bacillus anthracis, Listeria monocytogenes, Anaerobic cocci, Clostridium spp., Actinomyces spp, Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella spp., Yersinia enterocolitica, Acinetobacter calcoaceticus, Flavobacterium spp., Haemophilus influenzae, Pseudomonas aeruginosa, Campylobacter jejuni, Vibrio parahaemolyticus, Brucella spp., Neisseria meningitidis, Neisseria gonorrhoea, Bacteroides fragilis, Fusobacterium spp., Mycobacterium tuberculosis (including MDR and XDR strains from hospital origins isolated from patients) and Mycobacterium smegmatis.

Accordingly, a condition associated with a pathogenic microorganism describes an infectious condition that results from the presence of the microorganism in a subject. The infectious condition can be, for example, a bacterial infection, a fungal infection, a protozoal infection, and the like, collectively referred to herein as "microbial infection".

Some higher forms of microorganisms are pathogenic per-se, and other harbor lower forms of pathogenic bacteria, thus present a medical threat expressed in many medical conditions, such as, without limitation, actinomycosis, anthrax, aspergillosis, bacteremia, bacterial skin diseases, *bartonella* infections, botulism, brucellosis, *burkholderia* infections, *campylobacter* infections, candidiasis, cat-scratch disease, *chlamydia* infections, cholera, *clostridium* infections, coccidioidomycosis, cryptococcosis, dermatomycoses, dermatomycoses, diphtheria, ehrlichiosis, epidemic louse borne typhus, *Escherichia coli* infections, *fusobacterium* infections, gangrene, general infections, general mycoses, gram-negative bacterial infections, Gram-positive bacterial infections, histoplasmosis, impetigo, *klebsiella* infections, legionellosis, leprosy, leptospirosis, *listeria* infections, lyme disease, maduromycosis, melioidosis, *mycobacterium* infections, *mycoplasma* infections, necrotizing fasciitis, *nocardia* infections, onychomycosis, ornithosis, pneumococcal infections, pneumonia, *pseudomonas* infections, Q fever, rat-bite fever, relapsing fever, rheumatic fever, *rickettsia* infections, Rocky-mountain spotted fever,

*salmonella* infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, *vibrio* infections, yaws, *yersinia* infections, *Yersinia pestis* plague, zoonoses and zygomycosis.

The compounds presented herein can be effectively used against bacterial strains which have developed or are prone to or capable of developing resistance to at least one antimicrobial agents. Non-limiting examples of such bacterial strains include:
(a) Gram-positive bacteria such as Strep. *pyogenes* (Group A), Strep. *pneumoniae*, Strep. GpB, Strep. *viridans*, Strep. GpD -(*Enterococcus*), Strep. GpC and GpG, Staph. *aureus*, Staph. *epidermidis, Bacillus subtilis, Bacillus anthraxis, Listeria monocytogenes, Anaerobic cocci, Clostridium* spp., and *Actinomyces* spp; and
(b) Gram-negative bacteria such as *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi* murium, *Salmonella* virchow, *Shigella* spp., *Yersinia enterocolitica, Acinetobacter calcoaceticus, Flavobacterium* spp., *Haemophilus influenzae, Pseudomonas aueroginosa, Campylobacter jejuni, Vibrio parahaemolyticus, Brucella* spp., *Neisseria meningitidis, Neisseria gonorrhoea, Bacteroides fragilis*, and *Fusobacterium* spp.

According to some embodiments of the present invention, the compounds presented herein can be effectively used against bacterial strains which have developed or are prone to or capable of developing resistance to at least one antimicrobial agent.

According to some embodiments of the present invention, the compounds presented herein can be effectively used against bacterial strains which have developed or are prone to or capable of developing resistance to at least one antibacterial agent.

According to some embodiments of the present invention, the compounds presented herein can be effectively used against bacterial strains which have developed or are prone to or capable of developing resistance to an aminoglycoside antibacterial agent.

Exemplary such bacterial strains include but not limited to, *Escherichia coli* strains such as *E. coli* R477-100, *E. coli* ATCC 25922, *E. coli* AG100B, *E. coli* ATCC 35218 and *E. coli* AG100A, *B. subtilis* strains (e.g., ATCC 6633), MRSA strains (e.g., ATCC 43300), and *Pseudomonas* aueroginosa strains.

Thus, according to one aspect of the present invention there is provided a method of treating a medical condition associated with a pathogenic microorganism in a subject. The method is effected by administering to that subject, a therapeutically effective amount of a compound as presented herein.

As used herein, the phrase "therapeutically effective amount" describes an amount of an active agent being administered, which will relieve to some extent one or more of the symptoms of the condition being treated. In the context of the present embodiments, the phrase "therapeutically effective amount" describes an amount of a compound being administered and/or re-administered, which will relieve to some extent one or more of the symptoms of the condition being treated by being at a level that is harmful to the target microorganism(s), and cause a disruption to the life-cycle of the target microorganism(s), namely a bactericidal level or otherwise a level that inhibits the microorganism growth or eradicates the microorganism.

The efficacy of any antimicrobial agent, including the compounds presented herein, is oftentimes referred to in minimal inhibitory concentration units, or MIC units. A MIC is the lowest concentration of an antimicrobial agent, typically measured in micro-molar (M) or micrograms per milliliter (g/ml) units, which can inhibit the growth of a microorganism after a period of incubation, typically 24 hours. MIC values are used as diagnostic criteria to evaluate resistance of microorganisms to an antimicrobial agent, and for monitoring the activity of an antimicrobial agent in question. MICs are determined by standard laboratory methods, as these are described and demonstrated in the Examples section that follows. Standard laboratory methods typically follow a standard guideline of a reference body such as the Clinical and Laboratory Standards Institute (CLSI), British Society for Antimicrobial Chemotherapy (BSAC) or The European Committee on Antimicrobial Susceptibility Testing (EUCAST). In clinical practice, the minimum inhibitory concentrations are used to determine the amount of antibiotic agent that the subject receives as well as the type of antibiotic agent to be used.

According to another aspect of embodiments of the present invention, each of the compounds described herein is for use in treating a medical condition associated with a pathogenic microorganism and/or in treating a subject diagnosed with a medical condition associated with a pathogenic microorganism.

According to another aspect of embodiments of the present invention, there is provided a use of any of the compounds described herein as a medicament or in the manufacture of a medicament. In some embodiments, the medicament is for treating a medical condition associated with a pathogenic microorganism and/or a subject diagnosed with a medical condition associated with a pathogenic microorganism.

The compounds presented herein can be administered via any administration route, including, but not limited to, orally, by inhalation, or parenterally, for example, by intravenous drip or intraperitoneal, subcutaneous, intramuscular or intravenous injection, or topically (including ophthalmically, vaginally, rectally, intranasally).

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

Pharmaceutical Compositions:

In any of the methods and uses described herein, the compounds described herein can be utilized either per se or form a part of a pharmaceutical composition, which further comprises a pharmaceutically acceptable carrier, as defined herein.

According to an aspect of some embodiments of the present invention, there is provided a pharmaceutical composition which comprises, as an active ingredient, any of the novel compounds described herein and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, PA, latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglycoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

Thus, in some embodiments, the pharmaceutical composition is packaged in a packaging material and identified in print, in or on the packaging material, for use in the treatment of a medical condition associated with a pathogenic microorganism, as defined herein.

In any of the composition, methods and uses described herein, the compounds can be utilized in combination with other agents useful in the treatment of the medical conditions described herein.

It is expected that during the life of a patent maturing from this application additional relevant aminoglycoside skeletons will be developed and the scope of the term modified aminoglycoside is intended to include all such new technologies a priori.

It is expected that during the life of a patent maturing from this application additional relevant pathogenic microorganisms will be developed and the scope of this phrase is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group" it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. The number of carbon atoms can range from 2 to 20, and is preferably lower, e.g., from 1 to 10, or from 1 to 6, or from 1 to 4. A hydrocarbon can be a linking group or an end group.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

Further alternatively, R' and R" form together a heteroalicyclic nitrogen-containing ring.

The amine group as described herein can be in a protonated or an ammonium form, as described herein.

The term "alkyl" describes a saturated aliphatic hydrocarbon including straight chain and branched chain groups. Preferably, the alkyl group has 1 to 30, or 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. The alkyl group may be substituted or unsubstituted.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene and Alkyne, as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted.

The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

Representative examples are piperidine, piperazine, tetrahydrofurane, tetrahydropyrane, morpholino, oxalidine, and the like.

The heteroalicyclic may be substituted or unsubstituted. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

A "guanidino" or "guanidine" or "guanidinyl" or "guanidyl" group refers to an —RaNC(=NRd)-NRbRc group, where each of Ra, Rb, Rc and Rd can each be as defined herein for R' and R".

A "guanyl" or "guanine" group refers to an RaRbNC(=NRd)- group, where Ra, Rb and Rd are each as defined herein for R' and R".

In some of any of the embodiments described herein, the guanidine group is —NH—C(=NH)—NH$_2$.

In some of any of the embodiments described herein, the guanyl group is H$_2$N—C(=NH)— group.

Any one of the amine (including modified amine), guanidine and guanine groups described herein is presented as a free base form thereof, but is meant to encompass an ionized form thereof at physiological pH, and/or within a salt thereof, e.g., a pharmaceutically acceptable salt thereof, as described herein.

Whenever an alkyl, cycloalkyl, aryl, alkaryl, heteroaryl, heteroalicyclic, acyl and any other moiety as described herein is substituted, it includes one or more substituents, each can independently be, but are not limited to, hydroxy, alkoxy, thiohydroxy, thioalkoxy, aryloxy, thioaryloxy, alkaryl, alkenyl, alkynyl, sulfonate, sulfoxide, thiosulfate, sulfate, sulfite, thiosulfite, phosphonate, cyano, nitro, azo, sulfonamide, carbonyl, thiocarbonyl, C-carboxylate, O-carboxylate, N-thiocarbamate, O-thiocarbamate, oxo, thiooxo, oxime, acyl, acyl halide, azo, azide, urea, thiourea, N-carbamate, O-carbamate, C-amide, N-amide, guanyl, guanidyl, hydrazine and hydrazide, as these terms are defined herein.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O-linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'-linking group, as these phrases are defined hereinabove, with R' and R" defined herein.

The term "N-sulfonamide" describes an R'S(=O)$_2$—NR"— end group or a —S(=O)$_2$—NR'-linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)-linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)-linking group, as these phrases are defined hereinabove, with R' and R" as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)-linking group, as these phrases are defined hereinabove, with R' as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N=C=O group.

The term "isothiocyanate" describes an —N=C=S group.

The term "nitro" describes an —NO$_2$ group.

The term "acyl halide" describes a —(C=O)R'''' group wherein R'''' is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'-linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'-linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'-linking group, as these phrases are defined hereinabove, with R' and R" as defined herein.

The term "urea", which is also referred to herein as "ureido", describes a —NR'C(=O)—NR"R''' end group or a —NR'C(=O)—NR"— linking group, as these phrases are defined hereinabove, where R' and R" are as defined herein and R''' is as defined herein for R' and R".

The term "thiourea", which is also referred to herein as "thioureido", describes a —NR'—C(=S)—NR"R''' end group or a —NR'—C(=S)—NR"— linking group, with R', R" and R''' as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" also describes a R'R"NC(=N)— end group or a —R'NC(=N)— linking group, as these phrases are defined hereinabove, where R' and R" are as defined herein.

The term "guanidine" also describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

Herein throughout, the term "acyl" describes a —C(=O)—R group, wherein R is as described herein.

Herein throughout, the term "acyl" describes a —C(=O)—R group, with R being a substituted or unsubstituted alkyl, cycloalkyl, aryl, alkaryl, a hydrocarbon chain, or hydrogen.

In exemplary embodiments, the acyl is such that R is an alkyl or alkaryl or aryl, each of which being optionally substituted by one or more amine substituents.

In some embodiments, R is a substituted alkyl, and in some embodiments, R is substituted by hydroxy at the a position with respect to the carbonyl group, such that the acyl is a-hydroxy-acyl.

In some embodiments, the a-hydroxy-acyl is further substituted by one or more amine groups, and is an amino-substituted a-hydroxy-acyl.

In some of the embodiments of an acyl group as described herein, the amine substituents can be, for example, at one or more of positions β, γ, δ, and/or ω of the moiety R, with respect to the acyl.

Exemplary amino-substituted a-hydroxy-acyls include, without limitation, the moiety (S)-4-amino-2-hydroxybutyryl, which is also referred to herein as AHB. According to some embodiments of the present invention, an alternative to the AHB moiety can be the α-hydroxy-β-aminopropionyl (AHP) moiety. Additional exemplary amino-substituted α-hydroxy-acyls include, but are not limited to, L-(−)-γ-amino-α-hydroxybutyryl, L(−)-δ-amino-α-hydroxyvaleryl, L-(−)-β-benzyloxycarbonylamino-α-hydroxypropionyl, a L-(−)-δ-benzyloxycarbonylamino-α-hydroxyvaleryl.

It is noted herein that according to some embodiments of the present invention, other moieties which involve a combination of carbonyl(s), hydroxyl(s) and amino group(s) along a lower alkyl exhibiting any stereochemistry, are contemplated as optional substituents in place of AHB and/or AHP, including, for example, 2-amino-3-hydroxybutanoyl, 3-amino-2-hydroxypentanoyl, 5-amino-3-hydroxyhexanoyl and the likes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

General Techniques:

NMR spectra (including $^1$H, $^{13}$C, DEPT, 2D COSY, 1D TOCSY, HMQC, HMBC) were recorded with a Bruker Avance 500 spectrometer, and chemical shifts are reported relative to internal Me$_4$Si (d=0.0 ppm) with CDCl$_3$ as the solvent or to MeOD (d=3.35 ppm) as the solvent.

$^{13}$C NMR spectra were recorded with a Bruker Avance 500 spectrometer at 125.8 MHz, and the chemical shifts are reported relative to the solvent signal for CDCl$_3$ (d=77.00 ppm) or to the solvent signal for MeOD (d=49.0 ppm).

Mass spectra analyses were obtained with a Bruker Daltonix Apex 3 mass spectrometer under electrospray ionization (ESI) or a TSQ-70B mass spectrometer (Finnigan Mat).

Reactions were monitored by TLC on Silica Gel 60 F254 (0.25 mm, Merck), and spots were visualized by charring with a yellow solution containing (NH$_4$)Mo$_7$O$_{24}$·4H$_2$O (120 grams) and (NH$_4$)$_2$Ce(NO$_3$)$_6$ (5 grams) in 10% H$_2$SO$_4$ (800 mL).

Flash column chromatography was performed on Silica Gel 60 (70-230 mesh).

All reactions were performed under an argon atmosphere with anhydrous solvents, unless otherwise indicated.

Neomycin B and paromomycin as analytical samples for comparative biochemical assays were purchased from Sigma.

For chemical syntheses, large-scale paromomycin (used as a starting material) was purchased from Apollo Scientific (Stockport, UK).

All other chemicals and biochemicals, unless otherwise indicated, were obtained from commercial vendors.

In all biological tests, all the tested aminoglycosides were in their sulfate salt forms, except Compound 5, which was used as its trifluoroacetate salt.

Biochemical Assays:

Prokaryotic in vitro translation inhibition by the different standard and synthetic aminoglycosides was quantified in coupled transcription/translation assays by use of *E. coli* S30 extract for circular DNA with the pBESTluc plasmid (Promega), according to the manufacturer's protocol.

Translation reactions (25 mL) containing variable concentrations of the tested aminoglycoside were incubated at 37° C. for 60 minutes, cooled on ice for 5 minutes, and diluted with a dilution reagent [Tris-phosphate buffer (25 mm, pH 7.8), dithiothreitol (DTT, 2 mm), 1,2-diaminocyclohexanetetraacetate (2 mm), glycerol (10%), triton $X_{100}$ (1%), and bovine serum albumin (BSA, 1 mg/mL] into 96-well plates.

The luminescence was measured immediately after the addition of Luciferase Assay Reagent (Promega) (50 mL), and light emission was recorded with a Victor3 Plate Reader (PerkinElmer).

The concentration of half-maximal inhibition ($IC^{50}$) was obtained from fitting concentration-response curves to the data of at least three independent experiments by using Grafit 5 software.

Comparative antibacterial activities were determined by measuring the MIC values by using the double-microdilution method according to the National Committee for Clinical Laboratory Standards (NCCLS).

All the experiments were performed in triplicate, and analogous results were obtained in three different experiments.

For the rRNA cleavage experiments, the ribosomes were isolated from *E. coli* cells (R477-100) by following the reported protocol.

Ribosomes were pelleted from pooled fractions (35 K for 15 hours at 4° C.) and were re-suspended in buffer for snap freezing in liquid nitrogen and storage at −80° C. The resin was rinsed with water after use and was stored in 20% ethanol at 48° C. The catalytic domain of ColE3 was purified from its immunity protein as previously described [44]. Briefly, after elution from the Ni-affinity column with 6M Gn·HCl, the ColE3 RNase became unfolded. It refolded upon dialysis in 50 mM potassium phosphate or 20 mM Tris pH 7.5 buffer.

All parts of the purification procedure could be performed at room temperature, and the product was analyzed on 16% SDS-PAGE.

The cleavage experiments of rRNA with *E. coli* ribosomes were performed by incubation of freshly isolated ribosomes for 24 hours (5 minutes in the case of ColE3; 37° C., pH 7.0) in the presence of ethylenediamine, NeoB, Compound 3, or ColE3.

After incubation, RNA was phenol/chloroform extracted from samples and was electrophoresed on a 6% acrylamide TBE/urea gel for 100 minutes at 180 V, stained with SYBR Gold, and analyzed by fluorescence.

A short RNA oligomer that represented the bacterial A-site sequence labeled with a fluorescent tag (23 bases, for sequence, see FIGS. 7A and 7B and SEQ ID NOs: 2 and 3) was also used for rRNA cleavage experiments. This RNA sequence was purchased from Dharmacon and was used without further purification.

The cleavage experiments were performed by using gel electrophoresis; the rRNA fragments were analyzed on 20% TBE/urea gel and were visualized by fluorescence.

Molecular Dynamics Simulations:

MD simulations were performed on the model of the A-site containing two symmetric aminoglycoside binding sites by using the crystal structure of the A-site with neomycin B bound (PDB ID: 2ET4) [B. FranÅois, R. J. M. Russell, J. B. Murray, F. Aboul-ela, B. Masquida, Q. Vicens, E. Westhof, Nucleic Acids Res. 2005, 33, 5677-5690]. The oligonucleotide sequence used in this model is presented herein as SEQ ID NO: 3.

The MD simulation protocol consisted of energy minimization, thermalization, equilibration, and production phases. In the first two phases, harmonic constraints with a force constant of 10 kcal·mol$^{-1}$·Å$^{-2}$ were imposed on heavy atoms of the solute.

First, all systems were energy minimized with the above restraints undergoing 5000 steps of steepest descent followed by 4000 steps of conjugate gradient minimization by using sander (Amber 12).

The next phases were performed with NAMD [J. C. Phillips, R. Braun, W. Wang, J. Gumbart, E. Tajkhorshid, E. Villa, C. Chipot, R. D. Skeel, L. Kal8, K. Schulten, J. Comput. Chem. 2005, 26, 1781-1802].

Second, during thermalization (in the NVT ensemble), each system was heated from 10 to 310 K, increasing the temperature by 10K every 100 ps. Then, 2 ns simulations at 310 K were performed. Third, equilibration was performed in the NpT ensemble with a constant pressure of 1 Atm controlled by using the Langevin Piston method and at constant temperature of 310 K regulated by Langevin dynamics with a damping factor of 1 ps$^{-1}$.

During 5 ns equilibration, the restraints were exponentially decreased in 50 time windows (scaled from 1 to 0.0065). Further, the 120 ns production runs were performed without any restraints.

Periodic boundary conditions and the Particle Mesh Ewald method with a grid spacing of 1 Å were used. The SHAKE algorithm and an integration time step of 2 fs were applied.

For nonbonded interactions, a short-range cutoff of 12 Å was used.

In order to calculate the GaMD acceleration parameters, the original simulation experiments were followed by the GaMD simulation [38, 39] experiments with an additional 2 ns of MD simulation.

After adding the boost potential, the simulation was continued for 30 ns to equilibrate the system. Subsequently, ten independent GaMD production runs were conducted for 100 ns each, starting with randomized initial atomic velocities.

The GaMD simulations were performed in the dual-boost mode, in which the boost potential was applied to the dihedral and total potential energy terms.

The threshold energy was set to the lower bound, that is, E=Vmax. The upper limit of the boost potential standard deviation, $\sigma_0$, was set to 10 kcal·mol$^{-1}$ for the dihedral and total potential energetic terms.

Example 1

Rationale of the Design of Modified Aminoglycosides

The following aspects were first considered while designing the novel aminoglycoside derivatives of the present embodiments: The choice of the phosphodiester bond in the A-site that should be the most susceptible to cleavage; the potential "warhead" structure that may exhibit a catalytic cleavage; and the attachment site of a "warhead" on the aminoglycoside structure.

It has been shown that successful cleavage of an RNA phosphodiester bond requires substantial motion in the HO—C2'-C3'-O—P bonds of the ribose-3'-phosphate region to reach the necessary low-energy transition state where the C2'-OH group is orientated for in-line nucleophilic attack on the scissile bond [T. Lçnnberg, K. M. Kero, Org. Biomol. Chem. 2012, 10, 569-574].

Such flexibility is usually achieved by enzyme-induced flipping of the base attached to the RNA scissile bond. The mechanisms suggested for RNase T1, RNase a-sarcin, and several ribozymes, mentioned in the Background section, are examples that support this notion.

The proposed mechanism for colicinE3 (ColE3), a natural enzymatic toxin produced in several *Escherichia coli* strains that selectively cleaves a phosphodiester bond between A1493 and G1494 of 16S rRNA is also of relevance [C. L. Ng, K. Lang, N. A. G. Meenan, A. Sharma, A. C. Kelley, C. Kleanthous, V. Ramakrishnan, Nat. Struct. Mol. Biol. 2010, 17, 1241-1246]. This cleavage impairs the protein-translation process and, consequently, leads to cell death.

The proposed mechanism of ColE3 explains why this natural ribonuclease cleaves a specific position in the A-site of rRNA, between A1493 and G1494. This region of the A-site is very important functionally (for correct proofreading) and is also one of the most flexible and accessible regions in the whole ribosome, because it needs to accommodate the incoming aminoacyl-tRNA.

The present inventors have assumed that the target phosphodiester bond should be within the region of rRNA that upon binding of an aminoglycoside undergoes the most extensive conformational change. This region is virtually the same as that of ColE3 binding: G1491-A1492-A1493-G1494.

Given that the binding of most aminoglycosides induces extensive flipping of the A1492 and A1493 base residues from the bulged-in (ligand-unbound ribosome) to the bulged-out conformation [B. FranÅois, R. J. M. Russell, J. B. Murray, F. Aboul-ela, B. Masquida, Q. Vicens, E. Westhof, Nucleic Acids Res. 2005, 33, 5677-5690], similar to that of ColE3 binding [C. L. Ng, K. Lang, N. A. G. Meenan, A. Sharma, Nat. Struct. Mol. Biol. 2010, 17, 1241-1246], the present inventors have assumed that the best three phosphodiester bond candidates within the A site are between G1491-A1492, A1492-A1493, and A1493-G1494.

As indicated hereinabove, previous studies with simple diamines demonstrated their ability to accelerate cleavage of adenylyl(3'-5')-adenosine (ApA) from one to three orders of magnitude more efficiently than the corresponding monoamines.

Ethylenediamine, methyl ethylenediamine, diethylenetriamine, N-(2-aminoethyl)pyrrolidine, and guanidine-ethyleneamine were selected as potential "catalytic warheads" for preparing newly designed NeoB derivatives exemplified herein as Compounds 1-10 (see, FIG. 1).

The 4'-hydroxy group (ring I) of NeoB (see, FIG. 1) was first selected as the attachment site.

As shown in FIGS. 4A-B, preliminary molecular modeling studies of the proposed warheads linked at the 4'-position showed that the phosphodiester bond between G1491 and A1492 was the closest one and that its cleavage may be feasible through acid-base catalysis: the terminal amino group in its ammonium form can activate the phosphate between G1491 and A1492 as a general acid (3.9 a distance), and the next-nearest amine can activate the 2'-hydroxy group of G1491 as a general base (2.6 a distance).

Thus, G1491-A1492 was selected as the cleavage site, as schematically illustrated in FIG. 4B.

Example 2

Chemical Syntheses of Newly Designed Aminoglycoside Derivatives of NeoB

Synthesis of 4'-O-Linked Compounds (Compounds 1-5):

To selectively modify NeoB at the desired 4'-position, a synthetic pathway for its simplest fragment, that is, neamine, which consists of rings I and II of NeoB, was designed, and Compound 1 was prepared accordingly, as illustrated in FIG. 2A.

The synthesis started from commercial paromomycin sulfate; it was treated with anhydrous HCl [acetyl chloride (AcCl) in MeOH] at reflux, which resulted in highly regioselective hydrolysis between rings II and III to give paromamine as its hydrochloride salt. The obtained salt was converted into the freebase form by passing it through a column of Dowex 50W (H+ form). Paromamine in its free-base form was then converted into corresponding perazido derivative 11 by a diazo-transfer reaction in the presence of trifluoromethanesulfonyl azide (TfN$_3$), CuSO$_4$·5H$_2$O, and Et$_3$N.

Treatment of 11 with benzaldehyde dimethylacetal in dry DMF in the presence of camphorsulfonic acid (CSA) afforded the corresponding benzylidene acetal 12, which was then O-benzylated with benzyl bromide (BnBr) in the presence of NaH in DMF to yield tribenzyl ether 13. Removal of the benzylidene group (acetic acid, 60° C.) gave corresponding diol 14, which was then selectively tosylated at the 6'-hydroxy group by using 4-toluenesulfonyl chloride (TsCl) in pyridine (py); this was followed by nucleophilic substitution with sodium azide to yield compound 15. Allylation of the 4'-hydroxy group with allyl bromide in the presence of NaH in DMF gave 4'-allyl derivative 16. Attempts to convert 16 into the corresponding aldehyde by ozonolysis resulted in a mixture of products owing to partial oxidation of the benzyl groups. To solve this problem, the double bond in 16 was first converted into corresponding diol 17 by using a previously described procedure [24]. Oxidative cleavage of diol 17 [PhI(OAc)$_2$, CH$_2$Cl$_2$] was followed by in situ reductive amination with 2-azidoethanamine to yield corresponding 4'-azido amine 18 in 66% yield. Finally, after several unsuccessful attempts to remove the benzyl and azide protections in 18, a sequential operation involving Staudinger and Birch reactions was determined as the best protocol. Thus, the Staudinger reaction (PMe$_3$, NaOH) followed by Birch reduction (Na/NH$_3$, THF) gave target compound 1 in 65% yield.

The 4'-O-substituted derivatives of NeoB, Compounds 2-5 (See, FIG. 1), were synthesized using the same strategy as that described for the synthesis of Compound 1 with some modifications, as illustrated in FIG. 2B.

The following modifications were applied:

Unlike the azidation of paromamine with TfN$_3$ to yield corresponding perazido derivative 11 (FIG. 3), the same reaction on paromomycin gave a very low yield of desired perazido derivative 19. In an attempt to improve the yield of the desired perazido product, instead of TfN$_3$, imidazole-1-sulfonyl azide hydrochloride (ImSO$_2$N$_3$·HCl) was used, and the tosyl chloride was replaced with the more bulky triisopropylsulfonyl chloride (trisyl chloride), which was more selective for protection of the 6'-hydroxy group (conversion of Compound 22 into 23) and gave 60% yield over two steps (trisylation and azidation).

Common intermediate diol 25 was separately subjected to in situ oxidation and reductive amination steps with four different amine linkers, compounds A, B, 1-(2-aminoethyl)pyrrolidine, and C (shown below), to afford the corresponding protected 4'-O-derivatives of NeoB, compounds 26-29 (See, FIG. 2B).

A

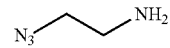

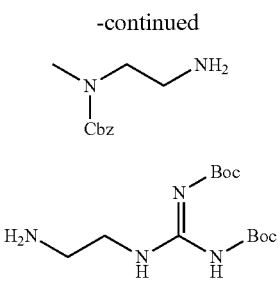

B, C

The Staudinger reaction (PMe₃, NaOH) followed by the Birch reduction (Na/NH₃, THF) gave Compounds 2-5 in satisfactory yields.

The structures of Compounds 1-5 were all confirmed by combining various 1D and 2D NMR spectroscopy techniques, including 2D $^1$H-$^{13}$C HMQC and HMBC, 2D COSY, and 1D selective TOCSY experiments, along with mass spectrometry analysis.

The following describes the detailed syntheses of Compounds 1-5 and the intermediates thereof.

Preparation of Compound 4',6'-O-benzylidene-1,2', 3-triazido-paromamine (12)

Compound 11 (1 gram, 2.49 mmol) was dissolved in dry DMF (20 mL) and added with benzaldehyde dimethyl acetal (0.87 mL, 5.79 mmol) and a catalytic amount of CSA. The reaction was stirred at 60° C. and the reaction progress was monitored by TLC (EtOAc 60%, Hexane 40%), which indicated the completion of the reaction after 2 hours. The reaction mixture was diluted with EtOAc and extracted with saturated aqueous solutions of NaHCO₃ and NaCl. The combined organic layer was dried over MgSO₄, filtered and concentrated under reduced pressure. The crude product was purified by flash chromatography (EtOAc/hexane 1:1) to afford 12 (1.0 gram, 83% yield).

$^1$H NMR (500 MHz, MeOD): 'Ring I': δH=6.01 (d, 1H, J=3.6 Hz, H-1), 4.77 (dd, 1H, J=10.2, 5.1 Hz, H-6), 4.67-4.61 (m, 2H, H-3, H-6'), 4.24 (t, 1H, J=10.3 Hz, H-5), 4.02 (dd, 1H, J=9.5, 9.3 Hz, H-4), 3.83 (dd, 1H, J=10.2, 4.2 Hz, H-2)); 'Ring I': δH=4.02 (t, 1H, J=9.4 Hz, H-5), 3.91-3.76 (m, 4H, H-1, H-3, H-4, H-6), 2.77 (dt, 1H, J=12.7, 3.9 Hz, H-2 eq), 1.93 (ddd, 1H, J=12.3, 10.6, 7.0 Hz, H-2 ax); the additional peaks in the spectrum were identified as follow: 8.02-7.97 (m, 2H, Ar), 7.84 (dd, 2H, J=5.1, 1.9 Hz, Ar), 6.05 (s, 1H, phCH).

$^{13}$C NMR (125 MHz, MeOD): δ=C 137.58 (Ar), 129.54 (Ar), 128.56 (Ar), 126.70 (Ar), 102.41(phCH), 99.62(C-1'), 82.16, 81.33, 76.70, 76.50, 69.19(C-5'), 69.06(C-6'), 64.39, 63.59, 60.53, 59.66, 32.49(C-2).

MALDI TOFMS calcd for $C_{19}H_{24}N_9O_7$ ([M+H]+) m/e 490.4; measured m/e 490.0).

Preparation of 4,6'-O-benzylidene-3',5,6-tri-O-benzyl-1,2',3-triazido-paromamine (13)

To a stirred solution of compound 12 (1 gram, 2.04 mmol) in anhydrous DMF (20 mL), TBAI (1 gram, 2.70 mmol), HMPA (5 mL) and BnBr (1.45 mL, 12.19 mmol) were added. After stirring for 20 minutes, the mixture was cooled to −15° C. and NaH (0.5 gram, 12.5 mmol, 60% in oil) was added in portions. After being stirred for 30 min at −15° C., the mixture was allowed to warm to room temperature. The reaction progress was monitored by TLC (EtOAc 50%, Hexane 50%), which indicated completion after 1 hour. The reaction mixture was diluted with EtOAc and washed with water, 1M HCl, saturated aqueous NaHCO₃ and brine. The combined organic layer was dried over anhydrous MgSO₄, filtered and evaporated to dryness. The residue was purified by flash chromatography (EtOAc/hexane 1:5) to afford 13 (1.36 gram, 88% yield).

$^1$H NMR (500 MHz, CDCl₃): 'Ring I': δH=5.50 (d, 1H, J=4.0 Hz, H-1), 4.27 (dd, 1H, J=10.1, 5.0 Hz, H-6), 4.21 (td, 1H, J=9.8, 4.9 Hz, H-5), 4.06 (t, 1H, J=9.5 Hz, H-3), 3.71-3.62 (m, 2H, H-4, H-6), 3.29 (dd, 1H, J=10.0, 4.1 Hz, H-2); 'Ring II': δH=3.59-3.53 (m, 2H, H-4, H-5), 3.45 (ddd, 1H, J=12.4, 9.8, 4.3 Hz, H-1), 3.40-3.32 (m, 2H, H-3, H-6), 2.28 (dt, 1H, J=13.3, 4.5 Hz, H-2 eq), 1.44 (ddd, 1H, J=12.8 Hz, H-2ax); the additional peaks in the spectrum were identified as follow: 7.45 (dd, 2H, J=7.5, 1.7 Hz, Ph), 7.37-7.19 (m, 18H, Ph), 5.52 (s, 1H, Bn), 4.97 (d, 1H, J=10.7 Hz, Bn), 4.93 (d, 1H, J=11.0 Hz, Bn), 4.88 (d, 1H, J=10.7 Hz, Bn), 4.84 (d, 1H, J=10.5 Hz, Bn), 4.78 (d, 1H, J=10.5 Hz, Bn), 4.75 (d, 1H, J=11.0 Hz, Bn).

$^{13}$C NMR (125 MHz, CDCl₃): δ=C 138.11 (Ar), 137.94 (Ar), 137.42 (Ar), 129.17 (Ar), 128.65 (Ar), 128.63 (Ar), 128.55 (Ar), 128.42 (Ar), 128.38 (Ar), 128.28 (Ar), 128.19 (Ar), 128.01 (Ar), 127.79 (Ar), 127.19 (Ar), 126.21 (Ar), 101.56 (Bn-CH), 98.48 (C-1'), 84.82 (s), 84.46 (s), 82.72 (s), 78.05 (s), 76.39 (C-3'), 76.07 (Bn), 75.41 (Bn), 75.18 (Bn), 69.00 (C-6'), 63.27 (C-5'), 62.88 (C-2'), 60.37 (C-1), 59.36, 32.46 (C-2).

MALDI TOFMS calcd for $C_{40}H_{43}N_9O_7$ ([M+H]+) m/e 760.32; measured m/e 760.09).

Preparation of 3',5,6-tri-O-benzyl-1,2',3-triazido-paromamine (14)

Compound 13 (1.46 gram, 1.93 mmol) was dissolved in a mixture of acetic acid (10 mL) and water (2 mL). The reaction mixture was left to stirred at 50° C. overnight. The completion of the reaction was indicated by TLC (EtOAc 50%, Hexane 50%). The mixture was diluted with EtOAc and washed with saturated aqueous NaHCO₃ and brine. The combined organic layer was dried over anhydrous MgSO₄, filtered and evaporated to dryness. The residue was purified by flash chromatography (EtOAc/hexane 1:5) to afford 14 (1.2 gram, 90% yield).

$^1$H NMR (500 MHz, CDCl₃): 'Ring I': δH=5.58 (d, 1H, J=3.8 Hz, H-1), 3.99 (dt, 1H, J=9.9, 3.5 Hz, H-5), 3.84 (dd, 1H, J=10.0, 9.0 Hz, H-3), 3.79-3.76 (m, 2H, H-6, H-6'), 3.62 (ddd, 1H, J=9.6, 6.9, 3.7 Hz, H-4), 3.18 (dd, 1H, J=10.3, 3.8 Hz, H-2), 2.33 (d, 1H, J=3.6 Hz, OH-4), 1.81 (t, 1H, J=6.2 Hz, OH-6); 'Ring II': δ H=3.59-3.54 (m, 2H, H-4, H-5), 3.46 (ddd, 1H, J=12.4, 9.8, 4.5 Hz, H-1), 3.41-3.34 (m, 2H, H-3, H-6), 2.26 (dt, 1H, J=13.3, 4.6 Hz, H-2eq), 1.41 (ddd, 1H, J=12.7 Hz, H-2ax); the additional peaks in the spectrum were identified as follow: 7.35-7.22 (m, 15H, Ph), 4.99 (d, 1H, J=10.8 Hz, Bn), 4.90 (d, 1H, J=11.2 Hz, Bn), 4.86 (d, 1H, J=10.8 Hz, Bn), 4.83 (d, 1H, J=10.5 Hz, Bn), 4.78 (d, 1H, J=10.4 Hz, Bn), 4.73 (d, 1H, J=11.2 Hz, Bn).

$^{13}$C NMR (125 MHz, CDCl₃): δ=C 138.05 (Ar), 137.99 (Ar), 137.41 (Ar), 128.86 (Ar), 128.67 (Ar), 128.65 (Ar), 128.32 (Ar), 128.31 (Ar), 128.23 (Ar), 128.21 (Ar), 127.85 (Ar), 127.19 (Ar), 97.80 (C-1'), 84.77 (C-6), 84.62 (C-5), 80.12 (C-3'), 77.44 (C-4), 76.11 (Bn), 75.44 (Bn), 75.29 (Bn), 71.99 (C-5'), 70.88 (C-4'), 62.97 (C-2'), 62.15 (C-6'), 60.42 (C-1), 59.79 (C-3), 32.64 (C-2).

MALDI TOFMS calcd for $C_{33}H_{37}N_9O_7Na$ ([M+Na]+) m/e 694.27; measured m/e 694.03).

Preparation of 3',5,6-tri-O-benzyl-1,2',3,6'-tetraazido-paromamine (15)

Compound 14 (0.18 gram, 0.26 mmol) was treated with p-toluene sulfonyl chloride (2.37 grams, 12.4 mmol) in the presence of pyridine (20 mL) and 4-DMAP (1 gram, 0.81 mmol) and heated to 60° C. The reaction progress was monitored by TLC (EtOAc 30%, Hexane 70%), which indicated completion after 8 hours. Then the reaction mixture was diluted with EtOAc and washed with water, 1M HCl, saturated aqueous NaHCO₃ and brine. The combined organic layer was dried over anhydrous MgSO₄, filtered and evaporated to dryness. The tosylate intermediate was then mixed with sodium azide (2.37 grams, 12.4 mmol) and DMF (10 mL). After stirring at 60° C. for 18 hours, the reaction mixture was diluted 50 with EtOAc washed with water, 1M HCl, saturated aqueous NaHCO₃ and brine. The combined organic phase was dried over MgSO₄ and concentrated under vacuum. The crude was purified by column chromatography on silica gel (EtOAc/hexane 1:3) to afford 15 (0.12 gram, 68%).

¹H NMR (500 MHz, CDCl₃): 'Ring I': δH=5.59 (d, 1H, J=3.8 Hz, H-1), 4.16 (ddd, 1H, J=9.9, 4.6, 2.8 Hz, H-5), 3.80 (dd, 1H, J=10.1, 9.0 Hz, H-3), 3.53-3.47 (m, 2H, H-4, H-6), 3.43 (dd, 1H J=13.3, 4.9 Hz, H-6'), 3.22 (dd, 1H, J=10.3, 3.9 Hz, H-2), 2.08 (d, 1H, J=3.5 Hz, OH-4). 'Ring II': δH=3.64-3.54 (m, 2H, H-4, H-6), 3.50-3.42 (m, 1H, H-3), 3.43-3.35 (m, 2H, H-1, H-5), 2.28 (dt, 1H, J 13.2, 4.4, H-2eq), 1.45 (ddd, 1H, J 12.6, H-2ax); the additional peaks in the spectrum were identified as follow: 7.41-7.17 (m, 15H, Ar), 5.00 (d, 1H, J=0.9 Hz, Bn), 4.94 (d, 1H, J=11.3 Hz, Bn), 4.87 (d, 1H, J=10.9 Hz, Bn), 4.84 (d, 1H, J=10.4 Hz, Bn), 4.78 (d, 1H, J=10.4 Hz, Bn), 4.68 (d, 1H, J=11.3 Hz, Bn).

¹³C NMR (125 MHz, CDCl₃): δC=137.99 (Ar), 137.89 (Ar), 137.41 (Ar), 128.95 (Ar), 128.66 (Ar), 128.64 (Ar), 128.46 (Ar), 128.33 (Ar), 128.24 (Ar), 128.20 (Ar), 127.81 (Ar), 127.09 (Ar), 97.80 (C-1'), 84.78, 84.54, 80.19 (C-3'), 77.53, 76.12 (Bn), 75.38 (Bn), 75.31 (Bn), 71.33 (C-5'), 71.09, 62.93 (C-2'), 60.44, 59.66, 51.36 (C-6'), 32.55 (C-2).

MALDI TOFMS calcd for C₃₃H₃₆N₁₂O₆Na ([M+Na]+) m/e 719.2; measured m/e 719.05).

Preparation of 4'-O-Allyl-3',5,6-tri-O-benzyl-1,2',3,6'-tetraazido-paromamine (16)

Compound 15 (124 mg, 0.168 mmol) was dissolved in 10 mL of DMF and cooled to −10° C. The reaction was treated with sodium hydride (47 mg, 1.963 mmol, 60% in oil) followed by allyl bromide (0.1 mL, 1.15 mmol). The reaction progress was monitored by TLC (EtOAc 20%, Hexane 80%), which indicated completion after 1 hour. After completion the reaction mixture was diluted with EtOAc and washed with water, 1M HCl, saturated aqueous NaHCO₃ and brine. The combined organic layer was dried over anhydrous MgSO₄, filtered and evaporated to dryness. The residue was purified by flash chromatography (EtOAc/hexane 1:10) to afford 16 (127 mg, 97% yield).

¹H NMR (500 MHz, CDCl₃): 'Ring I': δH=5.54 (d, 1H, J=3.6 Hz, H-1), 4.21 (ddd, 1H, J=9.9, 4.0, 2.6 Hz, H-5), 3.91 (dd, 1H, J=10.1, 9.1 Hz, H-3), 3.52 (dd, 1H, J=13.4, 2.3 Hz, H-6), 3.40 (dd, 1H, J=13.3, 4.5 Hz, H-6'), 3.36 (dd, 1H, J=9.9, 9.0 Hz, H-4), 3.23 (dd, 1H, J=10.5, 4.3 Hz, H-2); 'Ring II': δH 3.60-3.53 (m, 2H, H-4, H-6), 3.47-3.41 (m, 1H, H-5), 3.40-3.34 (m, 2H, H-1, H-3), 2.26 (dt, J=13.3, 4.4 Hz, H-2aq), 1.45 (ddd, J=12.6 Hz, H-2ax); the additional peaks in the spectrum were identified as follow: 7.37-7.22 (m, 15H, Ar), 5.85 (ddd, 1H, J=22.6, 10.7, 5.6 Hz, Allyl), 5.23 (dd, 1H, J=17.2, 1.4 Hz, Allyl), 5.14 (dd, 1H, J=10.5, 1.2 Hz, Allyl), 4.98 (d, 1H J=10.9 Hz, Bn), 4.90 (d, 1H, J=10.8 Hz, Bn), 4.85-4.81 (m, 3H, Bn), 4.78 (d, 1H, J=10.4 Hz, Bn), 4.27 (dd, 1H, J=12.5, 5.5 Hz, Allyl), 4.08 (dd, 1H, J=12.5, 5.7 Hz, Allyl).

¹³C NMR (125 MHz, CDCl₃): δC=138.00 (Ar), 137.78 (Ar), 137.37 (Ar), 134.29 (Allyl), 128.56 (Ar), 128.53 (Ar), 128.25 (Ar), 128.15 (Ar), 128.10 (Ar), 127.99 (Ar), 127.69 (Ar), 127.00 (Ar), 117.41 (Allyl), 97.63 (C-1'), 84.69 (s), 84.41 (s), 79.92 (C-3'), 78.55 (s), 77.65 (s), 76.01 (Bn), 75.52 (Bn), 75.31 (Bn), 73.95 (Allyl), 71.08 (C-5'), 63.16 (C-2'), 60.31 (C-5), 59.42 (s), 51.08 (C-6'), 32.39 (C-2).

MALDI TOFMS calcd for C₃₆H₄₁N₁₂O₆([M+H]+) m/e 737.33; measured m/e 737.12).

Preparation of 4'-O-(2,3-dihydroxypropyl)-3',5,6-tri-O-benzyl-1,2',3,6'-tetraazido-paromamine (17)

To a solution of compound 16 (300 mg, 0.407 mmol) in a mixture of acetone:water (10:1) were added 4-methylmorpholine N-oxide (2 equiv, 0.814 mmol), and osmium tetroxide (0.02 equiv, 5 mg, 0.008 mmol). When the starting material had been consumed as monitored by TLC (EtOAc 20%, hexane 80%) the mixture was diluted with EtOAc and quenched with saturated aqueous sodium thiosulfate and brine. The combined organic phases were dried over anhydrous MgSO₄, filtered and evaporated to dryness. The residue was purified by column chromatography (EtOAc/hexane 55:45) to afford 17 (245 mg, 80% yield) as a mixture of two diastereomers.

¹H NMR (500 MHz, CDCl₃): 'Ring I': δH=5.59 (s, 1H, H-1), 4.21 (t, 1H J=10.9 Hz, H-5), 3.97-3.90 (m, 1H, H-3), 3.58 (d, 1H, J=12.4 Hz, H-6), 3.47 (d, 1H, J=13.1 Hz, H-6'), 3.41 (dd, 1H, J=16.7, 9.3 Hz, H-4), 3.27 (dd, 1H, J=10.9, 6.2 Hz, H-2); 'Ring II': δH=3.66-3.56 (m, 2H, H-4, H-5), 3.56-3.46 (m, 1H, H-1), 3.46-3.35 (m, 2H, H-3, H-6), 2.39-2.28 (m, 1H, H-2eq), 1.49 (ddd, 1H, J=12.6 Hz, H-2ax); the additional peaks in the spectrum were identified as follow: 7.45-7.19 (m, 15H, Ar), 5.03 (d, 1H, J=11.0 Hz, PHJH), 4.93-4.85 (m, 3H, PHJH), 4.82 (d, 2H, J=10.6 Hz, PHJH), 3.85 (d, J=9.7 Hz,), 3.78 (d, J=4.9 Hz), 3.69 (t, J=6.6 Hz), 3.64-3.56 (m), 3.52 (d, J=7.1 Hz), 2.89-2.78 (m), 2.63-2.56 (m), 1.88 (d, J=26.9 Hz).).

¹³C NMR (125 MHz, CDCl₃): δC=137.75 (Ar), 137.33 (Ar), 137.14 (Ar), 128.47 (Ar), 128.46 (Ar), 128.43 (Ar), 128.41 (Ar), 128.09 (Ar), 128.06 (Ar), 127.97 (Ar), 127.57 (Ar), 126.78 (Ar), 97.46 (C-1'), 84.54, 84.21, 79.77 (C-3'), 79.20, 77.52, 77.46, 75.88, 75.52, 75.35, 75.15, 74.54, 74.30, 71.07 (C-5'), 63.39 (CH₂), 63.24 (C-2'), 60.16, 59.34 (C-4'), 50.87 (C-6'), 32.28 (C-2).

MALDI TOFMS calcd for C₃₆H₄₂N₁₂NaO₈ ([M+Na]+) m/e 793.31; measured m/e 793.51).

Preparation of 4'-O-(2-aminoethylazido)ethyl-3',5,6-tri-O-benzyl-1,2',3,6'-tetraazido-paromamine (18)

To a solution of diol 17 (400 mg, 0.519 mmol) in anhydrous DCM (30 mL) was added PhI(OAc)₂ (1.2 equiv, 200 mg, 0.621 mmol) at room temperature under Argon. After stirring for 2 hours 2-azidoethanamine (2.6 equiv, 0.15 ml, 1.35 mmol) was added. The reaction mixture was stirred for 30 min before sodium triacetoxyborohydride (2.8 equiv, 0.84 mmol, 1.453 mmol) was added at room temperature. The reaction progress was monitored by TLC (EtOAc 50%, Hexane 50%), which indicated completion after 3 hours. After completion the reaction, the mixture was diluted with EtOAc and washed with saturated aqueous sodium bicarbonate and brine. The combined organic phases were dried over anhydrous MgSO$_4$, filtered and evaporated to dryness. The residue was purified by column chromatography (EtOAc/hexane 1:1) to afford 18 (280 mg, 66% yield).

$^1$H NMR (500 MHz, CDCl$_3$): 'Ring I': δH=5.57 (d, 1H, J=2.9 Hz, H-1), 4.23 (br d, 1H, J=9.9 Hz, H-5), 3.92 (t, 1H, J=9.5 Hz, H-3), 3.58 (d, 1H, J=12.9 Hz, H-6), 3.49 (dd, 1H, J=13.3, 3.7 Hz, H-6'), 3.38 (dd, 1H, J=9.7, 9.2 Hz, H-4), 3.28 (dd, 1H, J=10.6, 5.2 Hz, H-2); 'Ring II': δH=3.64-3.57 (m, 2H, H-4, H-5), 3.53-3.47 (m, 1H, H-3), 3.46-3.40 (m, 2H, H-1, H-6) 2.33 (dt, 1H, J=13.2, 4.5 Hz, H-2eq), 1.50 (ddd, 1H, J=12.6 Hz, H-2ax); the additional peaks in the spectrum were identified as follow: 7.46-7.23 (m, 15H, Ar), 5.02 (d, 1H, J=10.9 Hz, Bn), 4.93 (d, 1H, J=10.9 Hz, Bn), 4.91-4.85 (m, 3H, J=8.1 Hz, Bn), 4.82 (d, 1H, J=10.5 Hz, Bn), 3.93-3.87 (m, 1H, CH$_2$), 3.72-3.67 (m, 1H, CH2), 3.40-3.36 (m, 2H, CH$_2$), 2.78-2.75 (m, 4H, CH2).).

$^{13}$C NMR (125 MHz, CDCl$_3$): δC=138.04 (Ar), 137.84 (Ar), 137.40 (Ar), 128.63 (Ar), 128.62 (Ar), 128.31 (Ar), 128.17 (Ar), 128.05 (Ar), 127.76 (Ar), 127.03 (Ar), 97.70 (C-1'), 84.76, 84.45, 79.95 (C-3'), 79.19, 77.72, 76.08, 75.47, 75.37, 72.36 (CH$_2$), 71.10 (C-5'), 63.30 (C-2'), 60.37, 59.48, 51.30, 51.15, 49.37 CH$_2$), 48.45 (CH$_2$), 32.47 (C-2).

MALDI TOFMS calcd for C$_{37}$H$_{45}$N$_{16}$O$_6$ ([M+H]+) m/e 808.36; measured m/e 809.10).

Preparation of 4'-O-(2-aminoethylamino)ethyl-paromamine (Compound 1; FIGS. 1 and 2A)

Compound 18 (2.2 grams, 3.242 mmol) was dissolved in a mixture of THF (10 mL) and aqueous NaOH (0.1M, 5 mL). This mixture was stirred at room temperature for 10 minutes, after which PMe$_3$ (1M solution in THF, 38.91 mL, 38.91 mmol) was added. Propagation of the reaction was monitored by TLC [CH$_2$Cl$_2$/MeOH/H$_2$O/MeNH$_2$ (33% solution in EtOH), 10:15:6:15], which indicated completion after 3 hour. The reaction mixture was purified by flash chromatography on a short column of silica gel. The column was washed with the following solvents: hexane (200 mL), THF (200 mL), CH$_2$Cl$_2$ (200 mL), EtOAc (200 mL), MeOH (400 mL). The product was eluted with the mixture of 20% MeNH$_2$ solution (33% solution in EtOH) in 80% MeOH.

Fractions containing the product were combined and evaporated under vacuum. THF (10 mL) was added via syringe to a dry three neck flask equipped with a Dewar condenser. Then ammonia (about 20 mL) was condensed into the reaction vessel. Small pieces of Na (300 mg, 13 mmol) were then allowed to dissolve in the ammonia for 15 minutes. Then a solution of the aminoglycoside (from the above step) in a mixture of EtOH and THF (500 μL each) was added in one portion and washed down with THF. The reaction was stirred until the blue color was discharged. Then an aqueous solution of ammonium formate (1 gram, 15.7 mmol) was added, and the ammonia was allowed to evaporate. The remaining solvent was removed in Vacuum, and the residue was loaded onto a short column of silica gel. The column was washed with the following solvents: hexane (200 mL), THF (200 mL), CH$_2$Cl$_2$ (200 mL), EtOAc (200 mL), MeOH (400 mL). The product was eluted with the mixture of 20% MeNH$_2$ solution (33% solution in EtOH) in 80% MeOH. Fractions containing the product were combined and evaporated under vacuum. The product was then dissolved in small volume of water and loaded on a column of Amberlite CG-50 cation exchange resin (0.5 cm×10 cm) in its NH$_4^+$ form, washed with methanol (200 mL) and eluted with a linear gradient of 0% to 10% NH$_4$OH solution. The product containing fractions were combined and evaporated under vacuum to afford 1 (727 mg, 65%).

The product was converted to its sulfate salt form as follow: the free base was dissolved in water, the pH was adjusted to about 7 with H$_2$SO$_4$ (0.1 N) and lyophilized.

$^1$H NMR (500 MHz, D$_2$O): 'Ring I': δH=6.05 (d, 1H, J=3.8 Hz, H-1), 4.36 (dd, 1H, J=10.9, 8.8 Hz, H-3), 4.20 (dd, 1H, J=9.5, 6.4 Hz, H-5), 3.55 (dd, 1H, J=13.2, 2.7 Hz, H-6), 3.50 (dd, 1H, J=10.9, 4.7 Hz, H-2), 3.43 (dd, 1H, J=9.2, 9.2 Hz, H-4), 3.27 (dd, 1H, J=13.3, 9.0 Hz, H-6'); 'Ring II': δH=4.08 (dd, 1H, J=10.1, 9.4 Hz, H-4), 3.75 (dd, 1H, J=9.2, 9.2 Hz, H-5), 3.65 (dd, 1H, J=10.4, 9.3 Hz, H-6), 3.61-3.53 (m, 1H, H-3), 3.43-3.31 (m, 1H, H-1), 2.52 (dt, 1H, J=12.4, 4.1 Hz, H-2eq), 2.04 (ddd, 1H, J=12.6 Hz, H-2ax); The additional peaks in the spectrum were identified as follow: 4.25-4.17 (m, 1H, CH$_2$), 4.01 (dt, 1H, J=9.5, 4.5 Hz, CH$_2$), 3.51-3.48 (m, 4H, CH2), 3.39 (t, 2H, J=4.9 Hz, CH2).

$^{13}$C NMR (125 MHz, MeOD): δC=94.66 (C-1'), 79.09, 76.22 (C-4), 75.20 (C-5), 72.44 (C-6), 68.42 (C-3'), 68.18 (C-5'), 67.16 (CH$_2$), 53.39, 49.72, 48.46, 48.07 (CH$_2$), 44.58 (CH$_2$), 40.49 (C-6'), 35.64 (CH$_2$), 28.09 (C-2).

TOFMS calcd for C$_{16}$H$_{37}$N$_6$O$_6$ ([M+H]+) m/e 409.28; measured m/e 409.09).

Preparation of 1,2',2''',3,6'''-pentaazido-paromomycin (19)

Commercially available paromomycin sulfate was neutralized by passing through Dowex 50W resin column (H$^+$ form). Then, the free base (45.5 grams, 73.98 mmol) was dissolved in a mixture of MeOH (1 L) and H$_2$O (100 mL) and stirred. To the fully dissolved mixture, CuSO$_4$ (1.28 gr, 8 mmol), K$_2$CO$_3$ (114.6 grams, 830 mmol) and imidazole sulfonyl azide hydrochloride (86.9 grams, 1.2 eq. per amine, 416 mmol) were added. The color of the mixture changed from blue to dark green during the reaction. The reaction progress was monitored by TLC (CH$_2$Cl$_2$/MeOH/H$_2$O/ MeNH$_2$, 10:15:6:15) which indicated completion after 18 hours. The reaction mixture was evaporated, dissolved in MeOH (300 mL) and EtOAc (100 mL) and filtered. Then, the solvent was evaporated and the crude was dissolved in a minimum volume of H$_2$O, the pH was adjusted to 3 with HC (3M) and then extracted with EtOAc. The combined organic layers were dried over MgSO$_4$ and concentrated under reduced pressure to yield compound 19 (35 grams, 70%) as a white solid.

$^1$H NMR (500 MHz, MeOD): 'Ring I': δH=5.76 (d, 1H, J=3.1 Hz, H-1), 3.92-3.86 (m, 2H, H-3, H-5), 3.78 (dd, 1H, J=11.9, 1.6 Hz, H-6), 3.69 (dd, 1H, J=12.0, 4.3 Hz, H-6'), 3.35 (dd, 1H, J=10.1, 8.7 Hz, H-4), 3.03 (dd, 1H, J=10.7, 4.9 Hz, H-2); 'Ring II': δH=3.72-3.62 (m, 2H, H-4, H-5), 3.49-3.41 (m, 2H, H-3, H-6), 3.41-3.34 (m, 1H, H-1), 2.13 (dt, 1H, J=12.0, 4.0 Hz, H-2eq), 1.33 (ddd, 1H, J=13.5 Hz, H-2ax); 'Ring III': δH=5.35 (d, 1H, J=1.6 Hz, H-1), 4.40 (dd, 1H, J=7.4, 3.9 Hz, H-3), 4.26 (dd, 1H, J=4.8, 1.3 Hz, H-2), 4.09 (ddd, 1H, J=4.5, 3.3, 1.7 Hz, H-4), 3.78 (dd, 1H, J=12.1, 2.4 Hz, H-5), 3.65 (dd, 1H, J=11.0, 3.9 Hz, H-5'); 'Ring IV': δH 5.08 (d, 1H, J=1.51 Hz, H-1), 3.98-3.96 (m, 1H, H-5), 3.90-3.88 (m, 1H, H-3), 3.63 (dd, 1H, J=4.8, 0.5 Hz, H-3), 3.60 (m, 1H, H-6) 3.40 (d, 1H, J=2.3 Hz, H-4), 3.35(m, 1H, H-6').

$^{13}$C NMR (125 MHz, MeOD): δC=108.95(C-1''), 99.79 (C-1'''), 98.03(C-1'), 85.30(C-5), 83.50(C-4'''), 77.11(C-3''), 77.01(C-6), 76.31(C-4), 75.56(C-5'''), 75.21(C-2''), 74.14 (C-5'), 72.22(C-3'), 71.93(C-4'), 71.17(C-3'''), 69.60(C-4''), 64.66(C-2'), 63.28(C-5''), 62.48(C-6'), 61.85(C-2'''), 61.83 (C-1), 61.53(C-3), 52.44(C-6'''), 33.06(C-2).

TOFMS calcd for $C_{23}H_{35}N_{15}O_{14}Na$ ([M+Na]+) m/e 768.61; measured m/e 768.88).

Preparation of 4',6'-O-benzylidene-1,2',2''',3,6'''-pentaazido-paromamine (20)

The titled compound was prepared as was described for the preparation of compound 12 with the following quantities: compound 19 (0.6 gram, 0.805 mmol), DMF (10 mL), benzaldehyde dimethyl acetal (0.25 mL, 1.7 mmol), catalytic amount of camphorsulfonic acid to yield 20 (0.57 gram, 88%).

$^1$H NMR (500 MHz, MeOD): 'Ring I': δH=5.87 (d, 1H, J=3.6 Hz, H-1), 4.26 (dd, 1H, J=10.0, 5.0 Hz, H-6), 4.22-4.13 (m, 2H, H-3, H-6'), 3.80 (t, 1H, J=10.1 Hz, H-5), 3.59 (dd, 1H, J=9.6, 9.2 Hz, H-4), 3.29 (dd, 1H, J=10.3, 4.3 Hz, H-2); 'Ring II': δH 3.77-3.67 (m, 2H, H-4, H-5), 3.59-3.52 (m, 1H, H-3), 3.51-3.43 (m, 2H, H-1, H-6), 2.26 (dt, 1H, J=8.1, 4.0 Hz, H-2eq), 1.45 (ddd, 1H, J=12.7 Hz, H-2ax); 'Ring III': δH=5.43 (d, 1H, J=1.9 Hz, H-1), 4.47 (dd, 1H, J=7.0, 4.2 Hz, H-3), 4.36 (dd, 1H, J=4.8, 1.6 Hz, H-2), 4.19 (dt, 1H, J=4.9, 2.5 Hz, H-4), 3.88 (dd, 1H, J 12.0, 2.5 Hz, H-5), 3.73 (dd, 1H, J 12.0, 5.4 Hz, H-5'); 'Ring IV': δH=5.18 (d, 1H, J=2.4 Hz, H-1), 4.08-4.04 (m, 1H, H-5), 3.98 (t, 1H, J=3.3 Hz, H-3), 3.72 (t, 1H, J=2.5 Hz, H-2), 3.71 (dd, 1H, J=14.1, 8.4 Hz, H-6), 3.48 (t, 1H, J=2.5 Hz, H-4), 3.43 (dd, 1H, J=12.2, 4.2 Hz, H-6'); The additional peaks in the spectrum were identified as follow: 7.55-7.52 (m, 2H, Ar), 7.40-7.36 (m, 3H, Ar), 5.63 (s, 1H, PhCH).

$^{13}$C NMR (125 MHz, MeOD): δC=139.09 (Ar), 129.97 (Ar), 129.06 (Ar), 127.55 (Ar), 109.66 (C-1''), 103.09 (PhCH), 99.75(C-1'''), 99.12(C-1'), 85.19(C-5), 83.42(C-4''), 82.92(C-4'), 77.72(C-6), 77.24(C-4), 77.21(C-3''), 75.60(C-5'''), 75.10(C-2''), 71.11(C-3'''), 69.79(C-6'), 69.58(C-3'), 69.53(C-4'''), 65.14(C-2'), 64.54(C-5'), 63.63(C-5''), 61.83 (C-2'''), 61.77(C-1), 61.24(C-3), 52.45(C-6'''), 32.96(C-2).

TOFMS calcd for $C_{30}H_{39}N_{15}O_{14}Na$ ([M+Na]+) m/e 856.27; measured m/e 856.39).

Preparation of 4',6'-O-benzylidene-2'',3',3''',4''',5'',6-hexa-O-benzyl-1,2',2''',3,6'''-pentaazido-paromomycin (21)

The titled compound was prepared as was described for the preparation of compound 13 with the following quantities: compound 20 (1 gram, 1.2 mmol), DMF (10 mL), TBAI (0.5 gram, 1.35 mmol), HMPA (3 mL, 17.2 mmol), BnBr (1.7 mL, 14.3 mmol, 2 eq. per hydroxyl), NaH (0.6 gram, 60% in oil, 25 mmol, 2 eq. per hydroxyl) to yield 21 (1.1 grams, 60%).

$^1$H NMR (500 MHz, CDCl$_3$): 'Ring I': δH=6.18 (d, 1H, J=3.3 Hz, H-1), 4.33 (dd, 1H, J=10.2, 4.8 Hz, H-6), 4.13-4.05 (m, 2H, H-3, H-5), 3.66 (dd, 1H, J=10.2 Hz, H-6'), 3.44 (dd, 1H, J=9.9, 8.9 Hz, H-4), 3.08 (dd, 1H, J=10.1, 4.9 Hz, H-2); 'Ring II': δH 3.95 (dd, 1H, J=11.1, 6.6 Hz, H-5), 3.67 (dd, 1H, J=11.1, 6.2 Hz, H-4), 3.49-3.40 (m, 2H, H-1, H-3), 3.30 (dd, 1H, J=9.5 Hz, H-6), 2.25 (dt, 1H, J=12.6, 4.3 Hz, H-2eq), 1.41 (ddd, 1H, J=12.9 Hz, H-2ax); 'Ring III': δH=5.67 (d, 1H, J=4.9 Hz, H-1), 4.32-4.28 (m, 2H, H-3, H-4), 3.96 (dd, 1H, J=9.3, 3.9 Hz, H-2), 3.83 (dd, 1H, J=10.8, 2.2 Hz, H-5), 3.58 (dd, 1H, J=10.8, 3.0 Hz, H-5'); 'Ring IV': δH=4.88 (d, 1H, J=1.5 Hz, H-1), 3.79-3.76 (m, 1H, H-5), 3.69-3.63 (m, 2H, H-3, H-6), 3.35 (dd, 1H, J=2.7, 1.2 Hz, H-2), 3.13 (dd, 1H, J=3.7, 1.3 Hz, H-4), 2.91-2.87 (m, 1H, H-6'); The additional peaks in the spectrum were identified as follow: 7.51-7.13 (m, 35H, Ar), 5.51(s, 1H, PhCH), 4.96 (d, 1H, J 10.7, PhCH$_2$), 4.91(d, 1H, J=11.3, PhCH$_2$), 4.78 (d, 1H, J=11.3, PhCH$_2$), 4.73 (d, 1H, J=10.7, PhCH$_2$), 4.63 (d, 1H, J=12.0, PhCH$_2$), 4.60 (d, 2H, J=11.2, PhCH$_2$), 4.54 (d, 1H, J=12.8, PhCH$_2$), 4.47 (d, 1H, J=11.8, PhCH$_2$), 4.45 (d, 1H, J=11.8, PhCH$_2$), 4.42 (d, 1H, J=12.0, PhCH$_2$), 4.27 (d, 1H, J=12.0, PhCH$_2$).

$^{13}$C NMR (125 MHz, CDCl$_3$): δC=138.36 (Ar), 138.10 (Ar), 137.90 (Ar), 137.60 (Ar), 137.43 (Ar), 137.04 (Ar), 136.96 (Ar), 128.69-126.11 (Ar), 106.25 (C1''), 101.39 (PhCH), 98.60 (C-1'''), 96.50 (C-1'), 84.14 (C-6), 82.42 (C-2''), 82.13 (C-4'), 82.11 (C-4''), 81.85 (C-5), 75.98 (C-3'), 75.51 (C-3''), 75.42 (C-4), 75.03, 74.90, 74.39 (C-5'''), 73.26 (PhCH$_2$), 73.20 (PhCH$_2$), 72.96 (C-3'''), 72.42 (PhCH$_2$), 71.77 (PhCH$_2$), 71.60 (C-4'''), 70.37 (C-5''), 69.0 (C-6'), 62.97 (C-5'), 62.87 (C-2'), 60.34 (C-1), 59.87 (C-3), 57.31 (C-2'''), 51.14 (C-6'''), 32.39 (C-2).

TOFMS calcd for $C_{72}H_{75}N_{15}O_{14}Na$ ([M+Na]+) m/e 1396.55; measured m/e 1396.55).

Preparation of 2'',3',3''',4''',5'',6-hexa-O-benzyl-1,2',2''',3,6'''-pentaazido-paromomycin (22)

The titled compound was prepared as was described for the preparation of compound 14 with the following quantities: compound 21 (36 grams, 26.20 mmol), Acetic acid (240 mL), Water (50 mL) to yield 22 (20.5 grams, 61%).

$^1$H NMR (500 MHz, CDCl$_3$): 'Ring I': δH=6.27 (d, 1H, J=3.1 Hz, H-1), 4.00-3.93 (m, 2H, H-3, H-5), 3.87 (ddd, 1H, J=10.8, 2.7, 1.5 Hz, H-6), 3.83-3.77 (m, 1H, H-6'), 3.51-3.45 (m, 1H, H-4), 2.95 (dd, 1H, J=10.4, 5.0 Hz, H-2), 2.29-2.27 (m, 1H, OH-6), 1.72-1.67 (m, 1H, OH-4); 'Ring II': δH=4.06 (dd, 1H, J=8.8 Hz, H-5), 3.72 (dd, 1H, J=9.2 Hz, H-4), 3.57-3.49 (m, 2H, H-1, H-3), 3.39 (dd, 1H, J=9.4 Hz, H-6), 2.32 (dt, 1H, J 13.3, 4.5 Hz, H-2eq), 1.48 (q, 1H, J=12.7 Hz, H-2ax); 'Ring III': H=5.79 (d, 1H, J=5.1 Hz, H-1), 4.42-4.40 (m, 2H, H-3, H-4), 4.08 (dd, 1H, J=6.4, 5.1 Hz, H-2), 3.93 (dd, 1H, J=9.9, 0.9 Hz, H-5), 3.68 (dd, 1H, J=9.4, 1.0 Hz, H-5'); 'Ring IV': δH 5.00 (d, 1H, J=2.5 Hz, H-1), 3.90-3.84 (m, 2H, H-3, H-5), 3.76 (dd, 1H, J=12.8, 8.1 Hz, H-6), 3.46-3.44 (m, 1H, H-2), 3.22-3.21 (m, 1H, H-4), 2.99-2.94 (m, 1H, H-6'); the additional peaks in the spectrum were identified as follow: 7.47-7.23 (m, 30H, Ar), 5.08 (d, 1H, J=10.6 Hz, PhCH$_2$), 5.01 (d, 1H, J=14.7 Hz, PhCH$_2$), 4.81 (d, 1H, J=10.6 Hz, PhCH$_2$), 4.76 (d, 1H, J=11.4 Hz, PhCH$_2$), 4.71 (d, 1H, J=12.1 Hz, PhCH$_2$), 4.68 (d, 1H, J=11.8 Hz, PhCH$_2$), 4.58-4.55 (m, 2H, PhCH$_2$), 4.50 (d, 1H, J=12.0 Hz, PhCH$_2$), 4.42-4.39 (m, 2H, PhCH$_2$), 4.34 (d, 1H, J=12.1 Hz, PhCH$_2$).

$^{13}$C NMR (151 MHz, CDCl$_3$): δC=138.39 (Ar), 138.19 (Ar), 138.02 (Ar), 137.62 (Ar), 137.08 (Ar), 137.02 (Ar), 128.80 (Ar), 128.79 (Ar), 128.63 (Ar), 128.54 (Ar), 128.46 (Ar), 128.41 (Ar), 128.38 (Ar), 128.33 (Ar), 128.25 (Ar), 128.21 (Ar), 127.95 (Ar), 127.93 (Ar), 127.90 (Ar), 127.84 (Ar), 127.68 (Ar), 127.61 (Ar), 127.23 (Ar), 106.23 (C-1''), 98.78 (C-1'''), 96.03 (C-1'), 84.41 (C-6), 82.67 (C-2''), 82.29 (C-4''), 82.11 (C-5), 79.77 (C-3'), 75.61 (C-3''), 75.19 (PhCH$_2$), 75.07 (PhCH$_2$), 74.94 (C-4), 74.56 (C-5'''), 73.34 (PhCH$_2$), 73.28 (PhCH$_2$), 72.92 (C-3'''), 72.48 (PhCH$_2$), 71.70 (C-5'), 71.55 (C-4'''), 70.50 (C-4'), 70.39 (C-5''), 62.74 (C-6'), 62.19 (C-2'), 60.47 (C-1), 60.37 (C-3), 57.35 (C-2'''), 51.26 (C-6'''), 32.66 (C-2).

TOFMS calcd for $C_{65}H_{71}N_{15}O_{14}Na$ ([M+Na]+) m/e 1308.52; measured m/e 1308.00).

Preparation of 2'',3',3''',4''',5'',6-hexa-O-benzyl-1,2',2''',3,6',6'''-hexaazido-neomycin (23)

The titled compound was prepared as was described for the preparation of compound 15 with the following quantities: compound 22 (26.3 grams, 20.45 mmol), pyr (130 mL), Trisyl chloride (instead of tosyl chloride, 31.5 grams, 104.00 mmol), NaN$_3$ (9.45 grams, 145.38 mmol), DMF (100 mL), HMPA (30 mL) to yield 23 (16 grams, 60%). 1H NMR (500 MHz, CDCl$_3$): 'Ring I': δH=6.21 (d, 1H, J=2.4 Hz, H-1), 4.04 (dd, 1H, J=9.4, 3.9 Hz, H-5), 3.84 (t, 1H, J=9.6 Hz, H-3), 3.49 (dd, 1H, J=13.6, 1.8 Hz, H-6), 3.33 (dd, 1H, J=13.2, 6.5 Hz, H-6'), 3.26-3.20 (m, 1H, H-4), 2.90 (dd, 1H, J=10.4, 5.3 Hz, H-2); 'Ring II': δH=3.97 (t, 1H, J=9.0 Hz, H-5), 3.69 (t, 1H, J=9.3 Hz, H-4), 3.55-3.39 (m, 2H, H-1, H-3), 3.31 (t, 1H, J=9.0 Hz, H-6), 2.25 (dt, 1H, J=13.2, 4.5 Hz, H-2eq), 1.43 (ddd, 1H, J=12.7 Hz, H-2ax); 'Ring III': δH=5.69 (d, 1H, J=5.2 Hz, H-1), 4.30-4.25 (m, 2H, H-3, H-4), 3.99-3.91 (m, 1H, H-2), 3.84-3.80 (m, 1H, H-5), 3.57 (dd, 1H, J=10.4, 2.8 Hz, H-5'); 'Ring IV': δH=4.93 (d, 1H, J=2.5 Hz, H-1), 3.83-3.71 (m, 2H, H-3, H-5), 3.70-3.62 (m, 1H, J=12.8, 8.1 Hz, H-6), 3.36 (s, 1H, H-2), 3.14-3.12 (m, 1H, H-4), 2.89-2.86 (m, 1H, H-6'); the additional peaks in the spectrum were identified as follow: 7.42-7.12 (m, 30H, Ar), 4.72 (d, 1H, J=10.6 Hz, PhCH$_2$), 4.63 (d, 1H, J=6.1 Hz, PhCH$_2$), 4.61 (d, 2H, J=5.7 Hz, PhCH2), 4.52 (d, 1H, J=11.9 Hz, PhCH$_2$), 4.47 (dd, 2H, J=11.8, 5.2 Hz, PhCH$_2$), 4.42 (d, 1H, J=12.0 Hz, PhCH$_2$), 4.32 (d, 1H, J=12.0 Hz, PhCH$_2$), 4.30-4.23 (m, 3H, PhCH$_2$).

$^{13}$C NMR (125 MHz, CDCl$_3$): δC=138.21 (Ar), 137.88 (Ar), 137.59 (Ar), 136.96 (Ar), 136.90 (Ar), 128.77 (Ar), 128.68 (Ar), 128.50 (Ar), 128.44 (Ar), 128.38 (Ar), 128.33 (Ar), 128.25 (Ar), 128.19 (Ar), 128.16 (Ar), 127.82 (Ar), 127.78 (Ar), 127.75 (Ar), 127.46 (Ar), 127.27 (Ar), 106.00 (C-1"), 98.59 (C-1'''), 95.75 (C-1'), 84.35 (C-6), 82.56 (C-2"), 82.07 (C-4"), 81.70 (C-5), 79.74 (C-3'), 75.49 (C-3"), 75.09 (PhCH$_2$), 74.89 (PhCH$_2$), 74.42 (C-4), 73.34 (C-5'''), 73.21 (PhCH$_2$), 72.70 (PhCH$_2$), 72.31 (C-3'''), 71.62 (PhCH$_2$), 71.32 (C-5'), 71.19 (C-4'''), 70.93 (C-4'), 70.19 (C-5"), 62.53 (C-2'''), 60.34 (C-2'), 60.13 (C-1), 57.18 (C-3), 51.55 (C-6'), 51.06 (C-6'''), 32.56 (C-2).

TOFMS calcd for C$_{65}$H$_{70}$N$_{18}$O$_{13}$Na ([M+Na]+) m/e 1333.54; measured m/e 1333.53).

Preparation of 4'-O-Allyl-2''',3',3''',4''',5'',6-hexa-O-benzyl-1,2',2''',3,6',6'''-hexaazido-neomycin (24)

The titled compound was prepared as was described for the preparation of compound 16 with the following quantities: compound 23 (11 grams, 8.393 mmol), DMF (100 mL), NaH (60% in oil, 1 gram, 25.180 mmol), Allyl bromide (1.45 mL, 16.786 mL), TBAI (10 grams, 27.073 mmol) to yield 24 (10.5 grams, 92.6%).

$^1$H NMR (600 MHz, CDCl$_3$): 'Ring I': δH=6.14 (d, 1H, J=3.1 Hz, H-1), 4.12-4.06 (m, 1H, H-5), 3.95 (dd, 1H, J=10.0, 9.6 Hz, H-3), 3.50 (dd, 1H, J=12.8 Hz, H-6), 3.33 (dd, 1H, J=13.3, 6.0 Hz, H-6), 3.13 (dd, 1H, J=9.9, 9.2 Hz, H-4), 2.97 (dd, 1H, J=10.6, 5.0 Hz, H-2)); 'Ring II': δH=3.94 (dd, 1H, J=8.4 Hz, H-5), 3.66 (dd, 1H, J=9.2 Hz, H-4), 3.49-3.38 (m, 2H, H-1, H-3), 3.31 (dd, 1H, J=9.5, 8.6 Hz, H-6), 2.25 (dt, 1H, J=9.0, 5.0 Hz, H-2eq), 1.43 (ddd, 1H, J=12.8 Hz, H-2ax); 'Ring III': δH=5.66 (d, 1H, J=5.0 Hz, H-1), 4.28 (dt, 1H, J=3.0, 2.6 Hz, H-4), 4.25 (dd, 1H, J=4.1, 3.4 Hz, H-3), 3.95 (dd, 1H, J=6.0, 5.4 Hz, H-2), 3.79 (dd, 1H, J=9.8, 1.4 Hz, H-5), 3.56 (dt, 1H, J=6.3, 2.7 Hz, H-5'); 'Ring IV': δH 4.90 (d, 1H, J=1.7 Hz, H-1), 3.79-3.74 (m, 2H, H-3, H-5), 3.63 (dd, 1H, J=12.9, 9.0 Hz, H-6), 3.35 (dd, 1H, J=7.1, 2.0 Hz, H-2), 3.12 (dd, 1H, J=2.6, 1.3 Hz, H-4), 2.92-2.84 (m, 1H, H-6'); The additional peaks in the spectrum were identified as follow: 7.46-7.07 (m, 30H, Ar), 5.85 (m, 1H, Allyl), 5.24 (d, 1H, J=17.2 Hz, Allyl), 5.16 (d, 1H, J=10.6 Hz, Allyl), 4.95 (d, 1H, J=10.7 Hz, PhCH$_2$), 4.81 (d, 1H, J=10.8 Hz, PhCH$_2$), 4.78 (d, 1H, J=10.9 Hz, PhCH$_2$), 4.71 (d, 1H, J=10.6 Hz, PhCH$_2$), 4.62 (d, 1H, J=12.2 Hz, PhCH$_2$), 4.59 (d, 1H, J=12.1 Hz, PhCH$_2$), 4.53 (d, 1H, J=12.0 Hz, PhCH$_2$), 4.45 (d, 2H, J=11.5 Hz, PhCH$_2$), 4.42 (d, 1H, J=12.2 Hz, PhCH$_2$), 4.32 (d, 1H, J=12.0 Hz, PhCH2), 4.27 (m, 2H, PhCH$_2$, Allyl), 4.05 (dd, 1H, J=12.3, 5.7 Hz, Allyl).

$^{13}$C NMR (151 MHz, CDCl$_3$): δC=138.40 (Ar), 138.06 (Ar), 138.01 (Ar), 137.77 (Ar), 137.13 (Ar), 137.06 (Ar), 134.49 (Allyl), 128.79 (Ar), 128.61 (Ar), 128.53 (Ar), 128.50 (Ar), 128.49 (Ar), 128.44 (Ar), 128.38 (Ar), 128.29 (Ar), 128.22 (Ar), 127.94 (Ar), 127.90 (Ar), 127.86 (Ar), 127.58 (Ar), 127.55 (Ar), 117.27 (Allyl), 106.27 (C-1"), 98.70 (C-1'''), 95.63 (C-1'), 84.34 (C-6), 82.58 (C-2"), 82.16 (C-4"), 81.80 (C-5), 79.83 (C-3'), 78.66 (C-3"), 75.41 (PhCH$_2$), 75.19 (PhCH$_2$), 74.46 (C-4), 73.82 (Allyl), 73.39 (C-5'''), 73.42 (PhCH$_2$), 72.98 (PhCH$_2$), 72.48 (C-3'''), 71.93 (PhCH$_2$), 71.82 (C-5'), 71.58 (C-4'''), 71.07 (C-4'), 70.30 (C-5"), 63.13 (C-2'''), 60.48 (C-2'), 60.09 (C-1), 57.37 (C-3), 51.49 (C-6'), 51.17 (C-6'''), 32.60 (C-2).

TOFMS calcd for C$_{68}$H$_{74}$N$_{18}$O$_{13}$Na ([M+Na]+) m/e 1373.56; measured m/e 1373.43).

Preparation of 4'-O-(2,3-dihydroxypropyl)-2'',3',3'',4''',5'',6-hexa-O-benzyl-1,2',2''',3,6',6'''-hexaazido-neomycin (25)

The titled compound was prepared as was described for the preparation of compound 17 with the following quantities: compound 24 (0.5 gram, 0.370 mmol), (3.4 mL), water (0.3 mL), 4-methylmorpholine N-oxide (0.2 mL, 2 eq., 50% wt. in H$_2$O), osmium tetroxide (2 mg, 0.008 mmol, 0.02 eq.) to yield 25 (0.45 gram, 89%).

$^1$H NMR (500 MHz, CDCl$_3$): 'Ring I': δH=6.17 (d, 1H, J=3.3 Hz, H-1), 4.07-4.02 (m, 1H, H-5), 3.93 (dd, 1H, J=12.3, 7.1 Hz, H-3), 3.52 (dd, 1H, J=12.9, 1.3 Hz, H-6), 3.36 (dd, 1H, J=12.9, 5.4 Hz, H-6'), 3.16 (dd, 1H, J=18.0, 9.1 Hz, H-4), 2.91 (dd, 1H, J=12.0, 6.0 Hz, H-2); 'Ring II': δH=3.95 (dd, 1H, J=9.8, 8.8 Hz, H-5), 3.65 (dd, 1H, J=9.2 Hz, H-4), 3.50-3.41 (m, 2H, H-1, H-3), 3.31 (dd, 1H, J=10.4, 9.2 Hz, H-6), 2.25 (dt, 1H, J=13.0, 4.4 Hz, H-2eq), 1.42 (ddd, 1H, J=12.9 Hz, H-2ax); 'Ring III': δH=5.66 (d, 1H, J=4.7 Hz, H-1), 4.29-4.25 (m, 2H, H-3, H-4), 3.95 (dd, 1H, J=5.5 Hz, H-2), 3.80 (dd, 1H, J=10.0, 1.4 Hz, H-5), 3.56 (dd, 1H, J=10.2, 2.6 Hz, H-5'); 'Ring IV': δH=4.91 (d, 1H, J=2.0 Hz, H-1), 3.82-3.74 (m, 2H, H-3, H-5), 3.65 (dd, 1H, J=12.3, 8.7 Hz, H-6), 3.36 (dd, 1H, J=2.7, 1.2 Hz, H-2), 3.13 (dd, 1H, J=2.5, 1.8 Hz, H-4), 2.92 (dd, 1H, J=9.9, 2.9 Hz, H-6'); the additional peaks in the spectrum were identified as follow: 7.45-7.10 (m, 30H, Ar), 4.95 (d, 1H, J=10.5 Hz, PhCH2), 4.87 (d, 1H, J=10.7 Hz, PhCH$_2$), 4.73 (d, 1H, J=6.7 Hz, PhCH$_2$), 4.71 (d, 1H, J=6.8 Hz, PhCH$_2$), 4.62 (d, 1H, J=12.0 Hz, PhCH$_2$), 4.59 (d, 1H, J=11.8 Hz, PhCH$_2$), 4.52 (dd, 1H, J=11.9, 3.1 Hz, PhCH$_2$), 4.48-4.40 (m, 3H, PhCH$_2$), 4.32 (d, 1H, J=12.0 Hz, PhCH$_2$), 4.25 (d, 1H, J=12.1 Hz, PhCH$_2$), 3.76-3.62 (m, 3H, Diol), 3.62-3.55 (m, 1H, Diol), 3.52-3.46 (m, 1H, Diol), 3.01 (d, 1H, J=2.8 Hz, OH), 1.95-1.91 (m, 1H, OH).

$^{13}$C NMR (126 MHz, CDCl$_3$): δC=138.39 (Ar), 138.37 (Ar), 137.99 (Ar), 137.79 (Ar), 137.75 (Ar), 137.53 (Ar), 137.14 (Ar), 137.07 (Ar), 128.83 (Ar), 128.65 (Ar), 128.57 (Ar), 128.49 (Ar), 128.43 (Ar), 128.35 (Ar), 128.24 (Ar), 127.98 (Ar), 127.91 (Ar), 127.73 (Ar), 127.70 (Ar), 127.68 (Ar), 127.65 (Ar), 127.61 (Ar), 106.34 (C-1"), 98.75 (C-1'''), 95.79 (C-1'), 84.38 (C-6), 82.62 (C-5), 82.21 (C-2"), 81.88 (C-4"), 79.77, 79.65 (C-4'), 79.53 (C-3"), 75.67 (Diol), 75.59 (C-4), 75.35 (Diol), 75.26 (C-3"), 74.87, 74.54, 74.36 (C-5'''), 73.45, 73.00 (C-3'''), 72.53, 71.86, 71.61, 71.36

(C-4'''), 71.21, 71.06 (C-5'), 70.34 (C-5''), 63.60 (Diol), 63.25 (C-2'), 60.49 (C-1), 60.19 (C-3), 57.40 (C-2'''), 51.39 (C-6'''), 51.24 (C-6'), 32.64 (C-2).

TOFMS calcd for $C_{68}H_{76}N_{18}O_{15}Na$ ([M+Na]+) m/e 1407.57; measured m/e 1407.51).

Preparation of 4'-O-(2-aminoethylazido)ethyl-2'',3', 3''',4''',5'',6-hexa-O-benzyl-1,2',2''',3,6',6'''- hexaazido-neomycin (26)

The titled compound was prepared as was described for the preparation of compound 18 with the following quantities: compound 25 (700 mg, 0.505 mmol), DCM (30 mL), PhI(OAc)$_2$ (195 mg, 0.605 mmol, 1.2 eq.), 2-azidoethanamine (0.11 ml, 1.3 mmol, 2.6 eq), triacetoxyborohydride (300 mg, 1.42 mmol, 2.8 eq.) to yield 26 (450 mg, 62%).

$^1$H NMR (500 MHz, CDCl$_3$): 'Ring I': δH=6.14 (d, 1H, J=3.9 Hz, H-1), 4.10-4.03 (m, 1H, H-5), 3.92 (dd, 1H, J=10.3, 9.4 Hz, H-3), 3.52 (dd, 1H, J=12.8, 1.1 Hz, H-6), 3.37 (dd, 1H, J=13.2, 2.0 Hz, H-6'), 3.10 (dd, 1H, J=10.0, 9.2 Hz, H-4), 2.96 (dd, 1H, J=11.0, 2.7 Hz, H-2); 'Ring II': δH=3.92 (dd, 1H, J=9.0 Hz, H-5), 3.63 (dd, 1H, J=9.2 Hz, H-4), 3.48-3.37 (m, 2H, H-1, H-3), 3.28 (dd, 1H, J=8.9 Hz, H-6), 2.26 (dt, 1H, J=13.2, 4.5 Hz, H-2eq), 1.41 (ddd, 1H, J=13.0 Hz, H-2ax); 'Ring III': δH=5.66 (d, 1H, J=5.0 Hz, H-1), 4.33-4.23 (m, 2H, H—3, H-4), 3.95 (t, 1H, J=5.9 Hz, H-2), 3.79 (dd, 1H, J=10.4, 1.7 Hz, H-5), 3.56 (dd, 1H, J=10.5, 2.5 Hz, H-5'); 'Ring IV': δH=4.90 (d, 1H, J=1.2 Hz, H-1), 3.79-3.75 (m, 2H, H-3, H-5), 3.64 (dd, 1H, J=12.6, 9.1 Hz, H-6), 3.35 (d, 1H, J=4.6 Hz, H-2), 3.12 (s, 1H, H-4), 2.89 (dd, 1H, J=13.0, 4.0 Hz, H-6'); the additional peaks in the spectrum were identified as follow: δ 7.42-7.14 (m, 30H, Ar), 4.95 (d, 1H, J=10.6 Hz, PhCH$_2$), 4.83 (d, 1H, J=10.9 Hz, PhCH$_2$), 4.78 (d, 1H, J=10.8 Hz, PhCH$_2$), 4.72 (d, 1H, J=10.7 Hz, PhCH$_2$), 4.62 (d, 1H, J=12.0 Hz, PhCH$_2$), 4.59 (d, 1H, J=11.8 Hz, PhCH$_2$), 4.53 (d, 1H, J=11.9 Hz, PhCH$_2$), 4.45 (d, 2H, J=11.8 Hz, PhCH$_2$), 4.42 (d, 1H, J=11.9 Hz, PhCH$_2$), 4.32 (d, 1H, J=12.0 Hz, PhCH$_2$), 4.25 (d, 1H, J=12.2 Hz, PhCH$_2$), 3.88-3.83 (m, 1H, CH$_2$), 3.63-3.59 (m, 1H, CH$_2$), 3.35 (t, 2H, J=5.6 Hz, CH$_2$), 2.78-2.69 (m, 4H, CH$_2$).

$^{13}$C NMR (125 MHz, CDCl$_3$): δC=138.44 (Ar), 138.13 (Ar), 138.04 (Ar), 137.81 (Ar), 137.17 (Ar), 137.10 (Ar), 131.03 (Ar), 128.95 (Ar), 128.83 (Ar), 128.65 (Ar), 128.57 (Ar), 128.54 (Ar), 128.49 (Ar), 128.43 (Ar), 128.33 (Ar), 128.11 (Ar), 127.98 (Ar), 127.94 (Ar), 127.91 (Ar), 127.64 (Ar), 127.60 (Ar), 106.31 (C-1''), 98.75 (C-1'''), 95.76 (C-1'), 84.36 (C-6), 82.61 (C-5), 82.21 (C-2''), 81.85 (C-4''), 79.79 (C-3'), 79.36 (C-4'), 75.69, 75.29, 75.27 (C-3''), 75.23, 74.51 (C-5'''), 73.43 (CH$_2$), 73.03 (C-3'''), 72.53 (CH$_2$), 71.87, 71.63 (C-4'''), 71.14 (C-5'), 70.36 (C-5''), 68.31, 63.22 (C-2'), 60.52 (C-1), 60.14 (C-3), 57.42 (C-2'''), 51.51 (C-6'''), 51.22 (C-6'), 49.52 (CH$_2$), 48.66 (CH2), 38.88, 32.63 (C-2), 30.51, 29.85, 23.89, 23.13.

TOFMS calcd for $C_{69}H_{80}N_{20}O_{13}K$ ([M+K]+) m/e 1461.58; measured m/e 1461.51).

Figure 2B:
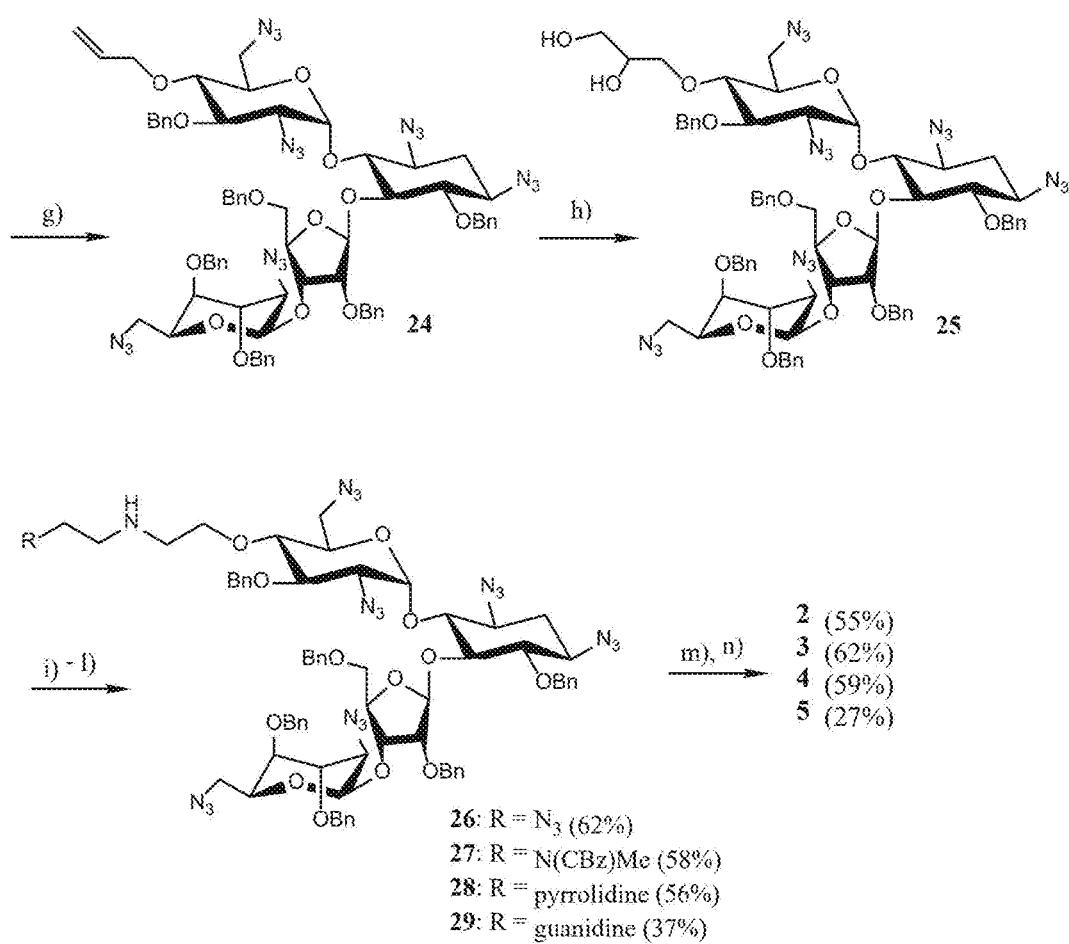

Preparation of 4'-O-(2-aminoethylamino)ethyl-neomycin (Compound 2; FIGS. 1 and 2): The titled compound was prepared as was described for the preparation of compound 1 with the following quantities: Staudinger reaction: compound 26 (400 mg, 0.281 mmol), THF (10 mL), aqueous NaOH (0.1M, 5 mL), PMe$_3$ (1M solution in THF, 6.7 mL, 6.7 mmol). Birch reduction: THF (10 mL), ammonia (about 20 mL), Na (150 mg, 7 mmol), ammonium formate (1 gran, 15.7 mmol). The analytically pure product was obtained by passing the above product through a short column of Amberlite CG50 (NH$_4^+$ form). The column was first washed with MeOH and H$_2$O, then the product was eluted with a mixture of H$_2$O/NH$_4$OH (95:5) to afford compound 2 (108 mg, 55% for two steps). For the storage and biological tests, compound 2 was converted to its sulfate salt form: the free base was dissolved in water, the pH was adjusted around 7.0 with H$_2$SO$_4$ (0.1 N) and lyophilized.

$^1$H NMR (500 MHz, MeOD): 'Ring I': δH=5.47 (d, 1H, J=3.7 Hz, H-1), 3.74-3.69 (m, 1H, H-5), 3.67 (dd, 1H, J=10.5, 9.1 Hz, H-3), 3.09 (dd, 1H, J=11.4, 1.3 Hz, H-6), 3.04 (dd, 1H, J=12.7, 1.8 Hz, H-6'), 2.75 (dd, 1H, J=9.7, 9.2 Hz, H-4), 2.71 (dd, 1H, J=10.5, 2.9 Hz, H-2); 'Ring II': δH=3.52 (dd, 1H, J=8.7 Hz, H-5), 3.45 (dd, 1H, J=8.5 Hz, H-4), 3.18-2.96 (m, 2H, H-1, H-3), 2.75 (dd, 1H, J=10.9, 8.4 Hz, H-6), 2.01-1.95 (m, 1H, H-2eq), 1.23 (ddd, 1H, J=10.9, 2.2 Hz, H-2ax); 'Ring III': δH=5.32 (d, 1H, J=3.2 Hz, H-1), 4.41 (dd, 1H, J=5.7, 4.8 Hz, H-3), 4.17 (dd, 1H, J=5.7, 2.3 Hz, H-2), 4.02 (dd, 1H, J=8.6, 3.4 Hz, H-4), 3.84 (dd, 1H, J=10.9, 2.6 Hz, H-5), 3.68 (dd, 1H, J=11.2, 3.4 Hz, H-5'); 'Ring IV': δH=4.90 (d, 1H, J=1.1 Hz, H-1), 3.92-3.86 (m, 2H, H-3, H-5), 3.44 (dd, 1H, J=5.1, 3.6 Hz, H-4), 3.36 (dd, 1H, J=10.9, 8.7 Hz, H-6), 3.01 (dd, 1H, J=3.5, 1.1 Hz, H-2), 2.89 (dd, 1H, J=12.7, 4.1 Hz, H-6'); The additional peaks in the spectrum were identified as follow: 3.62-3.58 (m, 2H, CH$_2$), 2.98-2.95 (m, 2H, CH$_2$), 2.78-2.75 (m, 1H, CH$_2$), 2.71-2.65 (m, 3H, CH$_2$).

$^{13}$C NMR (125 MHz, CDCl$_3$): δC=108.56 (C-1''), 101.68 (C-1'''), 99.86 (C-1'), 86.01 (C-6), 83.89 (C-5), 83.41 (C-2''), 82.12 (C-4''), 79.16 (C-3'), 77.34 (C-4'), 75.65 (C-3''), 75.29, 74.41 (C-5'''), 73.70 (CH2), 72.36 (C-3'''), 72.1 (CH$_2$), 71.08 (C-5'), 70.81 (C-4'''), 61.93 (C-5''), 57.55 (C-2'), 54.73 (C-1), 52.37 (C-3), 51.29 (C-2'''), 50.52 (C-6'''), 43.57 (C-6'), 43.29 (CH$_2$), 42.81 (CH$_2$), 37.31, 35.78 (C-2), 28.59.

TOFMS calcd for $C_{27}H_{56}N_8O_{13}Na$ ([M+Na]+) m/e 723.40; measured m/e 723.63).

Preparation of 4'-O-(2-((benzyloxycarbonyl) (methyl)amino)ethylamino) ethyl-2'',3',3''',4''',5'',6- hexa-O-benzyl-1,2',2''',3,6',6'''-hexaazido-neomycin (27)

The titled compound was prepared as was described for the preparation of compound 18 with the following quantities: compound 25 (1 gram, 0.721 mmol), DCM (50 mL), PhI(OAc)$_2$ (280 mg, 0.870 mmol, 1.2 eq.), N-Cbz-N-Methylethylenediamine (390 mg, 1.88 mmol, 2.6 equiv), sodium triacetoxyborohydride (430 mg, 2.03 mmol, 2.8 equiv). The residue was purified by column chromatography (EtOAc/hexane, 55:45) to afford compound 27 (590 mg, 58%).

$^1$H NMR (500 MHz, CDCl$_3$): 'Ring I': δH=5.48 (d, 1H, J=3.7 Hz, H-1), 3.84 (dd, 1H, J=8.7, 3.6 Hz, H-5), 3.61 (dd, 1H, J=10.8, 6.7 Hz, H-3), 3.24 (dd, 1H, J=6.5, 2.3 Hz, H-4), 2.94 (dd, 1H, J=10.9, 2.7 Hz, H-6), 2.75 (dd, 1H, J=11.5, 2.9 Hz, H-6'), 2.43 (dd, 1H, J=11.2, 3.9 Hz, H-2); 'Ring II': δH=3.94 (dd, 1H, J=6.8, 2.2 Hz, H-5), 3.68 (dd, 1H, J=10.7, 7.2 Hz, H-4), 3.35 (dd, 1H, J=11.2, 6.7 Hz, H-6), 2.98-2.84 (m, 2H, H-1, H-3), 1.91 (dt, 1H, J=10.8, 1.6 Hz, H-2eq), 1.34 (ddd, 1H, J=11.9, 1.9 Hz, H-2ax); 'Ring III': δH=5.69 (d, 1H, J=3.1 Hz, H-1), 4.01 (dd, 1H, J=5.7, 4.9 Hz, H-3), 3.92 (dd, 1H, J=5.2, 2.3 Hz, H-2), 3.78 (dd, 1H, J=8.7, 4.1 Hz, H-4), 3.65 (dd, 1H, J=12.4, 3.7 Hz, H-5), 3.51 (dd, 1H, J=12.2, 3.5 Hz, H-5'); 'Ring IV': δH=5.23 (d, 1H, J=1.3 Hz, H-1), 3.86-3.79 (m, 2H, H-3, H-5), 3.58 (dd, 1H, J=5.2, 3.7 Hz, H-4), 3.49 (dd, 1H, J=12.3, 8.7 Hz, H-6), 3.16 (dd, 1H, J=3.1, 1.5 Hz, H-2), 2.98 (dd, 1H, J=12.4, 8.2 Hz, H-6'); The additional peaks in the spectrum were identified as follow: 7.54-7.28 (m, 35H, Ar), 4.93 (m, 2H, CH$_2$ of Cbz), 4.87 (d, 1H, J=10.8 Hz, PhCH$_2$), 4.81 (d, 1H, J=10.9 Hz, PhCH$_2$), 4.76 (d, 1H, J=10.8 Hz, P PhCH$_2$), 4.69 (d, 1H, J=10.7 Hz, PhCH$_2$), 4.62 (d, 1H, J=11.8 Hz, PhCH$_2$), 4.53 (d, 1H, J=11.9 Hz, PhCH$_2$), 4.47 (d, 1H, J=11.9 Hz, PhCH$_2$), 4.34 (d, 2H, J=11.8 Hz, PhCH$_2$), 4.30 (d, 1H, J=11.7 Hz, PhCH$_2$), 4.27 (d, 1H, J=12.1 Hz, Ph CH$_2$), 4.22 (d, 1H, J=12.0 Hz, PhCH$_2$), 3.36 (m, 2H, CH$_2$), 3.17 (m, 3H, CH$_3$), 3.08 (m, 2H, CH$_2$), 2.82-2.76 (m, 4H, CH$_2$).

$^{13}$C NMR (125 MHz, CDCl$_3$): δC=139.48 (Ar), 138.53 (Ar), 138.14 (Ar), 137.61 (Ar), 137.36 (Ar), 137.08 (Ar), 134.09 (Ar), 129.96 (Ar), 128.83 (Ar), 128.54 (Ar), 128.37 (Ar), 128.24 (Ar), 128.19 (Ar), 128.03 (Ar), 127.33 (Ar), 127.11 (Ar), 125.98 (Ar), 125.74 (Ar), 125.51 (Ar), 124.64 (Ar), 124.58 (Ar), 108.79 (C-1''), 102.45 (C-1'''), 99.76 (C-1'), 85.26 (C-6), 82.94 (C-5), 82.67 (C-2''), 81.97 (C-4''), 79.34 (C-3'), 78.75 (C-4'), 76.18 (CH$_2$), 75.43 (C-3''), 74.84 (C-5'''), 73.58 (CH$_2$), 72.67 (C-3'''), 71.89 (C-5'), 71.26 (C-4'''), 67.85 (C-5''), 66.37 (CH$_2$ of Cbz), 62.74 (C-2'), 57.56 (C-1), 56.84 (C-3), 53.51 (C-2'''), 51.26 (C-6'''), 49.78 (CH$_2$), 48.59 (C-6'), 46.54 (CH$_2$), 37.34 (CH$_3$), 34.68 (C-2), 30.21.

TOFMS calcd for C$_{78}$H$_{88}$N$_{20}$O$_{15}$Na ([M+Na]+) m/e 1567.68; measured m/e 1567.75).

Preparation of 4'-O-(2-(methylamino)ethylamino) ethyl-neomycin (Compound 3; FIGS. 1 and 2B)

The titled compound was prepared as was described for the preparation of Compound 1 with the following quantities: Staudinger reaction: compound 27 (350 mg, 0.226 mmol), THF (10 mL), NaOH (0.1M, 5 mL), PMe$_3$ (1M solution in THF, 6.5 mL, 62.77 mmol) to yield the compound as free amine form. Birch reduction: THF (10 mL), ammonia (about 20 mL), small pieces of Na (120 mg, 5.6 mmol), ammonium formate (1 gram, 15.7 mmol). The analytically pure product was obtained by passing the above product through a short column of Amberlite CG50 (NH$_4^+$ form). The column was first washed with MeOH and H$_2$O, then the product was eluted with a mixture of H$_2$O/NH$_4$OH (93:7) to afford Compound 3 (100 mg, 62% for two steps).

For the storage and biological tests, compound was converted to its sulfate salt form: the free base was dissolved in water, the pH was adjusted around 7.0 with H$_2$SO$_4$ (0.1 N) and lyophilized.

$^1$H NMR (500 MHz, MeOD): 'Ring I': δH=5.40 (d, 1H, J=3.4 Hz, H-1), 3.72 (dd, 1H, J=9.2, 3.8 Hz, H-5), 3.66 (dd, 1H, J=11.2, 7.1 Hz, H-3), 3.05 (dd, 1H, J=7.9, 2.1 Hz, H-4), 3.01 (dd, 1H, J=12.4, 2.7 Hz, H-6), 2.79 (dd, 1H, J=12.5, 6.9 Hz, H-6'), 2.67 (dd, 1H, J=10.4, 3.8 Hz, H-2); 'Ring II': δH=3.52 (dd, 1H, J=7.5, 1.6 Hz, H-5), 3.41 (dd, 1H, J=10.2, 8.1 Hz, H-4), 3.20 (dd, 1H, J=11.3, 7.7 Hz, H-6), 2.78-2.54 (m, 2H, H-1, H-3), 1.99-1.93 (m, 1H, H-2eq), 1.20 (ddd, 1H, J=11.9, 1.9 Hz, H-2ax); 'Ring III': δH=5.29 (d, 1H, J=2.7 Hz, H-1), 4.37 (dd, 1H, J=6.3, 5.1 Hz, H-3), 4.14 (dd, 1H, J=5.2, 2.1 Hz, H-2), 4.05 (dd, 1H, J=9.0, 3.9 Hz, H-4), 3.79 (dd, 1H, J=12.2, 2.2 Hz, H-5), 3.71 (dd, 1H, J=12.2, 3.5 Hz, H-5'); 'Ring IV': δH=4.92 (d, 1H, J=1.0 Hz, H-1), 3.96-3.90 (m, 2H, H-3, H-5), 3.48 (dd, 1H, J=4.8, 3.3 Hz, H-4), 3.32 (dd, 1H, J=11.9, 8.9 Hz, H-6), 2.96 (dd, 1H, J=3.2, 1.3 Hz, H-2), 2.85 (dd, 1H, J=12.4, 8.2 Hz, H—6'); The additional peaks in the spectrum were identified as follow: 4.92 (m, 2H, CH$_2$ of Cbz), 3.61-3.57 (m, 2H, CH$_2$), 3.23 (m, 1H, CH$_2$), 2.95-2.90 (m, 3H, CH$_3$), 2.73-2.71 (m, 1H, CH$_2$), 2.69-2.60 (m, 4H, CH$_2$).

$^{13}$C NMR (125 MHz, MeOD): δC=109.70 (C-1''), 100.67 (C-1'''), 100.28 (C-1'), 85.97 (C-6), 83.76 (C-5), 83.27 (C-2''), 82.23 (C-4''), 78.95 (C-3'), 77.21 (C-4'), 75.95, 75.56 (C-3''), 74.39 (C-5'''), 73.73 (CH$_2$), 72.33 (C-3'''), 72.04 (CH$_2$), 71.05 (C-5'), 70.73 (C-4'''), 65.47 (CH2 of Cbz), 61.89 (C-5''), 57.59 (C-2'), 54.69 (C-1), 52.32 (C-3), 51.33 (C-2'''), 50.48 (C-6'''), 43.61 (C-6'), 43.26 (CH$_2$), 42.76 (CH$_2$), 37.27 (CH$_3$), 35.80 (C-2), 28.64.

TOFMS calcd for C$_{28}$H$_{58}$N$_8$O$_{13}$Na ([M+Na]+) m/e 737.40; measured m/e 737.54).

Preparation of 4-O-(2-(pyrrolidin-1-yl)ethylamino) ethyl-2'',3',3''',4''',5'',6-hexa-O-benzyl-1,2',2''',3,6', 6'''-hexaazidoneomycin (28)

The titled compound was prepared as was described for the preparation of compound 18 with the following quantities: compound 25 (800 mg, 0.580 mmol), DCM (50 mL), PhI(OAc)$_2$ (224 mg, 0.7 mmol, 1.2 eq.), N-(aminoethyl) pyrrolidine (0.2 mL, 1.5 mmol, 2.6 equiv), sodium triacetoxyborohydride (344 mg, 1.62 mmol, 2.8 equiv). The residue was purified by column chromatography (EtOAc/hexane, 60:40) to afford compound 28 (470 mg, 56%).

$^1$H NMR (500 MHz, CDCl$_3$): 'Ring I': δH=6.17 (d, 1H, J=3.9 Hz, H-1), 4.12 (dt, 1H, J=6.8, 4.0 Hz, H-5), 3.96 (dd, 1H, J=10.1, 8.9 Hz, H-3), 3.58 (dd, 1H, J=12.9, 1.7 Hz, H-6), 3.42 (dd, 1H, J=12.2, 5.3 Hz, H-6'), 3.11 (dd, 1H, J=10.0, 8.8 Hz, H-4), 2.99 (dd, 1H, J=10.8, 3.1 Hz, H-2); 'Ring II': δH=3.97 (dd, 1H, J=9.9, 8.1 Hz, H-5), 3.69 (dd, 1H, J=9.7, 8.8 Hz, H-4), 3.52-3.43 (m, 2H, H-1, H-3), 3.34 (dd, 1H, J=10.1, 8.2 Hz, H-6), 2.31-2.25 (m, 1H, H-2eq), 1.46 (dt, 1H, J=12.3, 9.9 Hz, H-2ax); 'Ring III': δH=5.69 (d, 1H, J=5.2 Hz, H-1), 4.35-4.25 (m, 2H, H-3, H-4), 3.99 (dd, 1H, J=5.7, 5.2 Hz, H-2), 3.83 (dd, 1H, J=10.2, 1.8 Hz, H-5), 3.60 (dd, 1H, J=3.19, 10.52 Hz, H-5'); 'Ring IV': δH=4.94 (d, 1H, J=1.7 Hz, H-1), 3.84-3.77 (m, 2H, H-3, H-5), 3.67 (dd, 1H, J=12.8, 9.1 Hz, H-6), 3.39 (dd, 1H, J=4.8, 1.8 Hz, H-2), 3.16 (dd, 1H, J=2.1, 1.6 Hz, H-4), 2.89 (dd, 1H, J=9.2, 4.9 Hz, H-6'). The additional peaks in the spectrum were identified as follow: 3.89-3.86 (m, 1H, CH$_2$), 3.65-3.63 (m, 1H, CH$_2$), 3.30 (m, 2H, CH$_2$), 2.73-2.58 (m, 2H, CH$_2$) 2.54 (m, 4H, CH$_2$, Ring), 1.78 (m, 2H, Ring).

$^{13}$C NMR (125 MHz, CDCl$_3$): δC=138.31 (Ar), 138.08 (Ar), 137.92 (Ar), 137.68 (Ar), 137.04 (Ar), 136.96 (Ar), 128.69 (Ar), 128.51 (Ar), 128.43 (Ar), 128.40 (Ar), 128.35 (Ar), 128.29 (Ar), 128.20 (Ar), 127.96 (Ar), 127.85 (Ar), 127.81 (Ar), 127.81 (Ar), 127.77 (Ar), 127.76 (Ar), 127.50 (Ar), 127.45 (Ar), 106.17 (C-1''), 98.60 (C-1'''), 95.64 (C-1'), 84.22 (C-4''), 82.46 (C-4'), 82.06 (C-4'''), 81.70 (C-2''), 79.62 (C-5), 79.55 (C-6), 75.56 (C-3''), 75.14 (C-3'), 75.12, 75.07 (C-4), 74.38 (C-5'''), 73.29 (C-3'''), 72.88 (C-5'), 72.39 (PhCH$_2$), 71.73 (PhCH$_2$), 71.49 (PhCH$_2$), 71.02 (PhCH$_2$), 70.24 (C-5''), 66.15 (Linker), 63.09 (C-2'), 60.40 (C-1), 59.93 (C-3), 57.29 (C-2'''), 55.88 (Ring), 54.56 (Ring), 54.23 (Linker), 51.39 (C-6'), 51.08 (C-6'''), 49.7 (Linker), 32.49 (C-2), 23.60 (Ring), 23.44 (Ring).

TOFMS calcd for C$_{73}$H$_{86}$N$_{20}$O$_{13}$K ([M+K]+) m/e 1489.63; measured m/e 1489.86).

Preparation of 4-O-(2-(pyrrolidin-1-yl)ethylamino) ethyl-neomycin (Compound 4; FIGS. 1 and 2B)

The titled compound was prepared as described for the preparation of Compound 1 with the following quantities: Staudinger reaction: compound 28 (300 mg, 0.207 mmol), THF (10 mL), NaOH (0.1M, 5 mL), PMe$_3$ (1M solution in THF, 6.1 mL, 58.9 mmol) to yield the compound as free amine form. Birch reduction: THF (10 mL), ammonia (about 20 mL), small pieces of Na (170 mg, 7.9 mmol), ammonium formate (1 gram, 15.7 mmol). The analytically pure product was obtained by passing the above product through a short column of Amberlite CG50 ($NH_4^+$ form). The column was first washed with MeOH and $H_2O$, then the product was eluted with a mixture of $H_2O/NH_4OH$ (96:4) to afford Compound 4 (92 mg, 59% for two steps).

For the storage and biological tests, compound was converted to its sulfate salt form: the free base was dissolved in water, the pH was adjusted around 7.0 with $H_2SO_4$ (0.1 N) and lyophilized.

$^1H$ NMR (500 MHz, MeOD): 'Ring I': δH=5.44 (d, 1H, J=2.6 Hz, H-1), 3.77 (dd, 1H, J=9.8, 3.2 Hz, H-5), 3.69 (dd, 1H, J=10.5, 5.9 Hz, H-3), 3.08 (dd, 1H, J=12.7, 5.8 Hz, H-6), 3.03 (dd, 1H, J=12.1, 2.6 Hz, H-6'), 2.84 (dd, 1H, J=13.5, 6.6 Hz, H-4), 2.72 (dd, 1H, J=10.8, 5.0 Hz, H-2); 'Ring II': δH 3.56 (dd, 1H, J=9.2, 6.6 Hz, H-5), 3.20 (dd, 1H, J=10.5, 7.7 Hz, H-4), 2.86-2.77 (m, 2H, H-1, H-3), 2.66 (dd, 1H, J=9.7, 7.4 Hz, H-6), 2.05-1.91 (m, 1H, H-2eq), 1.22 (ddd, 1H, J=11.3, 5.0 Hz, H-2ax); 'Ring III': δH 5.32 (d, 1H, J=1.7 Hz, H-1), 4.39 (dd, 1H, J=6.1, 5.5 Hz, H-3), 4.16 (dd, 1H, J=5.1, 2.1 Hz, H-2), 4.05 (dd, 1H, J=6.8, 1.2 Hz, H-4), 3.81 (dd, 1H, J=12.3, 1.9 Hz, H-5), 3.73 (dd, 1H, J=11.2, 5.9 Hz, H-5'); 'Ring IV': δH 4.95 (d, 1H, J=1.2 Hz, H-1), 3.95 (dd, 1H, J=3.8, 1.4 Hz, H-3), 3.90 (m, 1H, H-5), 3.54 (dd, 1H, J=12.2, 8.6 Hz, H-6), 3.51 (dd, 1H, J=2.1, 1.1 Hz, H-4), 2.99 (dd, 1H, J=4.0, 2.3 Hz, H-2), 2.72 (dd, 1H, J=9.0, 4.2 Hz, H-6'); the additional peaks in the spectrum were identified as follow: 3.92-3.90 (m, 1H, $CH_2$), 3.51-3.49 (m, 1H, $CH_2$), 3.23-3.19 (m, 2H, $CH_2$), 2.85-2.77 (m, 2H, $CH_2$), 2.69-2.61 (m, 4H, $CH_2$, Ring), 1.87-1.80 (m, 2H, Ring).

$^{13}C$ NMR (125 MHz, MeOD): δC=108.28 (C-1"), 99.17 (C-1'''), 98.69 (C-1'), 84.51 (C-4"), 82.18 (C-4'), 81.77 (C-5), 80.93 (C-6), 77.50 (C-2"), 75.66 (C-3"), 74.26 (C-4'''), 74.12 (C-3'''), 73.53 (C-5'), 72.92 (C-3'), 72.01 (C-4), 70.54 (C-5'''), 69.88 (C-5"), 69.28 ($CH_2$), 60.27 (C-2'), 56.07 (C-2'''), 55.65 (Ring), 53.47 ($CH_2$), 53.21(C-1), 51.11(C-3), 50.87 ($CH_2$), 42.09 (C-6'), 41.76 (C-6'''), 35.78 (C-2), 23.60 (Ring), 22.75 (Ring).

TOFMS calcd for $C_{31}H_{62}N_8O_{13}K$ ([M+K]+) m/e 793.41; measured m/e 793.38).

Preparation of 4-O-(2-guanidinoethylamino)ethyl-2''',3''',3''',4''',5',6-hexa-O-benzyl-1,2',2''',3,6',6'''-hexaazido-neomycin (29)

The titled compound was prepared as was described for the preparation of compound 18 with the following changes and quantities: compound 25 (1 gram, 0.722 mmol), DCM (20 mL), $PhI(OAc)_2$ (1.2 equiv, 279 mg, 0.866 mmol), 2-(2-Aminoethyl)-1,3-di-Boc-guanidine (3 equiv, 655 mg, 2.166 mmol), sodium triacetoxyborohydride (3 equiv, 460 mg, 2.166 mmol). After purification the amine was then dissolved in a solution of TFA in DCM (10 ml, 0.1M) and left to stir in room temperature. Reaction progress was monitored by TLC (EtOAc 90%, MeOH 10%), which indicated completion after 48 hours. After completion the solvent was evaporated to dryness and the crude was purified by column chromatography (EtOAc/MeOH 8:2) to yield 29 (385 mg, 37%).

$^1H$ NMR (500 MHz, MeOD): 'ring I': δH=6.14 (d, 1H, J=4.07 Hz, H-1), 4.09-4.04 (m, 1H, H-5), 3.87 (dd, 1H, J=10.01, 8.98 Hz, H-3), 3.53 (dd, 1H, J=14.13, 1.68 Hz, H-6), 3.39 (dd, 1H, J=13.43, 4.43 Hz, H-6'), 3.09 (dd, 1H, J=9.91, 8.67 Hz, H-4), 2.92 (dd, 1H, J 10.84, 3.53 Hz, H-2); 'ring II': δH=3.75 (dd, 1H, J=8.85, 8.85 Hz, H-5), 3.61 (dd, 1H, J=9.39, 9.39 Hz, H-4), 3.52-3.42 (m, 2H, H-1, H-3), 3.25 (dd, 1H, J=9.59, 9.59 Hz, H-6), 2.12 (dt, 1H, J=13.97, 5.07, 5.07 Hz, H-2eq), 1.32 (ddd, 1H, J=12.93, 12.26, 12.26 Hz, H-2ax); 'ring III': δH=5.54 (d, 1H, J=4.39 Hz, H-1), 4.18 (dd, 1H, J=8.46, 4.23 Hz, H-3), 4.17-4.11 (m, 1H, H-4), 3.94 (dd, 1H, J=4.88, 4.88 Hz, H-2), 3.74 (dd, 1H, J=10.63, 2.27 Hz, H-5), 3.50 (dd, 1H, J=10.86, 4.50 Hz, H-5'); 'ring IV': δH=4.81 (d, 1H, J=1.83 Hz, H-1), 3.81-3.74 (m, 1H, H-3), 3.80-3.78 (m, 1H, H-5), 3.53-3.46 (m, 1H, H-6), 3.28-3.26 (m, 1H, H-4), 3.25-3.23 (m, 1H, H-2), 3.02-2.96 (m, 1H, H-6'); the additional peaks in the spectrum were identified as follow: δH 7.39-7.09 (m, 30H, Ar), 4.84-4.80 (m, 1H, $BnCH_2$), 4.75 (d, 1H, J=11.36 Hz, $BnCH_2$), 4.73-4.64 (m, 2H, $BnCH_2$), 4.54 (d, J=11.67 Hz, 1H), 4.49-4.38 (m, 5H, $BnCH_2$), 4.31 (d, 2H, J=11.76 Hz, $BnCH_2$), 4.03-3.99 (m, 1H, $CH_2$), 3.94 (dd, 1H, J=4.68, 4.68 Hz, $CH_2$), 3.77-3.72 (m, 1H, $CH_2$), 3.52-3.46 (m, 1H, $CH_2$), 3.43-3.35 (m, 2H, $CH_2$), 3.06-2.96 (m, 2H, $CH_2$).

$^{13}C$ NMR (126 MHz, $CDCl_3$): δC 157.50 (Guanidine), 138.21 (Ar), 138.04 (Ar), 137.97 (Ar), 137.65 (Ar), 137.46 (Ar), 137.38 (Ar), 128.20 (Ar), 128.09 (Ar), 128.04 (Ar), 128.00 (Ar), 127.92 (Ar), 127.78 (Ar), 127.56 (Ar), 127.47 (Ar), 127.26 (Ar), 106.95 (C-1"), 98.45 (C-1'''), 95.53 (C-1'), 83.95 (C-6), 82.06 (C-4), 82.02 (C-5"), 81.47 (C-2"), 79.36 (C-3'), 79.14 (C-4'), 75.80 (C-3"), 75.37 (C-4), 74.67 ($PhCH_2$), 74.30 (C-5'''), 74.18 ($PhCH_2$), 73.15, 72.91 ($PhCH_2$), 72.78 ($PhCH_2$), 72.15 ($PhCH_2$), 71.97 (C-2'''), 71.57 ($PhCH_2$), 70.43 (C-5'), 70.27 (C-3'''), 63.01 (C-2'), 60.33 (C-1, C-3), 60.09 ($CH_2$), 59.92, 57.08 (C-4'''), 50.90 (C-6', C-6'''), 46.37 ($CH_2$), 37.88 ($CH_2$), 31.77 (C-2).

MALDI TOFMS calcd for $C_{70}H_{81}N_{22}O_{22}$ ([M+H]+) m/e 1438.64; measured m/e 1439.00).

Preparation of 4'-O-(2-guanidinoethylamino)ethyl-neomycin (Compound 5; FIGS. 1 and 2B)

Compound 29 (385 mg, 0.267 mmol) was dissolved in a mixture of THF (10 mL) and aqueous NaOH (0.1M, 10 mL). This mixture was stirred at room temperature for 10 minutes, after which $PMe_3$ (1M solution in THF, 9.63 mL, 38.91 mmol) was added. Propagation of the reaction was monitored by TLC [$CH_2Cl_2$/MeOH/$H_2O$/$MeNH_2$ (33% solution in EtOH), 10:15:6:15], which indicated completion after 3 hours. The reaction mixture was purified by flash chromatography on a short column of silica gel. The column was washed with the following solvents: hexane (200 mL), THF (200 mL), $CH_2Cl_2$ (200 mL), EtOAc (200 mL), MeOH (400 mL). The product was eluted with the mixture of 20% AcOH in 80% MeOH. Fractions containing the product were combined and evaporated under vacuum. THF (10 mL) was added via syringe to a dry three neck flask equipped with a Dewar condenser. Then ammonia (about 20 mL) was condensed into the reaction vessel. Small pieces of Na (300 mg, 13 mmol) were then allowed to dissolve in the ammonia for 15 min. Then a solution of the aminoglycoside in a mixture of EtOH and THF (500 L each) was added in one portion and washed down with THF. The reaction was stirred until the blue color was discharged. Then an aqueous solution of ammonium formate (1 gram, 15.7 mmol) was added, and the ammonia was allowed to evaporate. The remaining solvent was removed in Vacuum, and the residue was loaded onto a short column of silica gel. The column was washed with the following solvents: hexane (200 mL), THF (200 mL), $CH_2Cl_2$ (200 mL), EtOAc (200 mL), MeOH (400 mL). The product was eluted with the mixture of 2% TFA in 98% MeOH. The containing fractions were evaporated under vacuum to afford Compound 5 as a TFA salt (56 mg, 27%).

$^1H$ NMR (500 MHz, MeOD): 'ring I': δH=5.98 (d, 1H, J=4.13 Hz, H-1), 4.18 (dd, 1H, J=11.87, 2.09 Hz, H-3), 4.05 (ddd, 1H, J=9.17, 6.96, 4.13 Hz, H-5), 3.43-3.37 (m, 2H, H-2, H-4), 3.27-3.23 (m, 1H, H-6), 3.14 (dd, 1H, J=13.20, 8.06 Hz, H-6'); 'ring II': δH=4.10-4.05 (m, 1H, H-4), 3.83 (dd, 1H, J=9.10, 9.10 Hz, H-5), 3.53 (dd, 1H, J=9.79, 9.70 Hz, H-6), 3.44-3.30 (m, 1H, H-3), 3.21-3.07 (m, 1H, H-1), 2.47-2.41 (m, 1H, H-2eq), 2.04 (ddd, 1H, J=12.37, 12.37, 12.37 Hz, H-2ax); 'ring III': δH=5.40 (d, 1H, J=2.39 Hz, H-1), 4.48 (dd, 1H, J=6.63, 4.35 Hz, H-3), 4.34 (dd, 1H, J=5.20, 1.50 Hz, H-2), 4.18 (ddd, 1H, J 10.00, 3.97, 1.82 Hz, H-4), 3.87 (dd, 1H, J=5.54, 1.50 Hz, H-5), 3.70 (dd, 1H, J=12.28, 4.17 Hz, H-5'); 'ring IV': δH=5.26 (d, 1H, J=1.73 Hz, H-1), 4.26 (ddd, 1H, J=7.85, 3.83, 1.45 Hz, H-5), 4.11 (dd, 1H, J=3.17, 3.17 Hz, H-3), 3.66-3.65 (m, 1H, H-4), 3.41-3.39 (m, 1H, H-2), 3.35 (dd, 1H, J=13.39, 7.41 Hz, H-6), 3.23 (dd, 1H, J=13.38, 3.73 Hz, H-6'); the additional peaks in the spectrum were identified as follow: 4.19-4.17 (m, 1H, $CH_2$), 3.97-3.91 (m, 1H, $CH_2$), 3.64-3.62 (m, 4H, $CH_2$), 3.28-3.25 (m, 2H, $CH_2$).

$^{13}$C NMR (126 MHz, CDCl$_3$): δC=161.28 (q, TFA-CO), 157.45 (GUA), 116.42 (q, TFA-CH3), 110.37 (C-1''), 95.37 (C-1', C1'''), 85.06 (C-5), 81.90 (C-4'', C-3'), 79.69 (C-1), 75.30 (C-3''), 75.17 (C-5'), 74.01 (C-2''), 72.71 (C-6), 70.52 (C-5'''), 67.70 (C-3''', C-4'''), 67.66 (C-4), 67.13 ($CH_2$), 59.61 (C-5''), 53.87 (C-4'), 51.42 (C-2', C-2''), 49.91 (C-3), 48.67, 47.73 ($CH_2$), 46.04 ($CH_2$), 40.06 (C-6', C-6'''), 37.25 ($CH_2$), 28.10 (C-2).

MALDI TOFMS calcd for $C_{28}H_{59}N_{10}O_{13}$ ([M+H]+) m/e 743.43; measured m/e 743.40).

Synthesis of 4'- and 6'-amide-linked compounds (Compounds 6-10)

For the synthesis of the 4'-amide derivatives, alcohol 23 (FIG. 2B) was first oxidized with Dess-Martin periodinane (DMP) to form corresponding 4'-ketone 30, which was then reduced with sodium borohydride to afford compound 31 with an axial hydroxy group at the 4'-position. Compound 31 was treated with triflic anhydride (Tf$_2$O, pyridine, CH$_2$Cl$_2$) to form the corresponding 4'-triflate, which was then treated with ammonia in acetone to yield 32 with an equatorial amine group at the 4'-position.

Next, 32 was treated with chloroacetyl chloride to give 4'-chloride 33, which was then separately treated with three different amines, compounds A and B (shown above) and diethylenetriamine, to afford the corresponding 4'-amide derivatives of NeoB in their protected forms (compounds 34, 35, and 36, respectively).

These products were then deprotected by using the two-step procedure described above (Staudinger and Birch) to afford the corresponding 4'-amide derivatives of NeoB, Compounds 6, 7, and 8, in yields of 64, 68, and 20%, respectively (See, FIG. 5). During the last deprotection step (the Birch reduction), it was uncovered that if this step was performed in the presence of an excess amount of sodium, transamidation rearrangement of the warhead, from the 4'-position to the 6'-position, took place. The structure of the rearrangement product (6'-amide) was confirmed by its isolation and subsequent spectral assignment by using a combination of various 1D and 2D NMR spectroscopy techniques. This rearrangement probably occurred as a result of the strong basic conditions generated after quenching of the reaction, which resulted in the formation of sodium hydroxide. This transformation was exploited by performing the Birch reaction step with an excess amount of sodium and corresponding 6'-amide-linked Compounds 9 and 10 were prepared in yields of 74 and 36%, respectively.

The following describes the detailed syntheses of Compounds 6-10 and the intermediates thereof.

Preparation of 4'-oxo-2'',3',3''',4''',5'',6-hexa-O-benzyl-1,2',2''',3,6',6'''-hexaazido-neomycin (30)

Under argon, a solution of compound 23 (5 grams, 3.81 mmol) in CH$_2$Cl$_2$ (50 mL) was treated with Dess-Martin periodinane (3.2 grams, 7.6 mmol, 2 eq.) and stirred for 4 hours at room temperature. The reaction progress was monitored by TLC (Hexane/EtOAc, 7:3). After completion of the reaction, the mixture was diluted with EtOAc and quenched with saturated aqueous sodium thiosulfate, sodium bicarbonate and brine. The combined organic phases were dried over anhydrous MgSO$_4$, filtered and evaporated to dryness. The residue was purified by column chromatography (Hexane/EtOAc 75:25) to yield compound 30 (4.3 grams, 86%).

$^1$H NMR (500 MHz, CDCl$_3$): 'Ring I': δH=6.34 (d, 1H, J=2.1 Hz, H-1), 4.72 (dd, 1H, J=4.2, 1.0 Hz, H-5), 4.39 (d, 1H, J=10.3 Hz, H-3), 3.46-3.36 (m, 3H, H-2, H-6, H-6'); 'Ring II': δH=3.97 (dd, 1H, J=9.2, 8.7 Hz, H-5), 3.69 (dd, 1H, J=9.3, 8.8 Hz, H-4), 3.55-3.39 (m, 2H, H-1, H-3), 3.32 (dd, 1H, J=8.9 Hz, H-6), 2.26 (dt, 1H, J=8.4, 4.0 Hz, H-2eq), 1.45 (ddd, 1H, J=12.9 Hz, H-2ax); 'Ring III': δH=5.68 (d, 1H, J=5.7 Hz, H-1), 4.32-4.22 (m, 2H, H-3, H-4), 3.95 (t, 1H, J=5.9 Hz, H-2), 3.78 (dd, 1H, J=9.7, 1.3 Hz, H-5), 3.55 (dd, 1H, J=10.4, 2.7 Hz, H-5'); 'Ring IV': δH 4.91 (d, 1H, J=2.5 Hz, H-1), 3.80-3.73 (m, 2H, H-3, H-5), 3.64 (dd, 1H, J=13.1, 9.2 Hz, H-6), 3.35 (dd, 1H, J=1.7, 1.1 Hz, H-2), 3.11 (dd, 1H, J=3.2, 1.2 Hz, H-4), 2.86 (dd, 1H, J=6.6, 4.5 Hz, H-6'); The additional peaks in the spectrum were identified as follow: 7.41-7.14 (m, 30H, Ar), 4.97 (d, 1H, J=10.5 Hz, PhCH$_2$), 4.89 (d, 1H, J=13.2 Hz, PhCH$_2$), 4.71 (d, 1H, J=10.4 Hz, PhCH$_2$), 4.63 (d, 1H, J=12.1 Hz, PhCH$_2$), 4.57 (d, 2H, J=11.3 Hz, PhCH$_2$), 4.47 (d, 1H, J=13.0 Hz, PhCH$_2$), 4.39 (d, 1H, J=10.7 Hz, PhCH$_2$), 4.32 (d, 1H, J=12.0 Hz, PhCH$_2$), 4.26 (d, 2H, J=7.5 Hz, PhCH$_2$), 4.24 (d, 1H, J=7.8 Hz, PhCH$_2$).

$^{13}$C NMR (125 MHz, CDCl$_3$): δC=201.60 (C-4'), 137.96 (Ar), 137.78 (Ar), 137.52 (Ar), 136.95 (Ar), 136.89 (Ar), 136.75 (Ar), 128.65 (Ar), 128.47 (Ar), 128.45 (Ar), 128.39 (Ar), 128.34 (Ar), 128.33 (Ar), 128.24 (Ar), 128.17 (Ar), 128.11 (Ar), 127.79 (Ar), 127.77 (Ar), 127.75 (Ar), 127.60 (Ar), 127.49 (Ar), 127.38 (Ar), 106.04 (C-1''), 98.66 (C-1'''), 95.40 (C-1'), 84.23 (C-6), 82.55 (C-2''), 82.16 (C-4''), 81.70 (C-5), 78.90 (C-3'), 75.82 (C-3''), 75.49 (PhCH$_2$), 75.12 (PhCH$_2$), 74.36 (C-4), 73.90 (C-5'''), 73.48 (PhCH$_2$), 73.38 (PhCH$_2$), 73.29 (C-3'''), 72.81 (PhCH$_2$), 72.34 (C-5'), 71.67 (C-4'''), 69.95 (C-5''), 63.62 (C-2'''), 60.22 (C-2'), 59.80 (C-1), 57.20 (C-3), 51.05 (C-6'), 49.54 (C-6'''), 32.26 (C-2).

TOFMS calcd for $C_{65}H_{68}N_{18}O_{13}$Na ([M+Na]+) m/e 1331.51; measured m/e 1331.59).

Preparation of 4'-hydroxy-2'',3',3''',4''',5'',6-hexa-O-benzyl-1,2',2''',3,6',6'''-hexaazido-neomycin (31)

Under argon, a solution of compound 30 (4.3 grams, 3.3 mmol) in MeOH (50 mL) was cooled to –10° C. Then, the mixture was treated with NaBH$_4$ (0.25 gram, 6.6 mmol, 2 eq.) and left to stir for 30 minutes then the mixture was allowed to warm to room temperature and was stirred for another 2 hours. The reaction propagation was monitored by TLC (Hexane/EtOAc, 7:3). After completion, the mixture was diluted with EtOAc and washed with 1M HCl, saturated aqueous NaHCO$_3$ and brine. The combined organic phases were dried over anhydrous MgSO$_4$, filtered and evaporated to dryness. The residue was purified by column chromatography (Hexane/EtOAc, 75:25) to obtain compound 31 (3.56 grams, 82%).

$^1$H NMR (500 MHz, CDCl$_3$): 'Ring I': δH=6.23 (d, 1H, J=3.1 Hz, H-1), 4.18 (dd, 1H, J=8.9, 5.9 Hz, H-5), 4.01 (dd, 1H, J=10.9, 1.8 Hz, H-3), 3.96 (t, 1H, J=3.7 Hz, H-4), 3.62 (dd, 1H, J=13.0, 3.5 Hz, H-6), 3.42 (dd, 1H, J=9.9, 4.5 Hz, H-2), 3.30 (dd, 1H, J=12.2, 3.8 Hz, H-6'); 'Ring II': δH=3.94 (dd, 1H, J=9.2 Hz, H-5), 3.69 (dd, 1H, J=9.0, 1.1 Hz, H-4), 3.54-3.38 (m, 2H, H-1, H-3), 3.30 (dd, 1H, J=9.0 Hz, H-6), 2.23 (dt, 1H, J=8.1, 4.8 Hz, H—2eq), 1.43 (ddd, 1H, J=12.4, 1.1 Hz, H-2ax); 'Ring III': δH=5.66 (d, 1H, J=5.1 Hz, H-1), 4.28 (dd, 1H, J=3.9, 1.8 Hz, H-4), 4.24 (dd, 1H, J=4.4, 3.0 Hz, H-3), 3.95 (dd, 1H, J=9.8, 3.7 Hz, H-2), 3.77 (dd, 1H, J=9.9, 1.3 Hz, H-5), 3.56 (dd, 1H, J=10.3, 2.8 Hz, H-5'); 'Ring IV': δH=4.88 (d, 1H, J=1.4 Hz, H-1), 3.80-3.71 (m, 2H, H-3, H-5), 3.62 (dd, 1H, J=12.9, 8.3 Hz, H-6), 3.34 (dd, 1H, J=4.3, 1.5 Hz, H-2), 3.12 (dd, 1H, J=1.9, 1.3 Hz, H-4), 2.89 (dd, 1H, J=11.9, 4.4 Hz, H-6'); the additional peaks in the spectrum were identified as follow: δ 7.38-7.14 (m, 30H, Ar), 4.95 (d, 1H, J=10.6 Hz, PhCH$_2$), 4.72 (d, 1H, J=11.5 Hz, PhCH$_2$), 4.68 (d, 1H, J=5.8 Hz, PhCH$_2$), 4.64 (d, 1H, J=8.3 Hz, PhCH$_2$), 4.62 (d, 1H, J=5.3 Hz, PhCH$_2$), 4.60 (d, 1H, J=8.2 Hz, PhCH$_2$), 4.55 (d, 1H, J=11.8 Hz, PhCH$_2$), 4.48 (d, 1H, J=4.9 Hz, PhCH$_2$), 4.45 (d, 1H, J=12.0 Hz, PhCH$_2$), 4.42 (d, 1H, J=12.1 Hz, PhCH$_2$), 4.32 (d, 1H, J=12.0 Hz, PhCH$_2$), 4.26 (d, 1H, J=12.1 Hz, PhCH$_2$).

$^{13}$C NMR (125 MHz, CDCl$_3$): δC=138.27 (Ar), 137.95 (Ar), 137.68 (Ar), 137.16 (Ar), 137.08 (Ar), 137.00 (Ar), 128.79 (Ar), 128.70 (Ar), 128.52 (Ar), 128.44 (Ar), 128.36 (Ar), 128.35 (Ar), 128.31 (Ar), 128.28 (Ar), 128.17 (Ar), 127.86 (Ar), 127.80 (Ar), 127.77 (Ar), 127.57 (Ar), 127.49 (Ar), 127.35 (Ar), 106.12 (C-1"), 98.66 (C-1'''), 95.82 (C-1'), 84.28 (C-6), 82.51 (C-2"), 82.14 (C-5), 81.65 (C-3'), 75.66, 75.55 (C-3"), 75.07 (PhCH$_2$), 75.00 (C-4), 74.31 (C-5'''), 73.35 (PhCH$_2$), 72.97 (C-3'''), 72.41 (PhCH$_2$), 72.25 (PhCH$_2$), 71.77 (PhCH$_2$), 71.54 (C-5'), 70.25 (C-5"), 69.34 (C-4'''), 66.85 (C-2'''), 60.40 (C-2'), 60.14 (C-1), 58.54 (C-3), 57.32 (C-4'), 51.40 (C-6'), 51.05 (C-6'''), 32.49 (C-2).

TOFMS calcd for C$_{65}$H$_{70}$N$_{18}$O$_{13}$K ([M+K]+) m/e 1350.46; measured m/e 1350.78).

Preparation of 4'-amino-4'-deoxy-2",3',3''',4''',5",6-hexa-O-benzyl-1,2',2''',3,6',6'''-hexaazido-neomycin (32)

Compound 31 (3.56 grams, 2.71 mmol) was dissolved in a mixture of pyridine (50 mL) and CH2Cl2 (20 mL). The solution was cooled to −10° C., treated dropwise with Tf$_2$O (1.37 mL, 8.15 mmol, 3 eq.) and stirred for 3 hours. The reaction propagation was monitored by TLC (Hexane/EtOAc, 7:3). After completion, the mixture was diluted with EtOAc and washed with 1M HCl, saturated aqueous NaHCO$_3$ and brine. The combined organic phases were dried over anhydrous MgSO$_4$, filtered and evaporated to dryness. In the hydrogenation reactor, the crude compound was dissolved in fresh distilled acetone (20 mL) and cooled to −78° C. Then Ammonia (30 mL) was condensed in to the reaction vessel, the mixture was allowed to warm to room temperature and was stirred for 48 hours. The solvents were evaporated to dryness and the residue was purified by column chromatography (Hexane/EtOAc, 6:4) to obtain compound 32 (1.46 gram, 41%).

$^1$H NMR (500 MHz, CDCl$_3$): 'Ring I': δH=6.22 (d, 1H, J=2.2 Hz, H-1), 3.82 (dd, 1H, J=7.6, 5.3 Hz, H-5), 3.62 (dd, 1H, J=9.6 Hz, H-3), 3.50 (dd, 1H, J=12.2, 1.1 Hz, H-6), 3.31 (dd, 1H, J=13.2, 5.8 Hz, H-6'), 2.89 (dd, 1H, J=10.5, 5.7 Hz, H-2), 2.41 (dd, 1H, J=11.0, 5.4 Hz, H-4); 'Ring II': δH=3.89 (dd, 1H, J=9.0 Hz, H-5), 3.61 (dd, J=9.8, 8.1 Hz, H-4), 3.47-3.29 (m, 2H, H-1, H-3), 3.21 (dd, J=9.7, 8.7 Hz, H-6), 2.13 (dt, 1H, J=7.8, 4.8 Hz, H-2eq), 1.32 (ddd, 1H, J=12.2, 1.8 Hz, H-2ax); 'Ring III': δH=5.66 (d, 1H, J=4.7 Hz, H-1), 4.39-4.15 (m, 2H, H-3, H-4), 3.93 (dd, 1H, J=6.0 Hz, H-2), 3.78 (dd, 1H, J=10.4, 1.5 Hz, H-5), 3.54 (dd, 1H, J=9.8, 1.8 Hz, H-5'); 'Ring IV': δH=4.89 (d, 1H, J=2.3 Hz, H-1), 3.77-3.69 (m, 2H, H-3, H-5), 3.61 (dd, 1H, J=12.7, 8.4 Hz, H-6), 3.31 (dd, 1H, J=3.0, 2.3 Hz, H-2), 3.08 (dd, 1H, J=1.9, 1.1 Hz, H-4), 2.84 (dd, 1H, J=13.0, 3.3 Hz, H-6'). The additional peaks in the spectrum were identified as follow: 7.32-7.12 (m, 30H, Ar), 4.93 (d, 1H, J=10.5 Hz, PhCH$_2$), 4.90 (d, 1H, J=8.7 Hz, PhCH$_2$), 4.68 (d, 1H, J=10.4 Hz, PhCH$_2$), 4.59 (d, 1H, J=12.3 Hz, PhCH$_2$), 4.55 (d, 1H, J=11.4 Hz, PhCH$_2$), 4.49 (d, 1H, J=12.0 Hz, PhCH$_2$), 4.44 (d, 1H, J=9.2 Hz, PhCH$_2$), 4.42 (d, 1H, J=11.7 Hz, PhCH$_2$), 4.38 (d, 1H, J=12.0 Hz, PhCH$_2$), 4.28 (d, 1H, J=12.2 Hz, PhCH$_2$), 4.24 (d, 1H, J=12.0 Hz, PhCH$_2$), 4.22 (d, 1H, J=12.4 Hz, PhCH$_2$).

$^{13}$C NMR (125 MHz, CDCl$_3$): δC=138.24 (Ar), 137.89 (Ar), 137.85 (Ar), 137.63 (Ar), 136.99 (Ar), 136.93 (Ar), 128.65 (Ar), 128.58 (Ar), 128.48 (Ar), 128.40 (Ar), 128.35 (Ar), 128.31 (Ar), 128.24 (Ar), 128.22 (Ar), 128.16 (Ar), 128.06 (Ar), 127.80 (Ar), 127.78 (Ar), 127.74 (Ar), 127.44 (Ar), 127.29 (Ar), 106.02 (C-1"), 98.60 (C-1'''), 95.98 (C-1'), 84.33 (C-6), 82.55 (C-2"), 82.09 (C-4"), 81.67 (C-5), 80.51 (C-3'), 75.54 (C-3"), 75.06 (PhCH$_2$), 75.00 (PhCH$_2$), 74.88 (PhCH$_2$), 74.36 (C-4), 73.33 (C-5'''), 73.22 (C-3'''), 72.86 (PhCH$_2$), 72.33 (C-5'), 71.68 (PhCH$_2$), 71.43 (C-4'''), 70.19 (C-5"), 63.32 (C-2'''), 60.36 (C-2'), 60.24 (C-1), 57.21 (C-3), 54.36 (C-4'), 52.14 (C-6'), 51.18 (C-6'''), 32.55 (C-2).

TOFMS calcd for C$_{65}$H$_{71}$N$_{19}$O$_{12}$ ([M]+) m/e 1309.55; measured m/e 1309.80).

Preparation of 4'-(2-chloroacetamido)-4'-deoxy-2",3',3''',4''',5",6-hexa-O-benzyl-1,2',2''',3,6',6'''-hexaazido-neomycin (33)

To a solution of amine 32 (1 gram, 0.76 mmol) in anhydrous THF (10 mL), NaHCO$_3$ (0.25 gram, 3 mmol) was added and the mixture was stirred at room temperature. Then, the solution was treated with chloroacetyl chloride (0.25 mL, 3.14 mmol, 4 eq.) and the reaction was stirred for 1 hour. The reaction propagation was monitored by TLC (Hexane/EtOAc, 6:4). After completion, the mixture was diluted with EtOAc and washed with 1M HCl and brine. The combined organic phases were dried over anhydrous MgSO$_4$, filtered and evaporated to dryness. The crude product was purified by flash chromatography (Hexane/EtOAc, 75:25) to afford compound 33 (1.1 gram, 98%).

$^1$H NMR (500 MHz, CDCl$_3$): 'Ring I': δH=6.24 (d, 1H, J=3.8 Hz, H-1), 3.99 (dd, 1H, J=8.7, 6.5 Hz, H-5), 3.84 (dd, 1H, J=9.2 Hz, H-3), 3.74 (dd, 1H, J=12.3, 1.6 Hz, H-4), 3.25 (dd, 1H, J=13.5, 6.9 Hz, H-6), 3.16 (dd, 1H, J=13.1, 2.5 Hz, H-6'), 3.03 (dd, 1H, J=10.0, 2.9 Hz, H-2); 'Ring II': δH=3.94 (dd, 1H, J=8.8 Hz, H-5), 3.67 (dd, 1H, J=9.2 Hz, H-4), 3.57-3.35 (m, 2H, H-1, H-3), 3.27 (dd, 1H, J=9.5 Hz, H-6), 2.19 (dt, 1H, J=13.2, 4.5 Hz, H-2eq), 1.37 (ddd, 1H, J=12.8, 4.0 Hz, H-2ax); 'Ring III': δH=5.65 (d, 1H, J=5.4 Hz, H-1), 4.25-4.22 (m, 2H, H-3, H-4), 3.91 (dd, 1H, J=6.4, 5.3 Hz, H-2), 3.78 (dd, 1H, J=10.1, 1.4 Hz, H-5), 3.54 (dd, 1H, J=9.8, 1.4 Hz, H-5'); 'Ring IV': δH=4.91 (d, 1H, J=1.5 Hz, H-1), 3.81-3.74 (m, 2H, H-3, H-5), 3.63 (dd, 1H, J=12.8, 9.1 Hz, H-6), 3.32 (dd, 1H, J=4.7, 1.9 Hz, H-2), 3.09 (dd, 1H, J=3.0, 1.5 Hz, H-4), 2.85 (dd, 1H, J=14.1, 2.8 Hz, H-6'); the additional peaks in the spectrum were identified as follow:

7.33-7.13 (m, 30H, Ar), 6.35 (d, 1H, J=9.2 Hz, Amide), 4.92 (d, 1H, J=10.4 Hz, PhCH$_2$), 4.73 (d, 1H, J=11.4 Hz, PhCH$_2$), 4.67 (d, 1H, J=10.6 Hz, PhCH$_2$), 4.59 (d, 1H, J=9.0 Hz, PhCH$_2$), 4.57 (d, 1H, J=8.7 Hz, PhCH$_2$), 4.47 (d, 1H, J=11.8 Hz, PhCH$_2$), 4.43 (d, 1H, J=11.7 Hz, PhCH$_2$), 4.43 (d, 1H, J=11.8 Hz, PhCH$_2$), 4.38 (d, 1H, J=12.0 Hz, PhCH$_2$), 4.28 (d, 1H, J=12.1 Hz, PhCH$_2$), 4.24 (d, 1H, J=8.9 Hz, PhCH$_2$), 4.22 (d, 1H, J=12.0 Hz, PhCH$_2$).

$^{13}$C NMR (125 MHz, CDCl$_3$): δC=166.36 (Amide), 138.39 (Ar), 138.15 (Ar), 137.92 (Ar), 137.83 (Ar), 137.30 (Ar), 137.24 (Ar), 128.98 (Ar), 128.82 (Ar), 128.81 (Ar), 128.72 (Ar), 128.65 (Ar), 128.63 (Ar), 128.58 (Ar), 128.49 (Ar), 128.31 (Ar), 128.30 (Ar), 128.12 (Ar), 128.08 (Ar), 128.07 (Ar), 128.00 (Ar), 127.78 (Ar), 106.32 (C-1''), 98.96 (C-1'''), 95.81 (C-1'), 84.65 (C-6), 82.92 (C-2''), 82.43 (C-4''), 81.88 (C-5), 76.80 (C-3'), 76.06 (C-3'''), 75.80 (C-3''), 75.44 (PhCH$_2$), 74.73 (C-4), 74.52 (PhCH$_2$), 73.69 (PhCH$_2$), 73.14 (C-5'''), 72.66 (PhCH$_2$), 72.00 (PhCH$_2$), 71.74 (C-5'), 71.47 (C-4'''), 70.90 (PhCH$_2$), 70.41 (C-5''), 70.39 (C-4'), 62.75 (C-2'), 60.62 (C-2'''), 60.52 (C-1), 57.52 (C-3), 52.33 (C-6'), 51.41 (C-6'''), 32.83 (C-2).

TOFMS calcd for C$_{66}$H$_{70}$N$_{19}$ClO$_{13}$K ([M+K]+) m/e 1410.47; measured m/e 1410.67.

Preparation of 4'-(2-(aminoethylazido)acetamido)-4'-deoxy-2'',3',3''',4''',5'',6-hexa-O-benzyl-1,2',2''',3,6',6'''-hexaazidoneomycin (34)

To a solution of compound 33 (0.5 gram, 0.36 mmol) in anhydrous DMF (10 mL), N,N-diisopropylethylamine (0.25 mL, 1.43 mmol, 4 eq.) was added and the reaction was stirred at room temperature. Then, the solution was treated with azidoethyleneamine (0.124 gram, 1.44 mmol, 4 eq.), heated to 60° C. and left overnight. The reaction propagation was monitored by TLC (Hexane/EtOAc, 1:1). After completion, the mixture was diluted with EtOAc and washed with 1M HCl, saturated aqueous NaHCO$_3$ and brine. The combined organic phases were dried over anhydrous MgSO$_4$, filtered and evaporated to dryness. The crude product was purified by flash chromatography (Hexane/EtOAc, 6:4) to afford compound 34 (0.375 gram, 72%).

$^1$H NMR (500 MHz, CDCl$_3$): 'ring I': δH=6.22 (d, 1H, J=3.83 Hz, H-1), 3.95 (dd, 1H, J=8.68, 8.68 Hz, H-5), 3.83 (dd, 1H, J=9.95, 9.56 Hz, H-3), 3.72 (ddd, 1H, J=9.93, 9.93, 9.84 Hz, H-4), 3.23 (dd, 1H, J=13.52, 7.02 Hz, H-6), 3.11 (d, 1H, J=12.53 Hz, H-6'), 2.97 (dd, 1H, J=9.53, 3.17 Hz, H-2); 'ring II': δH=3.91 (dd, 1H, J=9.07, 9.07 Hz, H-5), 3.64 (dd, 1H, J=9.47, 9.47 Hz, H-4), 3.43 (td, 1H, J=9.70, 9.67, 5.17 Hz, H-3), 3.36 (td, 1H, J=9.77, 9.71, 5.13 Hz, H-1), 3.23 (dd, 1H, J=9.46, 9.46 Hz, H-6), 2.15 (dt, 1H, J=12.89, 4.52, 4.52 Hz, H-2eq), 1.34 (ddd, 1H, J=12.75, 12.75, 12.75 Hz, H-2ax); 'ring III': δH=5.62 (d, 1H, J=6.03 Hz, H-1), 4.21-4.18 (m, 2H, H-3, H-4), 3.90-3.87 (m, 1H, H-2), 3.74 (dd, 1H, J=8.08, 2.95 Hz, H-5), 3.49 (dd, 1H, J=10.48, 2.93 Hz, H-5'); 'ring IV': δH=4.87 (d, 1H, J=2.26 Hz, H-1), 3.72 (ddd, 1H, J=4.06, 4.06, 4.06 Hz, H-5), 3.68 (dd, 1H, J=2.82, 2.82 Hz, H-3), 3.58 (dd, 1H, J=13.04, 8.51 Hz, H-6), 3.28 (dd, 1H, J=2.22, 2.22 Hz, H-2), 3.05 (d, 1H, J=2.66 Hz, H-4), 2.79 (dd, 1H, J=13.04, 3.83 Hz, H-6'); the additional peaks in the spectrum were identified as follow: 7.31-7.06 (m, 30H, Ar), 7.08 (d, 1H, J=9.22 Hz, Amide) 4.89 (d, 1H, J=10.50 Hz, PhCH$_2$), 4.72 (d, 1H, J=11.76 Hz, PhCH$_2$), 4.63 (d, 1H, J=10.55 Hz, PhCH$_2$), 4.54 (d, 2H, J=12.45 Hz, PhCH$_2$), 4.45-4.37 (m, 4H, PhCH$_2$), 4.34 (d, 1H J 11.97 Hz, PhCH$_2$), 4.24 (d, 1H, J 11.96 Hz, PhCH$_2$), 4.17 (d, 2H, J=12.24 Hz, PhCH$_2$), 3.15 (t, 2H, J=5.45, 5.45 Hz, CH$_2$), 3.01 (d, 2H, J=8.18 Hz, CH$_2$), 2.55-2.44 (m, 2H, CH$_2$).

$^{13}$C NMR (126 MHz, CDCl$_3$): δC=171.40 (Amide), 138.02 (Ar), 138.01 (Ar), 137.80 (Ar), 137.54 (Ar), 136.92 (Ar), 136.86 (Ar), 128.59 (Ar), 128.42 (Ar), 128.33 (Ar), 128.30 (Ar), 128.26 (Ar), 128.24 (Ar), 128.18 (Ar), 128.10 (Ar), 127.74 (Ar), 127.71 (Ar), 127.68 (Ar), 127.61 (Ar), 127.58 (Ar), 127.39 (Ar), 127.33 (Ar), 105.94 (C-1''), 98.58 (C-1'''), 95.46 (C-1'), 84.30 (C-6), 82.53 (C-5), 82.08 (C-2''), 81.55 (C-4''), 77.01 (C-3'), 75.51 (C-4), 75.29 (C-3'''), 75.04 (PhCH$_2$), 74.33 (C-5''), 73.44 (PhCH$_2$), 73.31 (PhCH$_2$), 73.27 (PhCH$_2$), 72.76 (C-3'''), 72.27 (PhCH$_2$), 71.62 (PhCH$_2$), 71.50 (C-5'), 71.36 (C-4'''), 70.05 (C-5''), 62.41 (C-2'), 60.27 (C-1), 60.16 (C-3), 57.15 (C-2'''), 52.19 (C-6'), 51.79 (CH$_2$), 51.07 (CH$_2$), 51.05 (C-4'), 51.01 (C-6'''), 48.59 (CH$_2$), 32.46 (C-2).

MALDI TOFMS calcd for C$_{69}$H$_{78}$N$_{23}$O$_{13}$ ([M+H]+) m/e 1436.61; measured m/e 1436.67.

Preparation of 4'-(2-(aminoethylamino)acetamido)-4'-deoxy-neomycin (Compound 6; FIGS. 1 and 3)

The titled compound was prepared as was described for the preparation of Compound 1 with the following quantities: Staudinger reaction: compound 34 (0.417 gram, 0.29 mmol), THF (5 mL), PMe$_3$ (3 equiv, 6.1 mL, 6.1 mmol), aqueous NaOH (5 mL, 0.1 M). Birch reduction: THF (10 mL), ammonia (about 20 mL), small pieces of Na (80 mg, 3.48 mmol), ammonium formate (1 gram, 15.7 mmol). The analytically pure product was obtained by passing the above product through a short column of Amberlite CG50 (NH$_4^+$ form). The column was first washed with MeOH and H$_2$O, then the product was eluted with a mixture of H$_2$O/NH$_4$OH (95:5) to afford Compound 6 (92 mg, 45% for two steps). For the storage and biological tests, Compound 6 was converted to its sulfate salt form: the free base was dissolved in water, the pH was adjusted around 7.0 with H$_2$SO$_4$ (0.1 N) and lyophilized.

$^1$H NMR (500 MHz, CDCl$_3$): 'ring I': δH=5.50 (d, 1H, J=3.60 Hz, H-1), 3.84 (m, 1H, J=11.04 Hz, H-5), 3.78 (dd, J=9.85, 9.85 Hz, H-3), 3.69 (dd, J=10.37, 9.84 Hz, H-4), 2.85-2.66 (m, 3H, H-2, H-6, H-6'); 'ring II': δH=3.57-3.51 (m, 1H, H-5), 3.47-3.39 (m, 1H, H-4), 3.22 (dd, 1H, J=9.61, 9.61 Hz, H-6), 2.82-2.75 (m, 1H, H-3), 2.67-2.60 (m, 1H, H-1), 1.99 (dt, 1H, J=12.78, 3.97, 3.97 Hz, H-2eq), 1.22 (ddd, 1H, J=12.43, 12.43, 12.43 Hz, H-2ax); 'ring III': δH 5=0.33 (d, 1H, J=3.27 Hz, H-1), 4.40-4.37 (m, 1H, H-3), 4.17 (dd, 1H, J=5.48, 2.46 Hz, H-2), 4.09-4.06 (m, 1H, H-4), 3.82 (dd, 1H, J=11.95, 2.35 Hz, H-5), 3.73 (dd, 1H, J 12.33, 3.90 Hz, H-5'); 'ring IV': δH=4.95 (d, 1H, J=1.90 Hz, H-1), 3.95 (dd, 1H, J=3.11, 3.11 Hz, H-3), 3.90-3.85 (m, 1H, H-5), 3.50 (d, 1H, J=3.44 Hz, H-4), 3.06 (dd, 1H, J=13.25, 8.98 Hz, H-6), 2.98 (d, 1H, J=2.86 Hz, H-2), 2.86 (dd, 1H, J=13.34, 3.80 Hz, H-6'); the additional peaks in the spectrum were identified as follow: 3.37-3.30 (m, 2H, CH$_2$), 3.26 (d, 2H, J=16.29 Hz, CH$_2$), 2.78 (t, 2H, J=6.21, 6.21 Hz, CH$_2$).

$^{13}$C NMR (126 MHz, CDCl$_3$): δC=175.19 (Amide), 109.73 (C-1''), 100.77 (C-1', C-1'''), 86.15 (C-5), 83.90 (C-4), 83.38 (C-4''), 79.08 (C-6), 77.36 (C-3''), 76.27 (C-5'''), 75.62 (C-2''), 73.23 (C-5'), 72.11 (C-3'''), 71.59 (C-3'), 70.80 (C-4'''), 62.11 (C-5''), 58.30 (C-2'), 54.74 (C-2'''), 540.4 (C-4'), 53.04 (CH$_2$), 52.46 (C-1), 52.33 (C-3), 51.99 (C-6'), 43.36 (C-6'''), 41.69 (CH$_2$), 37.48 (C-2).

MALDI TOFMS calcd for C$_{27}$H$_{57}$N$_9$O$_{14}$ ([M+H2O]+) m/e 731.40; measured m/e 731.84.

Preparation of 4'-amino-6'-(2-(aminoethylamino) acetamido)-4'-deoxy-neomycin (Compound 9; FIGS. 1 and 3)

The titled compound was prepared as was described for the preparation of Compound 1 with the following quantities: Staudinger reaction: compound 34 (0.1 gram, 0.07 mmol), THF (5 mL), PMe₃ (3 equiv, 1.46 mL, 1.46 mmol), aqueous NaOH (5 mL, 0.1 M). Birch reduction: THF (10 mL), ammonia (about 20 mL), small pieces of Na (300 mg, 13 mmol), ammonium formate (1 gram, 15.7 mmol). The analytically pure product was obtained by passing the above product through a short column of Amberlite CG50 ($NH_4^+$ form). The column was first washed with MeOH and $H_2O$, then the product was eluted with a mixture of $H_2O/NH_4OH$ (95:5) to afford Compound 9 (37 mg, 74% for two steps). For the storage and biological tests, the compound was converted to its sulfate salt form: the free base was dissolved in water, the pH was adjusted around 7.0 with $H_2SO_4$ (0.1 N) and lyophilized.

$^1$H NMR (500 MHz, MeOD): 'ring I': δH=5.50 (d, 1H, J=3.54 Hz, H-1), 3.72-3.67 (m, 1H, H-5), 3.43 (dd, 1H, J=9.77, 9.77 Hz, H-3), 3.01 (dd, 1H, J=13.48, 2.72 Hz, H-6), 2.77 (dd, 1H, J=13.67, 6.80 Hz, H-6'), 2.68 (dd, 1H, J=10.21, 3.73 Hz, H-2), 2.49 (dd, 1H, J=9.75, 9.75 Hz, H-4); 'ring II': δH=3.57-3.49 (m, 1H, H-5), 3.43 (dd, 1H, J=9.51, 9.51 Hz, H-4), 3.34 (dd, 1H, J=9.02, 9.02 Hz, H-6), 2.82-2.74 (m, 1H, H-3), 2.67-2.59 (m, 1H, H-1), 2.01-1.93 (m, 1H, H-2eq), 1.25-1.17 (m, 1H, H-2ax); 'ring III': δH=5.28 (d, 1H, J=3.47 Hz, H-1), 4.38-4.35 (m, 1H, H-3), 4.17-4.14 (m, 1H, H-2), 4.06-4.03 (m, 1H, H-4), 3.82-3.77 (m, 1H, H-5), 3.73-3.68 (m, 1H, H-5'); 'ring IV': δH=5.29 (d, 1H, J=3.68 Hz, H-1), 3.66-3.57 (m, 1H, H-5), 3.50 (dd, 1H, J=10.02, 10.02 Hz, H-6), 3.12 (dd, 1H, J=12.77, 4.73 Hz, H-3), 2.73 (dd, 1H, J=9.88, 3.69 Hz, H-4), 2.52 (dd, 1H, J=11.59, 11.59 Hz, H-2), 2.39-2.34 (m, 1H, H-6'); the additional peaks in the spectrum were identified as follow: δH 3.91-3.86 (m, 1H, $CH_2$), 3.47-3.40 (m, 1H, $CH_2$), 3.30 (s, 2H, $CH_2$), 2.76-2.73 (m, 2H, $CH_2$).

$^{13}$C NMR (126 MHz, MeOD): δC=174.80 (Amide), 110.05 (C-1"), 100.65 (C-1'"), 100.61 (C-1'), 85.91 (C-5), 85.50 (C-6), 83.31 (C-3'), 83.16 (C-4, C-4"), 77.13 (C-3"), 75.74 (C-5"), 75.54 (C-2"), 72.02 (C-3'"), 70.69 (C-4'"), 69.08 (C-5'), 62.07 (C-5"), 61.87 ($CH_2$), 57.67 (C-2'), 56.13 (C-4'), 54.67 (C-2'"), 52.31 (C-1, C-3), 48.83 ($CH_2$), 43.68 (C-6'), 43.23 ($CH_2$), 43.20 (C-6'"), 37.38 (C-2).

MALDI TOFMS calcd for $C_{27}H_{57}N_9O_{14}$ ($[M+H_2O]+$) m/e 731.40; measured m/e 731.84).

Preparation of 4'-[2-(2-((benzyloxycarbonyl) (methyl)amino) ethylamino)acetamido]-4'-deoxy-2", 3',3'",4'",5",6-hexa-Obenzyl-1,2',2'",3,6',6'"-hexaazido-neomycin (35)

The titled compound was prepared as was described for the preparation of compound 27 with the following quantities: compound 33 (0.5 gram, 0.36 mmol), DMF (10 mL), N,N-diisopropylethylamine (0.25 mL, 1.43 mmol, 4 eq.), N-Cbz-N-Methylethylenediamine (0.3 gram, 1.44 mmol, 4 eq.) The crude product was purified by flash chromatography (Hexane/EtOAc, 6:4) to afford compound 35 (0.365 gram, 65%).

$^1$H NMR (500 MHz, CDCl₃): 'Ring I': δH=6.27 (d, 1H, J=3.7 Hz, H-1), 4.08-3.97 (m, 2H, H-5, H-3), 3.85 (dd, 1H, J=12.2, 9.9 Hz, H-4), 3.33 (dd, 1H, J=13.7, 7.2 Hz, H-6), 3.23 (dd, 1H, J=13.1, 2.2 Hz, H-6'), 3.03 (dd, 1H, J=10.8, 2.4 Hz, H-2); 'Ring II': δH=3.94 (dd, 1H, J=8.5 Hz, H-5), 3.69 (dd, 1H, J=8.8 Hz, H-4), 3.48-3.32 (m, 2H, H-1, H-3), 3.28 (dd, 1H, J=7.3 Hz, H-6), 2.09 (dt, 1H, J=12.8, 4.6 Hz, H-2eq), 1.35 (ddd, 1H, J=12.3, 5.3 Hz, H-2ax); 'Ring III': δH=5.68 (d, 1H, J=5.2 Hz, H-1), 4.31-4.26 (m, 2H, H-3, H-4), 3.95 (dd, 1H, J=6.1, 5.1 Hz, H-2), 3.82 (dd, 1H, J=10.1, 1.4 Hz, H-5), 3.56 (dd, 1H, J=10.4, 2.5 Hz, H-5'); 'Ring IV': δH=4.95 (d, 1H, J=1.5 Hz, H-1), 3.83-3.74 (m, 2H, H-3, H-5), 3.67 (dd, 1H, J=12.7, 9.1 Hz, H-6), 3.36 (dd, 1H, J=5.6, 1.8 Hz, H-2), 3.13 (dd, 1H, J=2.3, 1.6 Hz, H-4), 2.85 (dd, 1H, J=14.9, 2.9 Hz, H-6'); the additional peaks in the spectrum were identified as follow: 7.45-7.12 (m, 35H, Ar), 7.2 (d, 1H, J=8.79 Hz, Amide), 5.11 (d, 1H, J=12.4 Hz, PhCH₂), 5.09 (m, 2H, $CH_2$ of Cbz), 4.95 (d, 1H, J=16.0 Hz, PhCH2), 4.72 (d, 1H, J=10.6 Hz, PhCH₂), 4.62 (d, 1H, J=12.5 Hz, PhCH₂), 4.57 (d, 1H, J=11.2 Hz, PhCH₂), 4.49 (d, 1H, J=12.6 Hz, PhCH₂), 4.46 (m, 2H, PhCH₂), 4.42 (d, 1H, J=12.0 Hz, PhCH₂), 4.32 (d, 1H, J=12.0 Hz, PhCH₂), 4.29 (d, 1H, J=14.2 Hz, PhCH₂), 4.25 (d, 1H, J=12.1 Hz, PhCH₂), 3.37-3.35 (m, 2H, O=CCH₂NHR), 3.24-3.21(m, 1H, $CH_2$), 3.13 (m, 1H, $CH_2$), 2.96 (m, 1H, $CH_2$), 2.87 (m, 1H, $CH_2$), 2.17 (m, 3H, $CH_3$).

$^{13}$C NMR (125 MHz, CDCl₃): δC=170.42 (Amide), 156.14 (Carbamate), 137.51 (Ar), 135.11 (Ar), 134.57 (Ar), 133.45 (Ar), 132.45 (Ar), 132.13 (Ar), 131.95 (Ar), 131.54 (Ar), 130.97 (Ar), 128.93 (Ar), 128.65 (Ar), 127.87 (Ar), 127.66 (Ar), 127.41 (Ar), 127.13 (Ar), 126.49 (Ar), 125.83 (Ar), 111.85(C-1"), 107.30 (C-1'"), 106.73 (C-1'), 87.52 (C-4"), 86.63 (C-4'"), 83.21 (C-2"), 77.40 (C-3"), 76.82 (C-3'"), 75.23 (C-6), 75.06 (C-3'), 74.27 (C-5), 73.56 (C-5'), 73.35 (PhCH₂), 73.04 (PhCH₂), 72.95 (C-5'"), 72.71 (PhCH₂), 72.53 (C-4), 71.68 (PhCH₂), 70.82 (PhCH₂), 68.51 (C-5"), 67.12 ($CH_2$ of Cbz), 61.81(C-2'"), 56.93 (C-4'), 56.12 (C-2'), 54.26 ($CH_2$), 53.50 (RCH₂C=ONHR), 52.78 (C-3), 51.16 (C-1), 47.64 (C-6'"), 45.23 ($CH_2$), 44.87 (C-6'), 37.08 (CH₃NHR), 36.25 (C-2).

TOFMS calcd for $C_{78}H_{87}N_{21}O_{15}Na$ ([M+Na]+) m/e 1580.66; measured m/e 1580.71).

Preparation of 4'-[2-(2-((benzyloxycarbonyl) (methyl)amino)ethylamino) acetamido]-4'-deoxy-neomycin (Compound 7; FIGS. 1 and 3)

The titled compound was prepared as described for the preparation of Compound 1 with the following quantities: Staudinger reaction: compound 35 (365 mg, 0.234 mmol), THF (10 mL), NaOH (0.1M, 5 mL), PMe₃ (1M solution in THF, 5.9 mL, 57 mmol) to yield the compound as free amine form. Birch reduction: THF (10 mL), ammonia (about 20 mL), small pieces of Na (65 mg, 2.8 mmol), ammonium formate (1 gram, 15.7 mmol). The analytically pure product was obtained by passing the above product through a short column of Amberlite CG50 ($NH_4^+$ form). The column was first washed with MeOH and $H_2O$, then the product was eluted with a mixture of $H_2O/NH_4OH$ (91:9) to afford Compound 7 (95 mg, 68% for two steps). For the storage and biological tests, compound was converted to its sulfate salt form: the free base was dissolved in water, the pH was adjusted around 7.0 with $H_2SO_4$ (0.1 N) and lyophilized.

$^1$H NMR (500 MHz, MeOD): 'Ring I': δH=5.74 (d, 1H, J=3.3 Hz, H-1), 4.10 (dd, 1H, J=9.6, 5.2 Hz, H-4), 3.83-3.71 (m, 2H, H-5, H-3), 3.00-2.92 (m, 2H, H-6, H-6'), 2.84 (dd, 1H, J=12.2, 2.1 Hz, H-2); 'Ring II': δH=3.56 (dd, 1H, J=11.5, 7.4 Hz, H-5), 3.46 (dd, 1H, J=10.5, 8.9 Hz, H-4), 3.23 (dd, 1H, J=10.3, 9.1 Hz, H-6), 2.81 (ddd, 1H, J=12.7, 9.1 Hz, H-1), 2.65 (ddd, 1H, J=12.7, 9.8 Hz, H-3), 2.00 (dt, 1H, J=9.1, 4.1 Hz, H-2eq), 1.24 (ddd, 1H, J=12.3, 1.2 Hz, H-2ax); 'Ring III': δH=5.41 (d, 1H, J=2.4 Hz, H-1), 4.40 (dd, 1H, J=6.5, 4.9 Hz, H-3), 4.18 (dd, 1H, J=5.1, 2.4 Hz, H-2), 4.09 (dd, 1H, J=6.0, 1.3 Hz, H-4), 3.91 (dd, 1H, J=11.1, 1.5 Hz, H-5), 3.78 (dd, 1H, J=11.5, 3.3 Hz, H-5'); 'Ring IV': δH=4.97 (d, 1H, J=1.6 Hz, H-1), 3.97 (dd, 1H, J=4.0, 2.4 Hz, H-3), 3.53-3.51 (m, 2H, H-4, H-5), 3.00 (dd, 1H, J=3.6, 1.6 Hz, H-2), 2.82 (dd, 1H, 9.3 Hz, H-6), 2.68

(dd, 1H, J=2.9 Hz, H-6'); the additional peaks in the spectrum were identified as follow: 3.37-3.35 (m, 1H, RCH$_2$C=ONHR), (m, 2H, RHN(CH$_2$)$_2$NHR), 2.62 (m, 3H, CH$_3$NHR).

$^{13}$C NMR (125 MHz, MeOD): δC=174.58 (Amide), 109.87(C-1''), 100.70 (C-1'''), 100. 61(C-1'), 86.15 (C-5), 83.36 (C-4''), 79.11 (C-6), 77.26 (C-3''), 76.12 (C-2''), 75.60 (C-3'), 74.82 (C-3'''), 74.43 (C-4), 73.10 (C-5'''), 72.07 (C-5'), 71.02 (C-4'''), 63.79 (C-2'''), 62.90 (RCH$_2$C=ONHR), 62.03 (C-5''), 59.42 (CH$_2$), 58.87 (CH$_2$), 58.18 (C-4'), 57.77 (C-3), 56.07 (C-2'), 54.23 (C-1), 52.38, 51.62, 46.05, 45.10, 43.31 (C-6'''), 42.74 (C-6'), 41.71, 39.20 (CH$_3$NHR), 37.46 (C-2).

TOFMS calcd for $C_{28}H_{57}N_9O_{13}K$ ([M+K]+) m/e 766.41; measured m/e 766.67).

Preparation of 4'-[2-(2-(2-aminoethylamino)ethylamino)acetamido]-4'-deoxy-2'',3',3''',4'',5'',6-hexa-O-benzyl-1,2',2''',3,6',6'''-hexaazido-neomycin (36)

Compound 33 (0.5 gram, 0.36 mmol) was dissolved in DMF (40 mL) followed by the addition of diethylenetriamine (0.4 mL, 0.37 mmol) and the reaction was left to stir at room temperature. The reaction progress was monitored by TLC [EtOAc/MeOH/MeNH$_2$ (33% solution in EtOH), 10:10:1] which indicated completion after 12 hours. After completion of the reaction the solvent was evaporated and the crude product was purified by flash chromatography (CHCl$_3$/MeOH, 80:20) to afford compound 36 (0.62 gram, quantitative).

$^1$H NMR (500 MHz, CDCl$_3$): 'ring I': δH=6.25 (d, 1H, J=4.18 Hz, H-1), 4.33-4.27 (m, 1H, H-5), 4.00 (dd, 1H, J=9.88, 9.88 Hz, H-3), 3.91 (dd, 1H, J=10.73, 10.05 Hz, H-4), 3.38-3.31 (m, 2H, H-6, H-6'), 3.15 (dd, 1H, J=10.27, 3.00 Hz, H-2); 'ring II': δH=3.87 (dd, 1H, J=8.99, 8.99 Hz, H-5), 3.73 (dd, 1H, J=10.16, 9.35 Hz, H-4), 3.65-3.55 (m, 2H, H-1, H-3), 3.35 (dd, 1H, J=9.74, 8.93 Hz, –6H), 2.29 (dt, 1H, J=12.42, 4.37, 4.37 Hz, H-2eq), 1.45 (ddd, 1H, J=12.51, 12.49, 12.49 Hz, H-2ax); 'ring III': δH=5.65 (d, 1H, J=4.48 Hz, H-1), 4.30 (dd, 1H, J=4.15, 4.15 Hz, H-3), 4.25-4.23 (m, 1H, H-4), 4.05 (dd, 1H, J=4.91, 4.91 Hz, H-2), 3.84 (dd, 1H, J=10.69, 2.47 Hz, H-5), 3.61 (dd, 1H, J=10.54, 3.99 Hz, H-5'); 'ring IV': δH=4.92 (d, 1H, J=1.99 Hz, H-1), 3.92-3.86 (m, 2H, H-3, H-5), 3.60 (dd, 1H, J=12.35, 9.50 Hz, H-6), 3.39-3.33 (m, 2H, H-2, H-4), 3.17-3.08 (m, 1H, H-6'); the additional peaks in the spectrum were identified as follow: 7.43-7.21 (m, 30H, Ar), 4.94 (d, 1H, J=10.93 Hz, BnCH$_2$), 4.78 (d, 1H, J=10.89 Hz, BnCH$_2$), 4.74 (d, 1H, J=11.33 Hz, BnCH$_2$), 4.64 (d, 1H, J=11.65 Hz, BnCH$_2$), 4.60 (d, 1H, J=11.25 Hz, BnCH$_2$), 4.57-4.50 (m, 5H, BnCH$_2$), 4.44 (d, 1H, J=12.12 Hz, BnCH$_2$), 4.41 (d, 1H, J=11.61 Hz, BnCH$_2$), 3.21 (s, 2H, BnCH$_2$), 2.86-2.73 (m, 4H, CH$_2$), 2.70-2.60 (m, CH$_2$).

$^{13}$C NMR (126 MHz, CDCl$_3$): δC=174.44 (Amide), 139.63 (Ar), 139.52 (Ar), 139.16 (Ar), 138.95 (Ar), 138.87 (Ar), 129.66 (Ar), 129.59 (Ar), 129.49 (Ar), 129.46 (Ar), 129.38 (Ar), 129.37 (Ar), 129.22 (Ar), 129.02 (Ar), 128.92 (Ar), 128.78 (Ar), 128.75 (Ar), 128.73 (Ar), 128.59 (Ar), 108.31 (C-1''), 99.95 (C-1'''), 97.22 (C-1'), 85.44 (C-6), 83.53 (C-4''), 83.39 (C-5), 83.00 (C-2''), 78.91, 78.23 (C-3'), 77.60, 77.29 (C-3''), 77.12 (C-4), 76.08 (BnCH$_2$), 75.72, 75.60, 75.14, 74.70, 74.62 (BnCH$_2$), 74.45 (BnCH$_2$), 74.26 (BnCH$_2$), 73.62 (BnCH$_2$), 73.49, 73.07 (BnCH$_2$), 72.18, 72.12 (C-5'), 71.65 (C-5''), 64.23 (C-2'), 62.88, 61.78, 61.14 (C-1, C-3), 58.59 (C-2'''), 57.43, 53.00 (C-6'), 52.94 (C-4'), 52.76 (CH$_2$), 52.43, 52.37 (C-6'''), 49.68 (CH$_2$), 49.62 (CH$_2$), 41.46 (CH$_2$), 33.11 (C-2).

MALDI TOFMS calcd for $C_{71}H_{84}N_{22}O_{13}$ ([M+Na]+) m/e 1475.65; measured m/e 1475.23).

Preparation of 4'-amino-6'-[2-(2-(2-aminoethylamino)ethylamino) acetamido]-4'-deoxy-neomycin (Compound 10; FIGS. 1 and 3)

The titled compound was prepared as described for the preparation of Compound 1 with the following quantities: Staudinger reaction: Compound 36 (580 mg, 0.4 mmol), THF (10 mL), NaOH (0.1M, 5 mL), PMe$_3$ (1M solution in THF, 14.5 mL, 14.5 mmol) to yield the compound as free amine form. Birch reduction: THF (10 mL), ammonia (about 20 mL), small pieces of Na (500 mg, 21.7 mmol), ammonium formate (1 gram, 15.7 mmol). The analytically pure product was obtained by passing the above product through a short column of Amberlite CG50 (NH$_4^+$ form). The column was first washed with MeOH and H$_2$O, then the product was eluted with a mixture of H$_2$O/NH$_4$OH (91:9) to afford Compound 10 (109 mg, 36% for two steps). For the storage and biological tests, the compound was converted to its sulfate salt form: the free base was dissolved in water, the pH was adjusted around 7.0 with H$_2$SO$_4$ (0.1 N) and lyophilized.

$^1$H NMR (500 MHz, D$_2$O): 'ring I': δH=5.28 (d, 1H, J=3.39 Hz, H-1), 3.77 (ddd, 1H, J=12.61, 5.62, 2.95 Hz, H-5), 3.56 (dd, 1H, J=14.28, 4.50 Hz, H-6), 3.42 (dd, 1H, J=14.62, 3.09 Hz, H-6'), 3.40 (dd, 1H, J=9.80, 9.80 Hz, H-3), 2.66 (dd, 1H, J=10.17, 3.71 Hz, H-2), 2.47 (dd, 1H, J=9.59, 9.59 Hz, H-4); 'ring II': δH=3.64-3.55 (m, 1H, H-5), 3.43-3.32 (m, 1H, H-4), 3.26-3.17 (m, 1H, H-6), 2.88-2.75 (m, 1H, H-3), 2.71-2.64 (m, 1H, H-1), 1.90 (dt, 1H, J=9.05, 3.92, 3.92 Hz, H-2eq), 1.22-1.07 (m, 1H, H-2ax); 'ring III': δH=5.43 (d, 1H, J=5.42 Hz, H-1), 4.55-4.49 (m, 1H, H-3), 4.40-4.33 (m, 1H, H-2), 4.25-4.20 (m, 1H, H-4), 3.98-3.94 (m, 1H, H-5), 3.83-3.79 (m, 1H, H-5); 'ring IV': δH=5.06 (d, 1H, J=2.40 Hz, H-1), 4.11 (dd, J=3.83, 3.83 Hz, H-3), 4.10-3.99 (m, 1H, H-5), 3.74 (dd, 1H, J=2.10, 2.10 Hz, H-4), 3.19-3.09 (m, H, H-6), 3.12 (dd, 1H, J=4.01, 1.99 Hz, H-2), 3.07-2.98 (m, 1H, H-6'); the additional peaks in the spectrum were identified as follow: 3.44 (s, 2H, CH$_2$), 3.05-2.79 (m, 8H, CH$_2$).

$^{13}$C NMR (126 MHz, D$_2$O): δC=174.39 (Amide), 108.57 (C-1''), 99.49 (C-1'), 99.40 (C-1'''), 84.08 (C-5), 83.61 (C-4), 81.69 (C-4''), 77.42 (C-6), 76.10 (C-3''), 75.17 (C-5'''), 73.47 (C-2''), 73.08 (C-3'), 72.44 (C-5'), 70.71 (C-3'''), 68.62 (C-4'''), 61.42 (C-5''), 55.86 (C-2'), 53.94 (C-4'), 52.76 (C-2'''), 51.06 (CH$_2$), 50.42 (C-1, C-3), 48.23 (CH$_2$), 47.62 (CH$_2$), 47.26 (CH$_2$), 41.17 (C-6'''), 39.99 (C-6'), 39.06 (CH$_2$), 35.63 (C-2).

MALDI TOFMS calcd for $C_{29}H_{60}N_{10}O_{13}$ ([M]+) m/e 756.43; measured m/e 756.40).

Preparation of 4'-[2-(2-(2-aminoethylamino)ethylamino)acetamido]-4'-deoxy-neomycin (Compound 8; FIGS. 1 and 3)

The titled compound was prepared as described for the preparation of Compound 1 with the following quantities: Staudinger reaction: Compound 36 (580 mg, 0.4 mmol), THF (10 mL), NaOH (0.1M, 5 mL), PMe$_3$ (1M solution in THF, 14.5 mL, 14.5 mmol) to yield the compound as free amine form. Birch reduction: THF (10 mL), ammonia (about 20 mL), small pieces of Na (55 mg, 2.31 mmol), ammonium formate (1 gram, 15.7 mmol). The analytically pure product was obtained by passing the above product through a short column of Amberlite CG50 (NH$_4^+$ form). The column was first washed with MeOH and H$_2$O, then the product was eluted with a mixture of H$_2$O/NH$_4$OH (91:9) to afford Compound 8 (60.2 mg, 20% for two steps). For the storage and biological tests, compound was converted to its sulfate salt form: the free base was dissolved in water, the pH was adjusted around 7.0 with H$_2$SO$_4$ (0.1 N) and lyophilized.

$^1$H NMR (500 MHz, MeOD): 'ring I': δH=5.52 (d, 1H, J=3.52 Hz, H-1), 3.89-3.84 (m, 1H, H-5), 3.80 (dd, 1H J=10.12, 10.12 Hz, H-3), 3.71 (dd, 1H, J=10.12, 9.16 Hz, H-4), 2.82 (ddd, 1H, J=13.68, 2.48, 1.04 Hz, H-6), 2.77-2.69 (m, 2H, H-2, H-6'); 'ring II': δH=3.56 (dd, 1H, J=8.50, 4.82 Hz, H-5), 3.46 (dd, 1H, J=8.89, 8.89 Hz, H-4), 3.24 (dd, 1H, J=11.10, 7.66 Hz, H-6), 2.85-2.78 (m, 1H, H-3), 2.71-2.62 (m, 1H, H-1), 2.01 (dt, 1H, J=12.84, 3.76, 3.76 Hz, H-2eq), 1.24 (ddd, 1H, J=12.32, 12.32, 12.32 Hz, H-2ax).); 'ring III': δH=5.37 (d, 1H, J=3.28 Hz, H-1), 4.43-4.39 (m, 1H, H-3), 4.23-4.18 (m, 1H, H-2), 4.12-4.09 (m, 1H, H-4), 3.86-3.81 (m, 1H, H-5), 3.75 (dd, 1H, J=7.61, 4.44 Hz, H-5'); 'ring IV': δH=4.97 (d, 1H, J=2.10 Hz, H-1), 3.98 (dd, 1H, J=3.34, 3.34 Hz, H-3), 3.93-3.89 (m, 1H, H-5), 3.53 (bs, 1H, H-4), 3.08 (dd, 1H, J=12.89, 8.13 Hz, H-6), 3.01 (bs, 1H, H-2), 2.89 (dd, 1H, J=13.67, 4.21 Hz, H-6'); the additional peaks in the spectrum were identified as follow: 3.43-3.23 (m, 2H, CH$_2$), 2.91-2.79 (m, 2H, CH$_2$), 2.85-2.86 (m, 6H, CH$_2$).

$^{13}$C NMR (126 MHz, MeOD): δC=175.18 (Amide), 109.80 (C-1''), 100.73 (C-1', C-1'''), 86.06 (C-5), 83.95 (C-4), 83.37 (C-2''), 79.01 (C-6), 77.42 (C-3''), 76.28 (C-5'''), 75.54 (C-4''), 73.18 (C-5'), 72.11 (C-3''', C-3'), 70.77 (C-4'''), 62.20 (C-5''), 58.26 (C-2'), 54.74 (C-2'''), 54.06 (C-4'), 52.44 (C-1), 53.16 (CH$_2$), 52.35 (C-3), 51.72 (CH$_2$), 49.69 (CH$_2$), 43.52 (C-6'), 43.34 (C-6'''), 41.49 (CH$_2$), 37.48 (C-2).).

MALDI TOFMS calcd for C$_{29}$H$_{60}$N$_{10}$O$_{13}$ ([M]+) m/e 756.43; measured m/e 756.74).

Example 3

Antibacterial Activity and Protein Translation Inhibition

The minimal inhibitory concentration (MIC) values of the newly designed exemplary Compounds 1-10 were determined against wild-type (WT) Gram-negative and Gram-positive bacteria.

The bacterial strains that were included in these tests were as follows:

Two wild-type (WT) E. coli strains (R477-100 and 25922) as representatives of Gram-negative bacteria with unknown resistance to aminoglycosides [V. Pokrovskaya, V. Belakhov, M. Hainrichson, S. Yaron, T. Baasov, J. Med. Chem. 2009, 52, 2243-2254] and two WT Staphylococcus epidermidis and Bacillus subtilis strains as representatives of Gram-positive bacteria (the clinically used aminoglycosides have significant antibacterial activity against these strains) [J. Kondo, M. Hainrichson, I. Nudelman, D. Shallom-Shezifi, C. M. C. M. Barbieri, D. S. D. S. Pilch, E. Westhof, T. Baasov, ChemBioChem 2007, 8, 1700-1709].

The resistant strains included MRSA, a Gram-positive bacterium, the treatment of which represents a great challenge in the clinic; MRSA 252, which is known for its high resistance to aminoglycosides [M. T. G. Holden, E. J. Feil, J. A. Lindsay, S. J. Peacock, N. P. J. Day, M. C. Enright, T. J. Foster, C. E. Moore, L. Hurst, R. Atkin, et al., Proc. Natl. Acad. Sci. USA 2004, 101, 9786-9791]; and MRSA CI 15877, which is resistant to natural aminoglycosides [G. Kaneti, H. Sarig, I. Marjieh, Z. Fadia, A. Mor, FASEB J. 2013, 27, 4834-4843].

Other pathogens that were tested included several strains of P. aeruginosa that have an inherent resistance to aminoglycosides [J. I. Sekiguchi, T. Asagi, T. Miyoshi-Akiyama, T. Fujino, I. Kobayashi, K. Morita, Y. Kikuchi, T. Kuratsuji, T. Kirikae, Antimicrob. Agents Chemother. 2005, 49, 3734-3742; M. Hainrichson, O. Yaniv, M. Cherniavsky, I. Nudelman, D. Shallom-Shezifi, S. Yaron, T. Baasov, Antimicrob. Agents Chemother. 2007, 51, 774-776].

FIG. 5 presents a table showing the comparative MIC values of NeoB and Compounds 1-10 against the tested Gram-negative and Gram-positive, pathogenic and resistant, strains.

The comparative data presented in FIG. 5 (Table 1) show that all the new derivatives of NeoB, Compounds 2-10, exhibit significant antibacterial activity against both the WT and aminoglycoside-resistant strains, including Gram-negative and Gram-positive bacteria.

The activities against the WT Gram-positive bacteria were diverse across the different strains tested. The activity of most of the compounds against S. epidermidis is similar to or better than that of NeoB.

All new derivatives (Compounds 2-10) show significantly improved activity against the Gram-negative strains of pathogenic P. aeruginosa in comparison with NeoB.

P. aeruginosa is a nosocomial human pathogen known to be inherently resistant to aminoglycosides owing to the presence of the chromosomally encoded APH(3')-IIb enzyme. This enzyme catalyzes the transfer of the ATP g-phosphoryl group to the 3'-hydroxy group of many aminoglycosides, rendering them inactive as antibiotics [34] The observed improved activity of the new derivatives relative to that of NeoB against the tested strains of P. aeruginosa can be explained by the steric hindrance of the cationic warhead, which introduces unfavorable interactions with the APH(3')-IIb enzyme active site.

An improvement in antibacterial performance of the Compounds 2-10 versus that of NeoB was also observed against the Gram-positive pathogenic MRSA strains. For example, Compounds 2 and 8 exhibited MIC values that were 64 times lower than that of NeoB. The 4'-ether (Compounds 1-5) and 4'-amide (Compounds 6-8) compounds exhibited substantially the same activity.

The antibacterial activity of Compound 1, a neamine-based derivative, is substantially lower than that of the other compounds tested, indicating that its binding affinity to the A-site is much lower.

Compounds 1-10 all showed antibacterial activity against the WT Geobacillus T1, also at 60° C. Against the Geobacillus T1 harboring the resistance to kanamycin, most of the new compounds maintained their high antibacterial activity, whereas NeoB almost lost its activity.

As can be seen, the introduced modifications to the NeoB structure did not hinder the binding to the A-site and most of the derivatives retained significant antibacterial activity. Moreover, the new compounds overcame the existing resistance of P. aeruginosa and MRSA pathogens to aminoglycosides.

The protein translation inhibition was next tested by determining half-maximum inhibition levels (IC$_{50}$ values, Table 1). While most of the new compounds showed activity of the same order of magnitude as NeoB, the inhibitory potency of Compounds 6, 9, and 10 with a 4'-nitrogen atom was two-fold higher than that of NeoB (IC$_{50}$ values of 0.006, 0.005, 0.006, and 0.01 for Compounds 6, 9, 10, and for NeoB, respectively).

Without being bound by any particular theory, it is assumed that this may result from the additional interactions of the 4'-amide (Compound 6) and 4'-amine (Compounds 9 and 10) groups of these compounds with the ribosomal A-site.

Example 4

RNase Activity Tests

The potential RNase activity of Compounds 1-10 was tested using gel electrophoresis experiments, as previously reported for ColE3 [C. L. Ng, K. Lang, N. A. G. Meenan, A. Sharma, Nat. Struct. Mol. Biol. 2010, 17, 1241-1246]. Experiments were first performed on full-size ribosomes isolated from *E. coli*, as previously reported [B. a. Maguire, L. M. Wondrack, L. G. Contillo, Z. Xu, RNA 2008, 14, 188-195].

As a positive control, the RNase domain of the natural toxin ColE3 was used (see, FIG. 6B). As shown in FIG. 6B, with ColE3, cleavage of approximately 40 bases from the 16S rRNA fragment (about 1540 nucleic bases) was observed, in a dose-dependent manner.

As shown in FIGS. 6C and 6D, for the 5S and tRNA fragments, NeoB and Compound 3 did not show any signs of the cleaved product at concentrations up to 400 mm. At higher concentrations, solubility issues prevented detecting RNA cleavage.

As shown in FIG. 6A, within the same concentration range (up to 400 mm), ethylenediamine (a negative control) did not cleave the full ribosome, suggesting that it is unable to bind to rRNA effectively.

An A-site oligonucleotide model was next tested. An oligonucleotide model similar to that used by Westhof and co-workers [P. Pfister, S. Hobbie, Q. Vicens, E. C. Bçttger, E. Westhof, ChemBioChem 2003, 4, 1078-1088; Q. Vicens, E. Westhof, Chem. Biol. 2002, 9, 747-755] for crystallographic studies was selected. To improve RNA detection, a fluorescent Cy3 tag was added at the 3' end (and not at the 5' end) to ensure that there was a significant difference between the size of the full-length RNA and the cleaved RNA, as shown in FIGS. 7A-B.

The cleavage experiments indicated that with ethylenediamine (N-2-N) non-specific cleavage was observed at high concentrations, 100 and 200 mm of N-2-N, as shown in FIG. 8A.

In the presence of Compound 6, some RNA cleavage was detected at substantially lower concentrations, 10 mm, as shown in FIG. 8B. Double-stranded RNA (DS band in FIG. 8B) was also observed, suggesting that the aminoglycoside binding stabilized double-stranded RNA even though the gel was under denaturing conditions. Only nonspecific cleavage bands were observed at the concentrations tested, and these fragments were longer than those expected for specific and selective cleavage (<8 bases).

Example 5

MD Simulations
Conformational Dynamics of the Warheads and the Possibility of RNA Cleavage:

Full-atom molecular dynamics (MD) followed by Gaussian accelerated MD (GaMD) [Y. Miao, V. A. Feher, J. A. McCammon, J. Chem. Theory Comput. 2015, 11, 3584-3595; Y. T. Pang, Y. Miao, Y. Wang, J. A. McCammon, J. Chem. Theory Comput. 2017, 13, 9-19] was performed. The crystal structure of NeoB bound to the oligonucleotide model of the A-site rRNA (PDB ID:2ET4) [supra] was used as a template for building the systems used in the simulations.

The model of the A site contains two symmetric aminoglycoside binding sites using the crystal structure of the A site with bound neomycin B (PDB code: 2ET4). The Compounds 2, 5, 8, and 10 were built with leap (Ambertools 17) based on the geometry of NeoB in the crystal structure (PDB ID: 2ET4). The initial structures of the warheads were entirely linear not to favor any conformation. All terminal amine groups in aminoglycosides were protonated. The aminoglycoside geometries were optimized at the HF/6-31G (d)//B3LYP/6-31G(d) level of theory and docked to the A site by alignment to the neomycin moiety. The systems were then solvated by adding 15 Å layer of water molecules. Total molecular charge of RNA was −40e and the charge of Compounds 2, 5, 8, and 10 was +7e each. The negative charge of the system was neutralized with sodium ions and the ionic strength of 0.1 M NaCl was added. The atomic charges of aminoglycosides were obtained using the RESP procedure2 with Gaussian 09 and antechamber (Ambertools17) [D. A. Case, I. Y. Ben-Shalom, S. R. Brozell, D. S. Cerutti, T. E. Cheatham, III, V. W. D. Cruzeiro, T. A. Darden, R. E. Duke, D. Ghoreishi, M. K. Gilson, H. Gohlke, A. W. Goetz, D. Greene, R Harris, N. Homeyer, S. Izadi, A. Kovalenko, T. Kurtzman, T. S. Lee, S. LeGra, D. M. Y. and P. A. K. AMBER 2018. Univ. California, San Fr. 2018]. Their bonded and non-bonded parameters were assigned with GAFF2 using antechamber and parmchk2 programs (Ambertools17). For RNA, the parameters of ff99OL3 were applied. TIP3P-FB model was used for explicit water molecules [Wang, L. P.; Martinez, T. J.; Pande, V. S. Building Force Fields: An Automatic, Systematic, and Reproducible Approach. *J. Phys. Chem. Lett.* 2014, 5 (11), 1885-1891]. The simulated system is shown in FIG. 9. Compounds 2, 5, 8, and 10, as representative examples, were simulated, and NeoB was used as a control. The total MD and GaMD simulation time was about 5.5 ms. For compounds 2 and 5, two and three different conformations of the warheads, respectively, were found, as shown in FIGS. 10 and 11. For both compounds, the dominant conformation of the warhead (82.7% of the population in 2 and 76.4% of the population in 5) is characterized by a common intramolecular hydrogen bond between the N1 amine of the warhead and the N6' ammonium of the aminoglycoside ring I. These intramolecular hydrogen bonds may prevent the N1 amine of the warhead from acting as the general base to activate the 2'-OH group of the G1491 ribose as a nucleophile (see FIGS. 4A-B for the proposed mechanism).

As shown in FIGS. 12A-D and 13, the warhead of Compounds 8 and 10, which represent the 4'- and 6'-amide derivatives of NeoB, is longer and does not form intramolecular interactions with the rest of the molecule.

For Compound 10, as shown in FIGS. 12A-D, the largest conformational variability of the warhead was observed and is associated with its rotation around the N2-C3-C4—N3 dihedral angle (FIG. 12B).

This coordinate was used in the clustering analysis and two major conformations of the warhead (72.2 (FIG. 12C) and 27.8% of the population (FIG. 12A)) were found (FIG. 12D). The short range contacts of the N4' ammonium with the phosphates of A1492 and A1493 conformationally restrict the position of ring I in the A-site and also the A1492 and A1493 backbone atoms.

For compound 8, three principal modes of binding of the warhead to the rRNA were observed (see, FIG. 13). In the most abundant binding mode (58.6% of the population), two short-range interactions between the 2'-hydroxy group of the ribose (G1491) and the N3 amine group of Compound 8 (proposed general base) and between the A1492 phosphate and the N4 ammonium of Compound 8 (general acid) were observed. This conformational state of Compound 8 is consistent with the suggested mechanism of A-site rRNA cleavage between G1491 and A1492, shown in FIG. 4B. In the second most-abundant binding mode of Compound 8 (21.6% of the population), the N2 amine group forms a hydrogen bond with the 2'-hydroxy group of the ribose of G1491, which actually serves as the general base. The concomitant stabilization of the transition state through the interaction of the warhead amines with the phosphate of A1492 is lacking.

Compound 8 thus exhibits the interactions required for Asite rRNA cleavage between G1491 and A1492. The N3 amine of the warhead activates the 2'-OH group of the G1491 ribose for nucleophilic attack, and the N4 ammonium of the warhead favorably binds to the OP2 and O3' atoms of the A1492 phosphate, which facilitates nucleophilic attack.

In general, the efficiency of rRNA hydrolysis is highly dependent on the ability to induce the correct positioning of the nucleophile for in-line attack on the scissile bond. Enzymes, being large, can mechanically achieve this step "easily" by distorting the substrate to reach the conformation necessary for efficient catalysis. For example, ColE3 [supra] and a-sarcin [C. C. Correll, X. Yang, T. Gerczei, J. Beneken, M. J. Plantinga, J. Synchrotron Radiat. 2004, 11, 93-96], the two bacterial toxins that cleave a single phosphodiester bond of rRNA (in the small and large ribosomal subunits, respectively), both use RNA base flipping to dock the substrate into the active site in such a manner so as to facilitate crucial in-line attack.

In order to assess whether the aminoglycoside-warhead combination can induce a similar conformational change in the rRNA A-site, the angle created between the 2'-OH (the G1491 ribose, the nucleophile), the phosphorus of the phosphate between G1491 and A1492, and the 5'-O (the leaving group), O—P—O angle, was measured.

In the crystal structure of the Westhof model used for the simulations, the O—P—O angle does not exceed 908. The distributions of the O—P—O angle, as obtained from GaMD simulations of NeoB and Compounds 2, 5, 8, and 10 are shown in FIG. 14. The smallest values of this angle are found for the NeoB complex, distributed in the range of 45 to 1058. The interactions formed between O3' of NeoB (ring I) and OP2 of the A1492 phosphate and between O4' of NeoB (ring I) and OP2 of the A1493 phosphate seem to be the most important for orientation of the O—P—O angle. The modifications introduced into NeoB ring I to make Compounds 8 and 10 clearly lead to an increase in this angle for both derivatives, reaching as high as 1700 for Compound 10.

For Compound 8, this requirement is fulfilled thanks to the persistent hydrogen bond formed by the 3'-hydroxy group of ring I and concomitant stabilization of the A1492 phosphate by the N4 ammonium group of the warhead. For Compound 10, the crucial shortrange interaction with the OP1 atom of the A1492 phosphate is made by the N4' ammonium in ring I. Thus, stabilization of the O—P—O angle in the nearly in-line orientation is remarkable.

Example 6

Cytotoxicity and Eukaryotic Translation Inhibition

The cytotoxicity of the new compounds is determined in two kidney-derived cells, COS-7 and HEK-293 as previously reported [I. Nudelman, D. Glikin, B. Smolkin, M. Hainrichson, V. Belakhov, T. Baasov, Bioorganic Med. Chem. 2010, 18, 3735-3746; J. Kandasamy Atia-Glikin, D., Belakhov, V. and Baasov, T., Med Chem Comm 2011, 2, 165-171; A. Rebibo-Sabbah, I. Nudelman, Z. M. Ahmed, T. Baasov, T. Ben-Yosef, Hum. Genet. 2007, 122, 373-381].

The compounds are further tested for their selectivity towards bacterial ribosomes versus eukaryotic cytoplasmic and mitochondrial ribosomes. For this purpose, the inhibition of translation in eukaryotic and mitochondrial systems is performed, as previously reported [Nudelman, D. Glikin, B. Smolkin, M. Hainrichson, V. Belakhov, T. Baasov, Bioorganic Med. Chem. 2010, 18, 3735-3746; I. Nudelman, A. Rebibo-Sabbah, M. Cherniavsky, V. Belakhov, M. Hainrichson, F. Chen, J. Schacht, D. S. Pilch, T. Ben-Yosef, T. Baasov, J. Med. Chem. 2009, 52, 2836-2845; J. Kandasamy, D. Atia-Glikin, E. Shulman, K. Shapira, M. Shavit, V. Belakhov, T. Baasov, J. Med. Chem. 2012, 55, 10630-10643].

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A compound represented by Formula I:

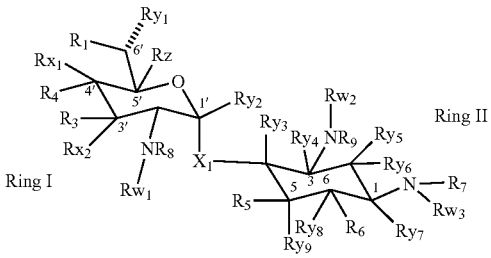

Formula I or a pharmaceutically acceptable salt thereof,
wherein:

the dashed line indicates a stereo-configuration of position 6' being an R configuration or an S configuration;

$X_1$ is O;

Rx1, Rx2, Ry1 and Rz are each independently selected from hydrogen, alkyl and cycloalkyl;

Ry2-Ry9 and Rw1-Rw3 are each independently selected from hydrogen, alkyl, and cycloalkyl;

$R_5$ and $R_6$ are each independently $OR_{16}$, wherein $R_{16}$ is independently selected from hydrogen, a monosaccharide moiety, and a disaccharide moiety;

$R_7$-$R_9$ are each independently selected from the group consisting of hydrogen and acyl; and $R_3$ is $OR_{20}$, wherein $R_{20}$ is hydrogen, alkyl, or cycloalkyl; and wherein either:

$R_1$ is $NR_{23}R_{24}$, and each of $R_{23}$ and $R_{24}$ is independently hydrogen, alkyl, cycloalkyl or acyl, and wherein:
either:

$R_4$ is selected from:

$OR_{20}$, wherein $R_{20}$ is a diamine-containing moiety which is:

-(L1)n-N1-(L2)m-N2 wherein:

n and m are each 1;

L1 and L2 are each independently an alkylene of 2 or 3 carbon atoms in length;

N1 is amine —NR'—, wherein R' is hydrogen, alkyl, or cycloalkyl, wherein said alkyl group is of 1 carbon atom, 2 carbon atoms, or 3 carbon atoms; and N2 is selected from amine and guanidyl, said amine being —NR'R" group, wherein R' and R" is each independently hydrogen, alkyl, or cycloalkyl, or R' and R" form together a heterocyclic group; and wherein said alkyl group is of 1 carbon atom, 2 carbon atoms, or 3 carbon atoms, and a diamine-containing moiety which is:

—N1-(L2)m-N2-(L3)k-(N3)a-(L4)j(N4)b wherein:

m and k are each 1;

j is 0 or 1;

a is 1;

b is 0 or 1;

L2, L3 and L4, if present, are each independently an alkylene of 1, 2 or 3 carbon atoms in length;

N1 is amide;

N2 is amine —NR'—, wherein R' is hydrogen, alkyl, or cycloalkyl, wherein said alkyl group is of 1 carbon atom, 2 carbon atoms, or 3 carbon atoms;

N3 is amine —NR'—, wherein R' is hydrogen, alkyl, or cycloalkyl, wherein said alkyl group is of 1 carbon atom, 2 carbon atoms, or 3 carbon atoms, or, when b and j are each 0, N3 is amine —NR'R", wherein R' and R" are each independently hydrogen, alkyl, or cycloalkyl, or R' and R" form together a heterocyclic group; and wherein said alkyl group is of 1 carbon atom, 2 carbon atoms, or 3 carbon atoms; and N4, if present, is amine —NR'R", wherein R' and R" is each independently hydrogen, alkyl, or cycloalkyl, or R' and R" form together a heterocyclic group; and wherein said alkyl group is of 1 carbon atom, 2 carbon atoms, or 3 carbon atoms, or:

$R_4$ is $OR_{20}$ wherein $R_{20}$ is hydrogen, alkyl, or cycloalkyl, or $NR_{23}R_{24}$ wherein each of $R_{23}$ and $R_{24}$ is independently hydrogen, alkyl, cycloalkyl or acyl; and $R_1$ is a diamine-containing moiety which is:

—N1-(L2)$m$-N2-(L3)$k$-(N3)$a$-(L4)$j$-(N4)$b$ wherein:

m and k are each 1;

j is 0 or 1;

a is 1;

b is 0 or 1;

L2, L3 and L4, if present, are each independently an alkylene of 1, 2 or 3 carbon atoms in length;

N1 is amide;

N2 is amine —NR'—, wherein R' is hydrogen, alkyl, or cycloalkyl, wherein said alkyl group is of 1 carbon atom, 2 carbon atoms, or 3 carbon atoms;

N3 is amine —NR'—, wherein R' is hydrogen, alkyl, or cycloalkyl, wherein said alkyl group is of 1 carbon atom, 2 carbon atoms, or 3 carbon atoms, or, when b and j are each 0, N3 is amine —NR'R", wherein R' and R" are each independently hydrogen, alkyl, or cycloalkyl, or R' and R" form together a heterocyclic group; and wherein said alkyl group is of 1 carbon atom, 2 carbon atoms, or 3 carbon atoms; and N4, if present, is amine —NR'R", wherein R' and R" is each independently hydrogen, alkyl, or cycloalkyl, or R' and R" form together a heterocyclic group; and wherein said alkyl group is of 1 carbon atom, 2 carbon atoms, or 3 carbon atoms.

2. The compound of claim 1, wherein $R_4$ is $OR_{20}$, and $R_{20}$ is said diamine-containing moiety, and wherein:

N1 is said amine —NR'— wherein R' is hydrogen, L2 is ethylene, and N2 is said amine NR'R" group, wherein R' and R" are each hydrogen, such that said diamine-containing moiety comprises an ethylene diamine moiety; or N1 is said amine —NR'— wherein R' is hydrogen, L2 is ethylene, and N2 is said amine NR'R" group, wherein R' is hydrogen and R" is methyl, such that said diamine-containing moiety comprises a methyl ethylenediamine moiety; or N1 is said amine —NR'— wherein R' is hydrogen, L2 is ethylene, and N2 is said amine NR'R" group, wherein R' and R" form together pyrrolidone, such that said diamine-containing moiety comprises a N-(2-aminoethyl)pyrrolidone moiety; or N1 is said amine —NR'— wherein R' is hydrogen, L2 is ethylene, and N2 is said guanidinyl, such that said diamine-containing moiety comprises a guanidine-ethyleneamine moiety.

3. The compound of claim 1, wherein $R_4$ is $OR_{20}$ and $R_{20}$ is said diamine-containing moiety.

4. The compound of claim 1, wherein at least one of $R_5$ and $R_6$ is $OR_{16}$, and $R_{16}$ is a monosaccharide or a disaccharide.

5. The compound of claim 1, wherein each of Rx1, Rx2, Ry1 and Rz is hydrogen.

6. The compound of claim 1, wherein each of Ry2-Ry9 and Rw1-Rw3 is hydrogen.

7. The compound of claim 1, wherein each of $R_7$ and $R_9$ is hydrogen.

8. The compound of claim 1, selected from:

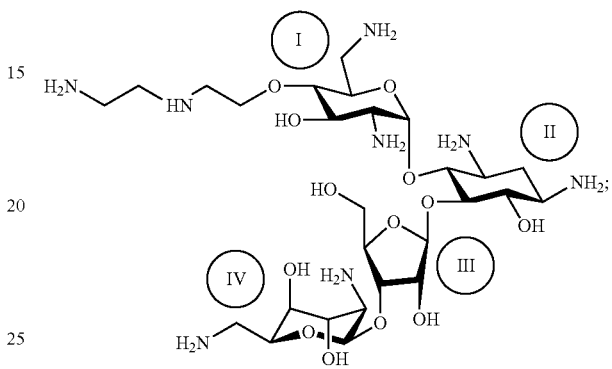

Compound 2

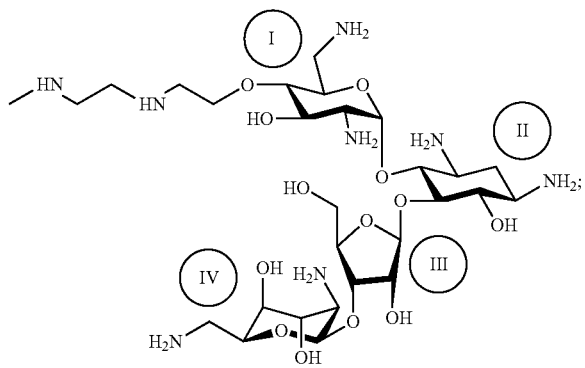

Compound 3

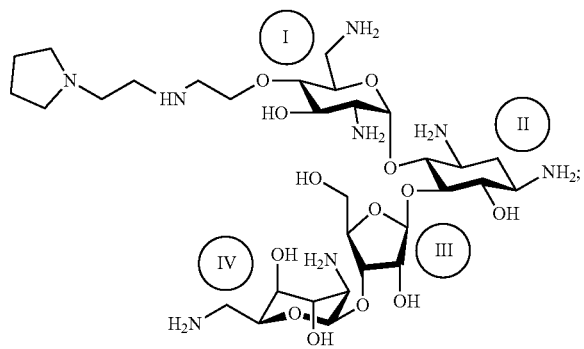

Compound 4

Compound 5

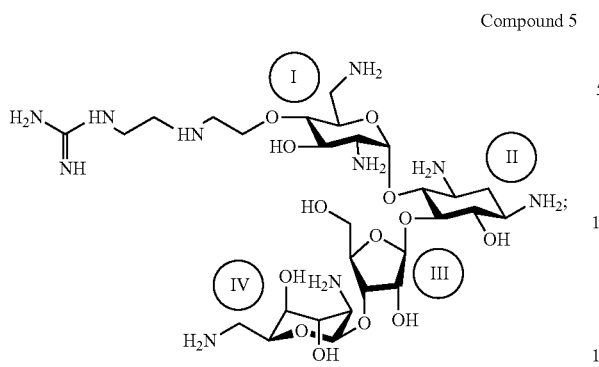

Compound 6

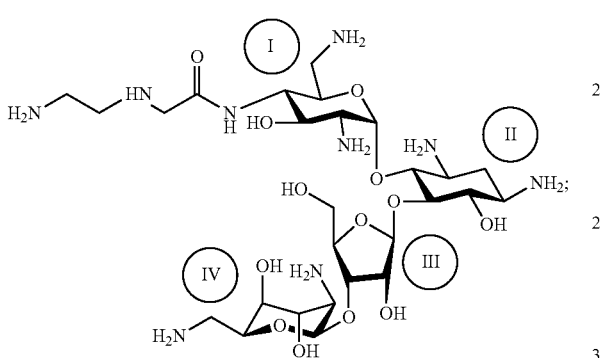

Compound 7

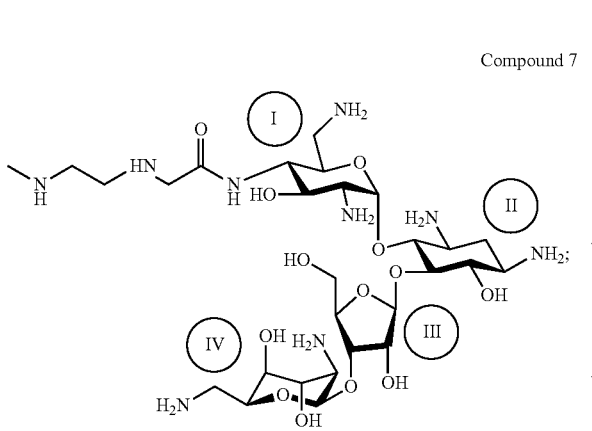

Compound 8

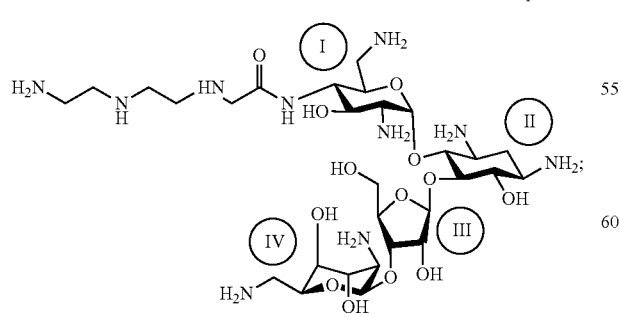

Compound 9

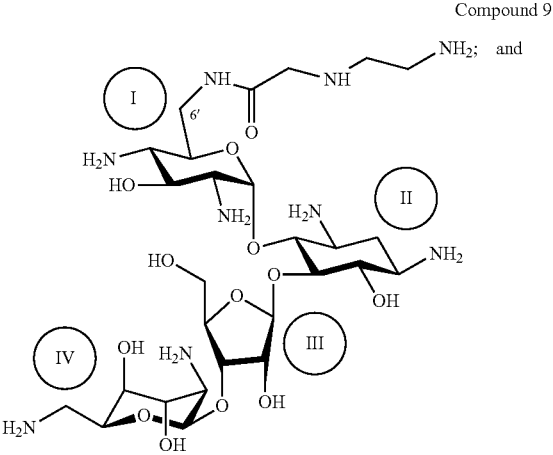

Compound 10

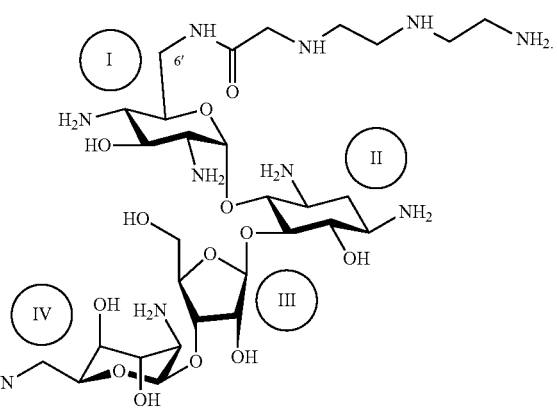

9. A pharmaceutical composition comprising a compound according to claim 1.

10. The compound of claim 1, wherein $R_4$ is said diamine-containing moiety which is:

—N1-(L2)$m$-N2-(L3)$k$-(N3)$a$-(L4)$j$-(N4)$b$ and wherein:

j and b are each 0, N2 is said amine —NR'— wherein R' is hydrogen, L3 is ethylene, and N3 is said amine NR'R" group, wherein R' and R" are each hydrogen, such that said diamine-containing moiety comprises an ethylene diamine moiety; or j and b are each 0, N2 is said amine —NR'— wherein R' is hydrogen, L3 is ethylene, and N3 is said amine NR'R" group, wherein R' is hydrogen and R" is methyl, such that said diamine-containing moiety comprises a methyl ethylenediamine moiety; or j and b are each 1, N2 is said amine —NR'— wherein R' is hydrogen, L3 and L4 are each ethylene, N3 is said amine —NR'— wherein R' is hydrogen, and N4 is said amine NR'R" group, wherein R' and R" are each hydrogen, such that said diamine-containing moiety comprises a diethylenetriamine moiety.

11. A method of treating a bacterial infection caused by an aminoglycoside-resistant bacteria in a subject in need thereof, the method comprising administering to the subject a compound according to claim 1.

* * * * *